United States Patent
Mumaw et al.

(10) Patent No.: US 11,925,335 B2
(45) Date of Patent: Mar. 12, 2024

(54) SURGICAL INSTRUMENT WITH SLIP RING ASSEMBLY TO POWER ULTRASONIC TRANSDUCER

(71) Applicant: Cilag GmbH International, Zug (CH)

(72) Inventors: Daniel J. Mumaw, Liberty Township, OH (US); Shawn D. Bialczak, Fort Thomas, KY (US); Sora Rhee, Pennsylvania Furnace, PA (US); Craig T. Davis, Cincinnati, OH (US); John A. Weed, III, Monroe, OH (US); Kip M. Rupp, New Richmond, OH (US); Foster B. Stulen, Johns Island, SC (US); Timothy G. Dietz, Reading, MA (US); Kevin L. Houser, Springboro, OH (US)

(73) Assignee: Cilag GmbH International, Zug (CH)

( * ) Notice: Subject to any disclaimer, the term of this patent is extended or adjusted under 35 U.S.C. 154(b) by 354 days.

(21) Appl. No.: 17/167,476

(22) Filed: Feb. 4, 2021

(65) Prior Publication Data
US 2021/0186596 A1 Jun. 24, 2021

Related U.S. Application Data

(60) Continuation of application No. 14/992,104, filed on Jan. 11, 2016, now Pat. No. 10,959,769, which is a
(Continued)

(51) Int. Cl.
*A61B 18/14* (2006.01)
*A61B 17/00* (2006.01)
(Continued)

(52) U.S. Cl.
CPC .... *A61B 17/00234* (2013.01); *A61B 17/2812* (2013.01); *A61B 17/320068* (2013.01);
(Continued)

(58) Field of Classification Search
CPC .......................... A61B 17/1622; A61B 17/1624
See application file for complete search history.

(56) References Cited

U.S. PATENT DOCUMENTS

| 1,754,806 A | 4/1930 | Stevenson |
| 3,297,192 A | 1/1967 | Swett |
| (Continued) | | |

FOREIGN PATENT DOCUMENTS

| CN | 101507641 A | 8/2009 |
| CN | 101683281 A | 3/2010 |
| (Continued) | | |

OTHER PUBLICATIONS

Chinese First Office Action dated Apr. 3, 2015 for App. No. CN 201180064148.6, 4 pgs.
(Continued)

*Primary Examiner* — Rochelle D Turchen
(74) *Attorney, Agent, or Firm* — Frost Brown Todd LLP

(57) ABSTRACT

A surgical instrument includes a rotatable electrical coupling assembly having a first part and a second part that electrically couple and rotate relative to each other. The second part is carried by and rotates with a tube collar coupled to a transducer. A portion of the transducer is inserted through an aperture of the second part, but does not contact the second part. The first part of the assembly may electrically couple to the second part via pogo pins, brush contacts, or ball bearings. Alternatively, the first part may comprise conductive channels formed in the casing. The second part may comprise a rotatable drum with a conductive trace. In some versions, one or more components may comprise MID components. In another version, the rotatable electrical coupling assembly comprises a rotatable PC board and brush contact. Further still, a circuit board may be provided with the transducer inside a transducer casing.

20 Claims, 32 Drawing Sheets

Related U.S. Application Data division of application No. 13/274,480, filed on Oct. 17, 2011, now abandoned.

(60) Provisional application No. 61/487,846, filed on May 19, 2011, provisional application No. 61/410,603, filed on Nov. 5, 2010.

(51) Int. Cl.

| | | |
|---|---|---|
| A61B 17/28 | (2006.01) | |
| A61B 17/32 | (2006.01) | |
| A61B 18/00 | (2006.01) | |
| A61B 18/04 | (2006.01) | |
| A61B 18/12 | (2006.01) | |
| A61B 34/00 | (2016.01) | |
| A61B 46/10 | (2016.01) | |
| A61B 50/30 | (2016.01) | |
| A61B 90/00 | (2016.01) | |
| A61B 90/40 | (2016.01) | |
| A61N 7/00 | (2006.01) | |
| G16H 20/40 | (2018.01) | |
| G16H 40/63 | (2018.01) | |
| H01M 10/42 | (2006.01) | |
| H01M 10/46 | (2006.01) | |
| H02J 7/00 | (2006.01) | |
| H02J 50/10 | (2016.01) | |
| A61B 17/064 | (2006.01) | |
| A61B 17/285 | (2006.01) | |
| A61B 17/29 | (2006.01) | |
| A61B 50/00 | (2016.01) | |

(52) U.S. Cl.
CPC ...... *A61B 17/320092* (2013.01); *A61B 18/00* (2013.01); *A61B 18/04* (2013.01); *A61B 18/12* (2013.01); *A61B 18/1206* (2013.01); *A61B 18/14* (2013.01); *A61B 18/1442* (2013.01); *A61B 18/1445* (2013.01); *A61B 34/25* (2016.02); *A61B 46/10* (2016.02); *A61B 50/30* (2016.02); *A61B 90/08* (2016.02); *A61B 90/40* (2016.02); *A61N 7/00* (2013.01); *G16H 20/40* (2018.01); *G16H 40/63* (2018.01); *H01M 10/425* (2013.01); *H01M 10/46* (2013.01); *H02J 7/0044* (2013.01); *H02J 7/0045* (2013.01); *H02J 50/10* (2016.02); *A61B 2017/00017* (2013.01); *A61B 2017/00084* (2013.01); *A61B 2017/00398* (2013.01); *A61B 2017/0046* (2013.01); *A61B 2017/00473* (2013.01); *A61B 2017/00477* (2013.01); *A61B 2017/00482* (2013.01); *A61B 2017/00734* (2013.01); *A61B 2017/0084* (2013.01); *A61B 17/064* (2013.01); *A61B 17/285* (2013.01); *A61B 2017/291* (2013.01); *A61B 2017/2929* (2013.01); *A61B 2017/293* (2013.01); *A61B 2017/2931* (2013.01); *A61B 2017/2933* (2013.01); *A61B 2017/294* (2013.01); *A61B 2017/320069* (2017.08); *A61B 2017/320071* (2017.08); *A61B 2017/320094* (2017.08); *A61B 2017/320095* (2017.08); *A61B 2018/00178* (2013.01); *A61B 2018/0019* (2013.01); *A61B 2018/00589* (2013.01); *A61B 2018/00595* (2013.01); *A61B 2018/00601* (2013.01); *A61B 2018/00607* (2013.01); *A61B 2018/00702* (2013.01); *A61B 2018/00791* (2013.01); *A61B 2018/00988* (2013.01); *A61B 2018/1226* (2013.01); *A61B 18/1233* (2013.01); *A61B 2018/1253* (2013.01); *A61B 2018/126* (2013.01); *A61B 2018/1412* (2013.01); *A61B 2018/1455* (2013.01); *A61B 2050/005* (2016.02); *A61B 2050/0065* (2016.02); *A61B 2050/0067* (2016.02); *A61B 2050/0076* (2016.02); *A61B 2050/008* (2016.02); *A61B 2050/3007* (2016.02); *A61B 2050/3008* (2016.02); *A61B 2090/0803* (2016.02); *A61B 2090/0813* (2016.02); *A61B 2090/0814* (2016.02); *H01M 2220/30* (2013.01); *H02J 7/0048* (2020.01); *Y10T 29/49005* (2015.01); *Y10T 29/49895* (2015.01); *Y10T 29/53913* (2015.01)

(56) References Cited

U.S. PATENT DOCUMENTS

| | | |
|---|---|---|
| 3,419,198 A | 12/1968 | Pettersen |
| 3,619,671 A | 11/1971 | Shoh |
| 4,034,762 A | 7/1977 | Cosens et al. |
| 4,057,220 A | 11/1977 | Kudlacek |
| 4,526,177 A | 7/1985 | Rudy et al. |
| 4,535,773 A | 8/1985 | Yoon |
| 4,641,076 A | 2/1987 | Linden et al. |
| 4,662,068 A | 5/1987 | Polonsky |
| 4,666,037 A | 5/1987 | Weissman |
| 4,685,459 A | 8/1987 | Koch et al. |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. et al. |
| 4,878,493 A | 11/1989 | Pasternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,308,358 A | 5/1994 | Bond et al. |
| 5,322,055 A | 6/1994 | Davison |
| 5,339,799 A | 8/1994 | Kami et al. |
| 5,358,508 A | 10/1994 | Cobb et al. |
| 5,361,902 A | 11/1994 | Abidin et al. |
| 5,429,229 A | 7/1995 | Chester et al. |
| 5,438,997 A | 8/1995 | Sieben et al. |
| 5,449,370 A | 9/1995 | Vaitekumas |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,597,371 A | 1/1997 | Toukura |
| 5,597,531 A | 1/1997 | Liberti et al. |
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,707,369 A | 1/1998 | Vaitekunas et al. |
| 5,741,305 A | 4/1998 | Vincent et al. |
| 5,776,155 A | 7/1998 | Beaupre et al. |
| 5,792,165 A | 8/1998 | Klieman et al. |
| 5,800,336 A | 9/1998 | Ball et al. |
| 5,817,128 A | 10/1998 | Storz |
| 5,868,244 A | 2/1999 | Ivanov et al. |
| 5,873,873 A | 2/1999 | Smith et al. |
| 5,882,310 A | 3/1999 | Marian, Jr. |
| 5,935,144 A | 8/1999 | Estabrook |
| 5,938,633 A | 8/1999 | Beaupre |

(56) References Cited

U.S. PATENT DOCUMENTS

| | | |
|---|---|---|
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | Dimatteo et al. |
| 6,056,735 A | 5/2000 | Okada et al. |
| 6,063,098 A | 5/2000 | Houser et al. |
| 6,066,151 A | 5/2000 | Miyawaki et al. |
| 6,083,191 A | 7/2000 | Rose |
| 6,083,223 A | 7/2000 | Baker |
| 6,099,537 A | 8/2000 | Sugai et al. |
| 6,113,593 A | 9/2000 | Tu et al. |
| 6,123,702 A | 9/2000 | Swanson et al. |
| 6,147,480 A | 11/2000 | Osadchy et al. |
| 6,165,191 A | 12/2000 | Shibata et al. |
| 6,190,386 B1 | 2/2001 | Rydell |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,287,304 B1 | 9/2001 | Eggers et al. |
| 6,325,811 B1 | 12/2001 | Messerly |
| 6,339,368 B1 | 1/2002 | Leith |
| 6,398,755 B1 | 6/2002 | Belef et al. |
| 6,409,742 B1 | 6/2002 | Fulton, III et al. |
| 6,500,176 B1 | 12/2002 | Truckai et al. |
| 6,500,188 B2 | 12/2002 | Harper et al. |
| 6,512,667 B2 | 1/2003 | Shiue et al. |
| 6,514,267 B2 | 2/2003 | Jewett |
| 6,520,185 B1 | 2/2003 | Bommannan et al. |
| 6,561,983 B2 | 5/2003 | Cronin et al. |
| 6,562,032 B1 | 5/2003 | Ellman |
| 6,609,414 B2 | 8/2003 | Mayer et al. |
| 6,622,731 B2 | 9/2003 | Daniel et al. |
| 6,623,500 B1 | 9/2003 | Cook et al. |
| 6,626,901 B1 | 9/2003 | Treat et al. |
| 6,647,281 B2 | 11/2003 | Morency |
| 6,650,091 B1 | 11/2003 | Shiue et al. |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,669,690 B1 | 12/2003 | Okada et al. |
| 6,717,193 B2 | 4/2004 | Olewine et al. |
| 6,730,042 B2 | 5/2004 | Fulton et al. |
| 6,752,768 B2 | 6/2004 | Burdorff et al. |
| 6,753,673 B2 | 6/2004 | Shiue et al. |
| 6,758,855 B2 | 7/2004 | Fulton, III et al. |
| 6,761,698 B2 | 7/2004 | Shibata et al. |
| 6,761,701 B2 | 7/2004 | Cucin |
| 6,783,524 B2 | 8/2004 | Anderson et al. |
| 6,815,206 B2 | 11/2004 | Lin et al. |
| 6,821,671 B2 | 11/2004 | Hinton et al. |
| 6,836,097 B2 | 12/2004 | Turner et al. |
| 6,838,862 B2 | 1/2005 | Luu |
| 6,847,192 B2 | 1/2005 | Turner et al. |
| 6,860,880 B2 | 3/2005 | Treat et al. |
| 6,869,435 B2 | 3/2005 | Blake |
| 6,923,807 B2 | 8/2005 | Ryan et al. |
| 6,945,981 B2 | 9/2005 | Donofrio et al. |
| 6,982,696 B1 | 1/2006 | Shahoian |
| 6,998,822 B2 | 2/2006 | Turner et al. |
| 7,031,155 B2 | 4/2006 | Sauciuc et al. |
| 7,061,749 B2 | 6/2006 | Liu et al. |
| 7,077,853 B2 | 7/2006 | Kramer et al. |
| 7,083,589 B2 | 8/2006 | Banko et al. |
| 7,085,123 B2 | 8/2006 | Shiue et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,186,473 B2 | 3/2007 | Shiue et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger et al. |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckai et al. |
| 7,364,061 B2 | 4/2008 | Swayze et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Her et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,560,903 B2 | 7/2009 | Thrap |
| 7,563,142 B1 | 7/2009 | Wenger et al. |
| 7,573,151 B2 | 8/2009 | Acena et al. |
| 7,583,564 B2 | 9/2009 | Ketahara et al. |
| 7,638,958 B2 | 12/2009 | Philipp et al. |
| 7,643,378 B2 | 1/2010 | Genosar |
| 7,658,247 B2 | 2/2010 | Carter |
| 7,692,411 B2 | 4/2010 | Trainor et al. |
| 7,717,312 B2 | 5/2010 | Beetel |
| 7,721,936 B2 | 5/2010 | Shelton, IV et al. |
| 7,738,971 B2 | 6/2010 | Swayze et al. |
| 7,761,198 B2 | 7/2010 | Bhardwaj |
| 7,766,910 B2 | 8/2010 | Hixson et al. |
| 7,766,929 B2 | 8/2010 | Masuda |
| 7,770,722 B2 | 8/2010 | Donahoe et al. |
| 7,770,775 B2 | 8/2010 | Shelton et al. |
| 7,772,796 B2 | 8/2010 | Farritor et al. |
| 7,776,037 B2 | 8/2010 | Odom |
| 7,780,660 B2 | 8/2010 | Bourne et al. |
| 7,802,121 B1 | 9/2010 | Zansky et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,913,891 B2 | 3/2011 | Doll et al. |
| 7,922,063 B2 | 4/2011 | Zemlok et al. |
| 7,923,151 B2 | 4/2011 | Lam et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 7,977,921 B2 | 7/2011 | Bahai et al. |
| 7,982,439 B2 | 7/2011 | Trainor et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,083,120 B2 | 12/2011 | Shelton et al. |
| 8,097,011 B2 | 1/2012 | Hideo et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,642 B2 | 8/2012 | Houser et al. |
| 8,251,994 B2 | 8/2012 | McKenna et al. |
| 8,267,094 B2 | 9/2012 | Danek et al. |
| 8,277,446 B2 | 10/2012 | Heard |
| 8,292,882 B2 | 10/2012 | Danek et al. |
| 8,292,888 B2 | 10/2012 | Whitman |
| 8,298,253 B2 | 10/2012 | Charles |
| 8,301,262 B2 | 10/2012 | Mi et al. |

(56) References Cited

U.S. PATENT DOCUMENTS

| | | |
|---|---|---|
| 8,328,802 B2 | 12/2012 | Deville et al. |
| 8,333,764 B2 | 12/2012 | Francischelli et al. |
| 8,336,725 B2 | 12/2012 | Ramsey et al. |
| 8,337,097 B2 | 12/2012 | Cao |
| 8,344,690 B2 | 1/2013 | Smith et al. |
| 8,372,099 B2 | 2/2013 | Deville et al. |
| 8,377,059 B2 | 2/2013 | Deville et al. |
| 8,400,108 B2 | 3/2013 | Powell et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,222 B2 | 4/2013 | Whitfield et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,444,653 B2 | 5/2013 | Nycz et al. |
| 8,444,662 B2 | 5/2013 | Palmer et al. |
| 8,449,529 B2 | 5/2013 | Bek et al. |
| 8,461,744 B2 | 6/2013 | Wiener et al. |
| 8,487,487 B2 | 7/2013 | Dietz et al. |
| 8,550,106 B2 | 10/2013 | Hebach et al. |
| 8,550,981 B2 | 10/2013 | Woodruff et al. |
| 8,551,088 B2 | 10/2013 | Falkenstein et al. |
| 8,564,242 B2 | 10/2013 | Hansford et al. |
| 8,573,461 B2 | 11/2013 | Shelton et al. |
| 8,602,287 B2 | 12/2013 | Laurent et al. |
| 8,608,045 B2 | 12/2013 | Smith et al. |
| 8,617,077 B2 | 12/2013 | van Groningen et al. |
| 8,622,274 B2 | 1/2014 | Yates et al. |
| 8,623,027 B2 | 1/2014 | Price et al. |
| 8,632,535 B2 | 1/2014 | Shelton, IV et al. |
| 8,641,629 B2 | 2/2014 | Kurokawa |
| 8,657,174 B2 | 2/2014 | Yates et al. |
| 8,663,112 B2 | 3/2014 | Slayton et al. |
| 8,733,614 B2 | 5/2014 | Ross et al. |
| 8,758,342 B2 | 6/2014 | Bales et al. |
| 8,784,415 B2 | 7/2014 | Malackowski et al. |
| 8,808,319 B2 | 8/2014 | Houser et al. |
| 8,834,465 B2 | 9/2014 | Ramstein et al. |
| 8,864,761 B2 | 10/2014 | Johnson et al. |
| 8,906,017 B2 | 12/2014 | Rioux et al. |
| 8,939,974 B2 | 1/2015 | Boudreaux et al. |
| 8,961,441 B2 | 2/2015 | Cioanta et al. |
| 8,968,648 B2 | 3/2015 | Kaneko |
| 8,986,302 B2 | 3/2015 | Boudreaux et al. |
| 8,998,939 B2 | 4/2015 | Price et al. |
| 9,000,720 B2 | 4/2015 | Stulen et al. |
| 9,011,336 B2 | 4/2015 | Slayton et al. |
| 9,011,427 B2 | 4/2015 | Price et al. |
| 9,011,471 B2 | 4/2015 | Timm et al. |
| 9,017,355 B2 | 4/2015 | Smith et al. |
| 9,017,849 B2 | 4/2015 | Stulen et al. |
| 9,017,851 B2 | 4/2015 | Felder et al. |
| 9,023,071 B2 | 5/2015 | Miller et al. |
| 9,039,720 B2 | 5/2015 | Madan |
| 9,044,261 B2 | 6/2015 | Houser |
| 9,050,125 B2 | 6/2015 | Boudreaux |
| 9,060,750 B2 | 6/2015 | Lam |
| 9,072,523 B2 | 7/2015 | Houser et al. |
| 9,072,543 B2 | 7/2015 | Miller et al. |
| 9,078,671 B2 | 7/2015 | Beale et al. |
| 9,089,338 B2 | 7/2015 | Smith et al. |
| 9,095,346 B2 | 8/2015 | Houser et al. |
| 9,113,903 B2 | 8/2015 | Unger et al. |
| 9,161,803 B2 | 10/2015 | Yates et al. |
| 9,179,912 B2 | 11/2015 | Yates et al. |
| 9,186,046 B2 | 11/2015 | Ramamurthy et al. |
| 9,186,047 B2 | 11/2015 | Ramamurthy et al. |
| 9,192,428 B2 | 11/2015 | Houser et al. |
| 9,247,986 B2 | 2/2016 | Haberstich et al. |
| 9,308,009 B2 | 4/2016 | Madan et al. |
| 9,314,261 B2 | 4/2016 | Bales et al. |
| 9,318,271 B2 | 4/2016 | Fletcher et al. |
| 9,364,279 B2 | 6/2016 | Houser et al. |
| 9,364,288 B2 | 6/2016 | Smith et al. |
| 9,375,255 B2 | 6/2016 | Houser et al. |
| 9,381,058 B2 | 7/2016 | Houser et al. |
| 9,421,062 B2 | 8/2016 | Houser et al. |
| 9,441,954 B2 | 9/2016 | Ramamurthy et al. |
| 9,500,472 B2 | 11/2016 | Ramamurthy et al. |
| 9,500,473 B2 | 11/2016 | Ramamurthy et al. |
| 9,510,895 B2 | 12/2016 | Houser et al. |
| 9,526,921 B2 | 12/2016 | Kimball et al. |
| 9,597,143 B2 | 3/2017 | Madan et al. |
| 9,622,832 B2 | 4/2017 | Birkenbach et al. |
| 9,629,652 B2 | 4/2017 | Mumaw et al. |
| 9,649,150 B2 | 5/2017 | Houser et al. |
| 9,675,375 B2 | 6/2017 | Houser et al. |
| 9,782,214 B2 | 10/2017 | Houser et al. |
| 10,143,513 B2 | 12/2018 | Houser et al. |
| 10,537,380 B2 | 1/2020 | Houser et al. |
| 10,959,769 B2 | 3/2021 | Mumaw et al. |
| 2001/0032666 A1 | 10/2001 | Jenson et al. |
| 2002/0165577 A1 | 11/2002 | Witt et al. |
| 2003/0065311 A1 | 4/2003 | Wang et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2003/0144680 A1 | 7/2003 | Kellogg et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton, III et al. |
| 2005/0171522 A1 | 8/2005 | Chrisopherson |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0078484 A1 | 4/2007 | Talarico et al. |
| 2007/0100334 A1* | 5/2007 | McFarlin ........... A61B 17/1622 606/45 |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0097223 A1 | 4/2008 | Strickler et al. |
| 2008/0147058 A1 | 6/2008 | Horrell et al. |
| 2008/0150754 A1 | 6/2008 | Quendt |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0221478 A1 | 9/2008 | Ritchie et al. |
| 2008/0228104 A1 | 9/2008 | Uber, III et al. |
| 2008/0255413 A1 | 10/2008 | Zemlok et al. |
| 2008/0281301 A1 | 11/2008 | Deboer et al. |
| 2008/0315829 A1 | 12/2008 | Joens et al. |
| 2009/0043797 A1 | 2/2009 | Dorie et al. |
| 2009/0076506 A1 | 3/2009 | Baker |
| 2009/0090763 A1 | 4/2009 | Zemlok et al. |
| 2009/0096430 A1 | 4/2009 | Van Der Linde et al. |
| 2009/0143799 A1 | 6/2009 | Smith et al. |
| 2009/0143800 A1 | 6/2009 | Deville et al. |
| 2009/0253030 A1 | 10/2009 | Kooij |
| 2009/0281430 A1 | 11/2009 | Wilder |
| 2010/0021022 A1 | 1/2010 | Pittel et al. |
| 2010/0030218 A1 | 2/2010 | Prevost |
| 2010/0060231 A1 | 3/2010 | Trainor et al. |
| 2010/0069942 A1 | 3/2010 | Shelton |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Alexander et al. |

(56) References Cited

U.S. PATENT DOCUMENTS

| | | |
|---|---|---|
| 2010/0228250 A1 | 9/2010 | Brogna |
| 2010/0249665 A1 | 9/2010 | Roche |
| 2010/0268221 A1 | 10/2010 | Beller et al. |
| 2010/0274160 A1 | 10/2010 | Yachi et al. |
| 2011/0009694 A1 | 1/2011 | Schultz et al. |
| 2011/0074336 A1 | 3/2011 | Miller |
| 2011/0077514 A1 | 3/2011 | Ulric et al. |
| 2011/0080134 A1 | 4/2011 | Miller |
| 2011/0221398 A1 | 9/2011 | Ferber |
| 2012/0111591 A1 | 5/2012 | Shelton, IV et al. |
| 2012/0116260 A1 | 5/2012 | Johnson et al. |
| 2012/0116261 A1 | 5/2012 | Mumaw et al. |
| 2012/0116262 A1 | 5/2012 | Houser et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0179036 A1 | 7/2012 | Patrick et al. |
| 2012/0292367 A1 | 11/2012 | Morgan et al. |
| 2012/0305427 A1 | 12/2012 | Felder et al. |
| 2013/0085330 A1 | 4/2013 | Ramamurthy et al. |
| 2013/0090528 A1 | 4/2013 | Ramamurthy et al. |
| 2013/0118733 A1 | 5/2013 | Kumar |
| 2014/0088379 A1 | 3/2014 | Bhamra et al. |
| 2015/0305763 A1 | 10/2015 | Houser et al. |
| 2016/0206900 A1 | 7/2016 | Haberstich et al. |
| 2016/0329614 A1 | 11/2016 | Madan et al. |

FOREIGN PATENT DOCUMENTS

| | | |
|---|---|---|
| CN | 101819334 A | 9/2010 |
| DE | 102008051866 | 10/2010 |
| DE | 102009013034 | 10/2010 |
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 A1 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| JP | 2000-210301 A | 8/2000 |
| JP | 3744974 B | 2/2006 |
| JP | 3989121 B | 10/2007 |
| JP | 4145069 B | 9/2008 |
| WO | WO 1997/024072 | 7/1997 |
| WO | WO 97/45157 A1 | 12/1997 |
| WO | WO 2000/065682 | 2/2000 |
| WO | WO 2003/013374 | 2/2003 |
| WO | WO 2003/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |
| WO | WO 2013/036587 A1 | 3/2013 |

OTHER PUBLICATIONS

Chinese Third Office Action dated Jan. 25, 2016 for App. No. CN 201180064148.6, 5 pgs.
Chinese Fourth Office Action dated Oct. 9, 2016 for App. No. CN 201180064148.6, 5 pgs.
European Examination Report dated Nov. 2, 2016 for Application No. EP 11791089.3, 4 pgs.
European Search Report, Partial, and Provisional Written Opinion dated May 6, 2021 for Application No. EP 20215689.9, 13 pgs.
European Search Report, Extended, and Written Opinion dated Jul. 14, 2021 for Application No. EP 20215689.9, 18 pgs.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.
Australian First Examination Report dated Jun. 17, 2015 for App. No. 2011323279.
Australian First Examination Report dated May 18, 2015 for App. No. 2011323284.
Chinese First Office Action dated Jul. 1, 2015 for App. No. CN 201180063986.1.
Chinese First Office Action dated Jul. 23, 2015 for App No. CN 2011800639965.
Chinese Second Office Action dated Jun. 3, 2016 for App No. CN 2011800639965.
Chinese First Office Action dated Mar. 27, 2015 for App No. CN 2011800638214.
Chinese First Office Action dated Jan. 29, 2015 for App No. CN 2011800638159.
Chinese First Office Action dated Mar. 4, 2015 for App No. CN 201180063595X.
Chinese Second Office Action dated Aug. 4, 2015 for App No. CN 2011800641486.
EP Communication dated Feb. 19, 2014 for Application No. EP 11781972.2.
European Examination Report dated Jul. 6, 2018 for Application No. EP 11784888.7, 4 pgs.
Indian Office Action, Examination Report, dated Jul. 11, 2019 for Application No. 4009/DELNP/2013, 7 pgs.
Indian Office Action, Examination Report, dated Nov. 6, 2019 for Application No. 3984/DELNP/2013, 5 pgs.
International Search Report and Written Opinion dated Jan. 26, 2012 for Application No. PCT/US2011/059212.
International Preliminary Report on Patentability dated May 7, 2013 for Application No. PCT/US2011/059212.
Communication from International Searching Authority dated Jan. 24, 2012 for Application No. PCT/US2011/059215.
International Search Report dated Apr. 4, 2012 for Application No. PCT/US2011/059215.
International Preliminary Report on Patentability dated May 8, 2013 for Application No. PCT/US2011/059215.
International Search Report dated Feb. 13, 2012 for Application No. PCT/US2011/059217.
International Preliminary Report on Patentability dated May 7, 2013 for Application No. PCT/US2011/059217.
International Search Report dated Jun. 12, 2012 for Application No. PCT/US2011/059218.
International Preliminary Report on Patentability dated May 7, 2013 for Application No. PCY/US2011/059218.

(56) References Cited

OTHER PUBLICATIONS

International Search Report dated Jan. 26, 2012 for Application No. PCT/US11/059220.
International Preliminary Report on Patentability dated May 7, 2013 for Application No. PCT/US2011/059220.
Communication from International Searching Authority dated Feb. 2, 2012 for Application No. PCT/US2011/059222.
International Search Report dated Apr. 18, 2012 for Application No. PCT/US2011/059222.
International Preliminary Report on Patentability dated May 7, 2013 for Application No. PCT/US2011/059222.
International Search Report dated Feb. 1, 2012 for Application No. PCT/US11/059223.
International Preliminary Report on Patentability dated May 7, 2013 for Application No. PCT/US2011/059223.
International Search Report dated Jan. 12, 2012 for Application No. PCT/US11/059226.
International Preliminary Report on Patentability dated May 7, 2013 for Application No. PCT/US2011/059226.
International Search Report dated Mar. 15, 2012 for Application No. PCT/US2011/059338.
International Preliminary Report on Patentability dated May 7, 2013 for Application No. PCT/US2011/059338.
International Search Report dated Feb. 7, 2012 for Application No. PCT/US2011/059351.
International Preliminary Report on Patentability dated May 7, 2013 for Application No. PCT/US2011/059351.
International Search Report dated Feb. 2, 2012 for Application No. PCT/US2011/059354.
International Preliminary Report on Patentability dated May 7, 2013 for Application No. PCT/US2011/059354.
International Search Report dated May 29, 2012 for Application No. PCT/US11/059358.
International Preliminary Report on Patentability dated May 7, 2013 for Application No. PCT/US2011/059358.
Communication from International Searching Authority dated Feb. 6, 2012 for Application No. PCT/US2011/059362.
International Search Report dated Mar. 22, 2012 for Application No. PCT/US2011/059362.
International Preliminary Report on Patentability dated May 7, 2013 for Application No. PCT/US2011/059362.
International Search Report dated Jun. 4, 2012 for Application No. PCT/US2011/059365.
International Preliminary Report on Patentability dated May 8, 2013 for Application No. PCT/US2011/059365.
International Search Report dated Feb. 23, 2012 for Application No. PCT/US2011/059371.
International Preliminary Report on Patentability dated May 7, 2013 for Application No. PCT/US2011/059371.
Communication from International Searching Authority dated Feb. 2, 2012 for Application No. PCT/US2011/059378.
International Search Report dated May 24, 2012 for Application No. PCT/US2011/059378.
International Search Report and Written Opinion dated Feb. 2, 2012 for Application No. PCT/US2011/059378.
International Preliminary Report on Patentability dated May 7, 2013 for Application No. PCT/US2011/059378.
International Search Report dated Apr. 11, 2012 for Application No. PCT/US2011/059381.
International Search Report and Written Opinion dated Jul. 6, 2012 for PCT/US2011/059381.
International Preliminary Report on Patentability dated May 8, 2013 for Application No. PCT/US2011/059381.
Japanese Office Action, Notification of Reasons for Refusal, dated Sep. 8, 2015 for App. No. 2013-537829.
Japanese Office Action, Notification of Reasons for Refusal, dated Jul. 5, 2016 for App. No. 2013-537829.
Japanese Office Action, Notification of Reasons for Refusal, dated Sep. 29, 2015 for App. No. 2013-537832.
Japanese Office Action, Notification of Reasons for Refusal, dated Sep. 29, 2015 for App. No. 2013-537871.
Japanese Office Action, Notification of Reasons for Refusal, dated Sep. 29, 2015 for App. No. 2013-537872.
Japanese Office Action, Notification of Reasons for Refusal, dated Oct. 27, 2015 for App. No. 2013-537873.
Japanese Office Action, Notification of Reasons for Refusal, dated Sep. 29, 2015 for App. No. 2013-537877.
Office Action Non-Final dated Aug. 6, 2013 for U.S. Appl. No. 13/151,471.
Notice of Allowance dated Dec. 6, 2013 for U.S. Appl. No. 13/151,471.
Office Action Non-Final dated Mar. 28, 2014 for U.S. Appl. No. 13/151,471.
U.S. Office Action, Notice of Allowance, dated Aug. 19, 2014 for U.S. Appl. No. 13/151,471.
U.S. Office Action, Notice of Allowance, dated Nov. 21, 2014 for U.S. Appl. No. 13/151,471.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
U.S. Office Action, Non-Final, dated Aug. 14, 2014 for U.S. Appl. No. 13/151,481.
U.S. Office Action, Final, dated Apr. 1, 2015 for U.S. Appl. No. 13/151,481.
U.S. Office Action, Notice of Allowance, dated Jun. 10, 2015 for U.S. Appl. No. 13/151,481.
Restriction Requirement dated Jul. 5, 2013 for U.S. Appl. No. 13/151,488.
U.S. Office Action, Non-Final, dated Nov. 7, 2014 for U.S. Appl. No. 13/151,488.
Office Action Non-Final dated Jun. 14, 2013 for U.S. Appl. No. 13/151,498.
Office Action Final dated Nov. 21, 2013 for U.S. Appl. No. 13/151,498.
Office Action Non-Final dated Mar. 18, 2014 for U.S. Appl. No. 13/151,498.
U.S. Office Action, Notice of Allowance, dated Aug. 6, 2014 for U.S. Appl. No. 13/151,498.
U.S. Office Action, Notice of Allowance, dated Nov. 21, 2014 for U.S. Appl. No. 13/151,498.
Office Action Non-Final dated Jun. 18, 2014 for U.S. Appl. No. 13/151,503.
Office Action Non-Final dated Nov. 6, 2014 for U.S. Appl. No. 13/151,503.
Restriction Requirement dated Mar. 13, 2013 for U.S. Appl. No. 13/151,509.
Restriction Requirement dated Jun. 24, 2013 for U.S. Appl. No. 13/151,509.
Office Action Non-Final dated Sep. 26, 2013 for U.S. Appl. No. 13/151,509.
Office Action Final dated Jan. 29, 2014 for U.S. Appl. No. 13/151,509.
Office Action Non-Final dated Jul. 9, 2014 for U.S. Appl. No. 13/151,509.
U.S. Office Action, Notice of Allowance, dated Oct. 28, 2014 for U.S. Appl. No. 13/151,509.
U.S. Office Action, Notice of Allowance, dated Feb. 25, 2015 for U.S. Appl. No. 13/151,509.
Restriction Requirement dated Jun. 11, 2014 for U.S. Appl. No. 13/151,512.
U.S. Office Action, Notice of Allowance, dated Oct. 29, 2014 for U.S. Appl. No. 13/151,512.
U.S. Office Action, Notice of Allowance, dated Feb. 17, 2015 for U.S. Appl. No. 13/151,512.
U.S. Office Action, Restriction Requirement, dated Jul. 11, 2014 for U.S. Appl. No. 13/269,870.
U.S. Office Action, Non-Final, dated Jan. 5, 2015 for U.S. Appl. No. 13/269,870.
Restriction Requirement dated Feb. 28, 2013 for U.S. Appl. No. 13/270,667.

(56) References Cited

OTHER PUBLICATIONS

Office Action Non-Final dated Apr. 26, 2013 for U.S. Appl. No. 13/270,667.
Office Action Final dated Oct. 25, 2013 for U.S. Appl. No. 13/270,667.
U.S. Office Action, Non-Final, dated Jul. 29, 2014 for U.S. Appl. No. 13/270,667.
U.S. Office Action, Notice of Allowance, dated Dec. 17, 2014 for U.S. Appl. No. 13/270,667.
U.S. Office Action, Restriction Requirement, dated Jul. 9, 2014 for U.S. Appl. No. 13/270,684.
U.S. Office Action, Non-Final, dated Oct. 9, 2014 for U.S. Appl. No. 13/270,684.
U.S. Office Action, Restriction Requirement, dated Sep. 11, 2014 for U.S. Appl. No. 13/270,701.
U.S. Office Action, Non-Final, dated Dec. 16, 2014 for U.S. Appl. No. 13/270,701.
Office Action Non-Final dated Nov. 21, 2013 for U.S. Appl. No. 13/271,352.
U.S. Office Action, Restriction Requirement, dated Sep. 25, 2014 for U.S. Appl. No. 13/271,352.
U.S. Office Action, Restriction Requirement, dated Oct. 2, 2013 for U.S. Appl. No. 13/274,480.
Office Action Non-Final dated Feb. 14, 2014 for U.S. Appl. No. 13/274,480.
U.S. Office Action, Final, dated Jul. 17, 2014 for U.S. Appl. No. 13/274,480.
Office Action Non-Final dated May 1, 2015 for U.S. Appl. No. 13/274,480.
Office Action Final dated Sep. 10, 2015 for U.S. Appl. No. 13/274,480.
U.S. Office Action, Restriction Requirement, dated Dec. 9, 2013 for U.S. Appl. No. 13/274,496.
U.S. Office Action, Non-Final, dated Feb. 6, 2014 for U.S. Appl. No. 13/274,496.
U.S. Office Action, Final, dated May 15, 2014 for U.S. Appl. No. 13/274,496.
U.S. Office Action, Final, dated Aug. 22, 2014 for U.S. Appl. No. 13/274,496.
U.S. Office Action, Non-Final, dated Apr. 2, 2015 for U.S. Appl. No. 13/274,496.
Restriction Requirement dated Mar. 28, 2014 for U.S. Appl. No. 13/274,507.
Office Action Non-Final dated Jun. 19, 2014 for U.S. Appl. No. 13/274,507.
Office Action Non-Final dated Dec. 21, 2012 for U.S. Appl. No. 13/274,516.
Office Action Final dated Aug. 16, 2013 for U.S. Appl. No. 13/274,516.
Office Action Non-Final dated Dec. 6, 2013 for U.S. Appl. No. 13/274,516.
U.S. Office Action, Final, dated Jun. 12, 2014 for U.S. Appl. No. 13/274,516.
U.S. Office Action, Non-Final, dated Oct. 8, 2014 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Final dated Oct. 25, 2013 for U.S. Appl. No. 13/274,540.
U.S. Office Action, Non-Final, dated Aug. 26, 2014 for U.S. Appl. No. 13/274,540.
U.S. Office Action, Notice of Allowance, dated Jan. 21, 2015 for U.S. Appl. No. 13/274,540.
Office Action Non-Final dated Apr. 1, 2013 for U.S. Appl. No. 13/274,805.
Office Action Final dated Sep. 12, 2013 for U.S. Appl. No. 13/274,805.
U.S. Office Action, Non-Final, dated Aug. 14, 2014 for U.S. Appl. No. 13/274,805.
U.S. Office Action, Notice of Allowance, dated Nov. 28, 2014 for U.S. Appl. No. 13/274,805.
U.S. Office Action, Notice of Allowance, dated Jan. 21, 2015 for U.S. Appl. No. 13/274,805.
Restriction Requirement dated Apr. 29, 2013 for U.S. Appl. No. 13/274,830.
Office Action Non-Final dated Jun. 14, 2013 for U.S. Appl. No. 13/274,830.
Office Action Final dated Nov. 26, 2013 for U.S. Appl. No. 13/274,830.
U.S. Office Action, Non-Final, dated Oct. 22, 2014 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Final dated Dec. 5, 2013 for U.S. Appl. No. 13/275,495.
U.S. Office Action, Non-Final, dated Feb. 25, 2015 for U.S. Appl. No. 13/275,495.
Office Action Non-Final dated Jan. 6, 2014 for U.S. Appl. No. 13/275,514.
U.S. Office Action, Non-Final, dated Sep. 9, 2014 for U.S. Appl. No. 13/275,514.
Office Action Non-Final dated May 17, 2013 for U.S. Appl. No. 13/275,547.
Office Action Final dated Feb. 28, 2014 for U.S. Appl. No. 13/275,547.
U.S. Office Action, Non-Final, dated Aug. 20, 2014 for U.S. Appl. No. 13/275,547.
Office Action Non-Final dated Feb. 1, 2013 for U.S. Appl. No. 13/275,563.
Office Action Final dated Aug. 29, 2013 for U.S. Appl. No. 13/275,563.
U.S. Office Action, Non-Final, dated Oct. 23, 2014 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/246,660.
U.S. Office Action, Restriction Requirement, dated Jul. 9, 2014 for U.S. Appl. No. 13/276,660.
U.S. Office Action, Notice of Allowance dated Jun. 17, 2015 for U.S. Appl. No. 13/276,660.
U.S. Office Action, Notice of Allowance dated Sep. 18, 2015 for U.S. Appl. No. 13/276,660.
U.S. Office Action, Notice of Allowance dated Feb. 8, 2016 for U.S. Appl. No. 13/276,660.
Office Action Non-Final dated Dec. 21, 2012 for U.S. Appl. No. 13/276,673.
Office Action Non-Final dated Aug. 19, 2013 for U.S. Appl. No. 13/276,673.
Office Action Final dated Mar. 21, 2014 for U.S. Appl. No. 13/276,673.
U.S. Office Action, Non-Final, dated Aug. 14, 2014 for U.S. Appl. No. 13/276,673.
U.S. Office Action, Final, dated Mar. 13, 2015 for U.S. Appl. No. 13/276,673.
U.S. Office Action Non-Final dated Nov. 23, 2015 for U.S. Appl. No. 13/276,673.
U.S. Office Action, Notice of Allowance, dated Mar. 31, 2016 for U.S. Appl. No. 13/276,673.
U.S. Office Action, Notice of Allowance, dated Aug. 17, 2016 for U.S. Appl. No. 13/276,673.
Restriction Requirement dated Feb. 6, 2013 for U.S. Appl. No. 13/276,687.
Office Action Non-Final dated Jun. 12, 2013 for U.S. Appl. No. 13/276,687.
Notice of Allowance dated Nov. 12, 2013 for U.S. Appl. No. 13/276,687.
Notice of Allowance dated Jun. 2, 2014 for U.S. Appl. No. 13/276,687.
U.S. Office Action, Notice of Allowance, dated Sep. 12, 2014 for U.S. Appl. No. 13/276,687.
U.S. Office Action, Notice of Allowance, dated Dec. 23, 2014 for U.S. Appl. No. 13/276,687.
Restriction Requirement dated Feb. 21, 2013 for U.S. Appl. No. 13/276,707.

(56) References Cited

OTHER PUBLICATIONS

Office Action Non-Final dated May 6, 2013 for U.S. Appl. No. 13/276,707.
Office Action Final dated Sep. 27, 2013 for U.S. Appl. No. 13/276,707.
U.S. Office Action, Non-Final, dated Jan. 29, 2015 for U.S. Appl. No. 13/276,707.
Restriction Requirement dated Feb. 6, 2013 for U.S. Appl. No. 13/276,725.
U.S. Office Action, Non-Final, dated Aug. 20, 2014 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
Office Action Final dated Nov. 8, 2013 for U.S. Appl. No. 13/276,745.
Office Action Non-Final dated Feb. 28, 2014 for U.S. Appl. No. 13/276,745.
U.S. Office Action, Notice of Allowance, dated Oct. 7, 2014 for U.S. Appl. No. 13/276,745.
U.S. Office Action, Notice of Allowance, dated Dec. 19, 2014 for U.S. Appl. No. 13/276,745.
U.S. Office Action, Restriction Requirement, dated Sep. 24, 2014 for U.S. Appl. No. 13/277,328.
U.S. Office Action, Non-Final, dated Dec. 8, 2014 for U.S. Appl. No. 13/277,328.
U.S. Office Action, Final, dated Mar. 24, 2015 for U.S. Appl. No. 13/277,328.
U.S. Office Action, Notice of Allowance, dated Jun. 1, 2015 for U.S. Appl. No. 13/277,328.
U.S. Office Action, Notice of Allowance, dated Jun. 15, 2016 for U.S. Appl. No. 13/277,328.

* cited by examiner

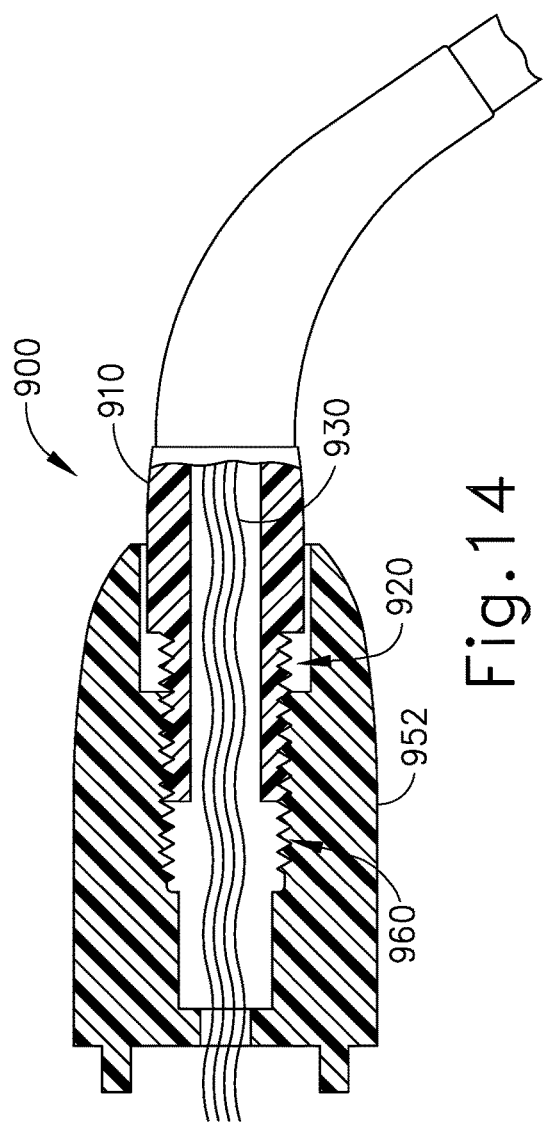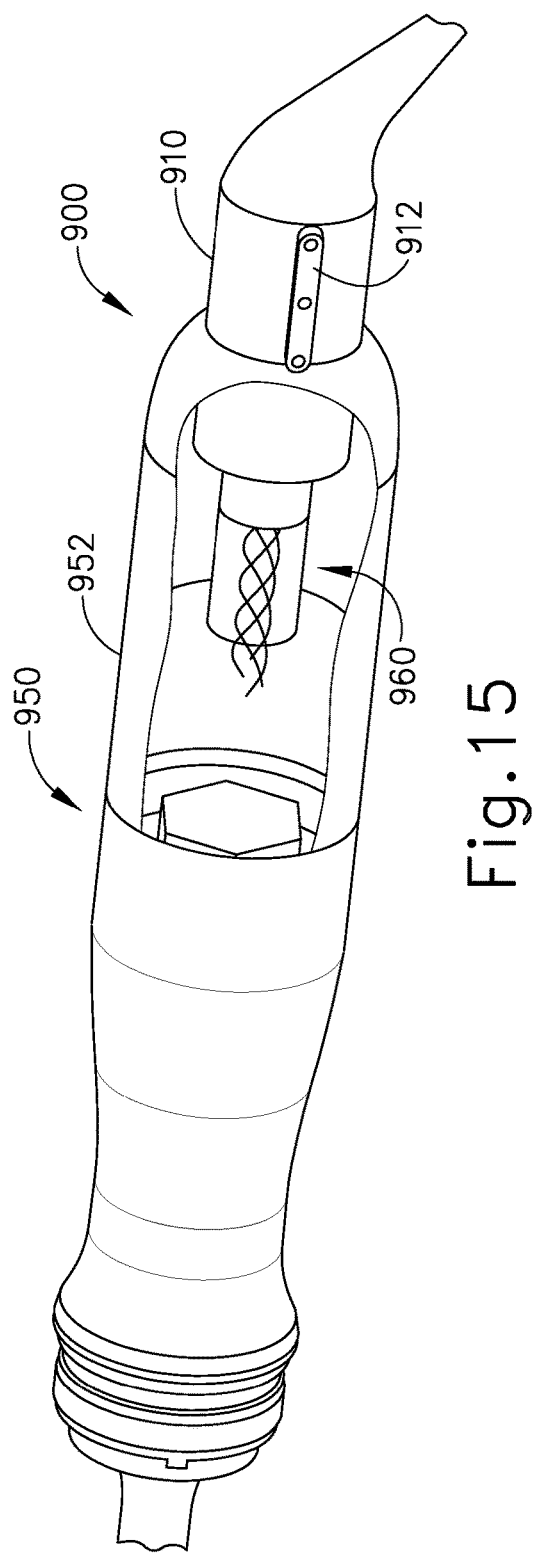

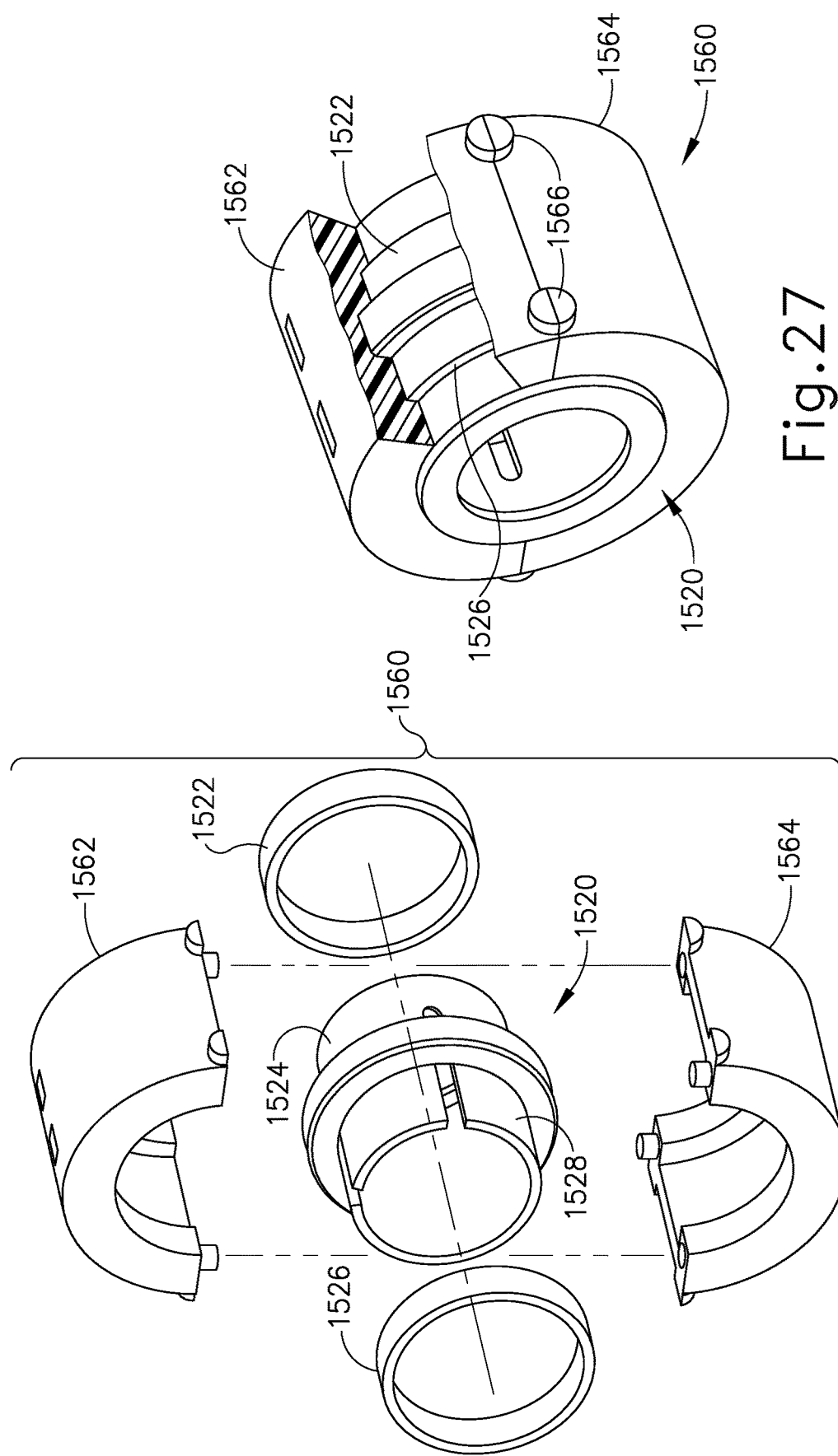

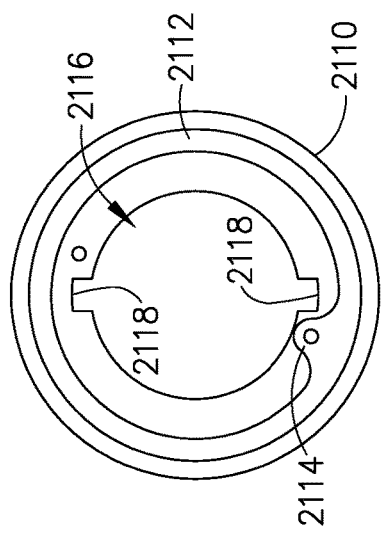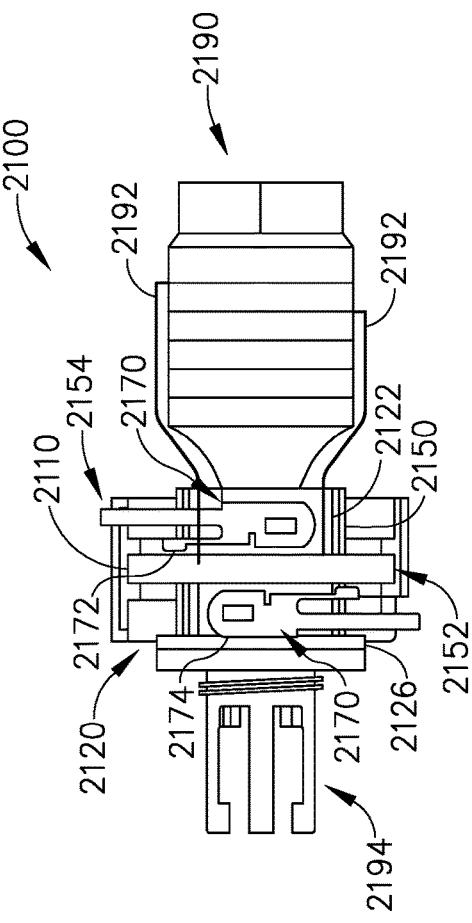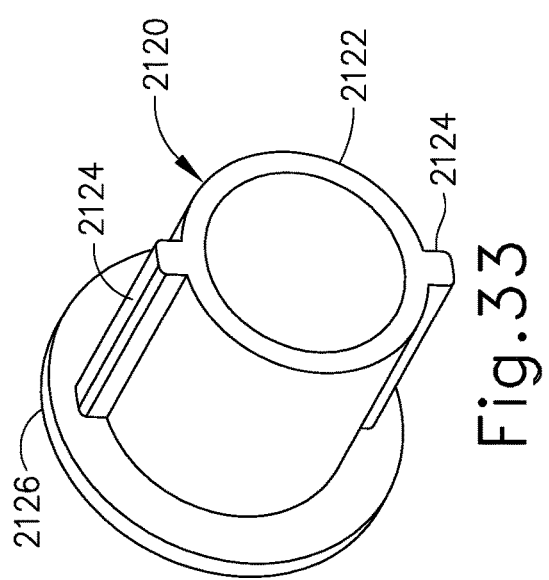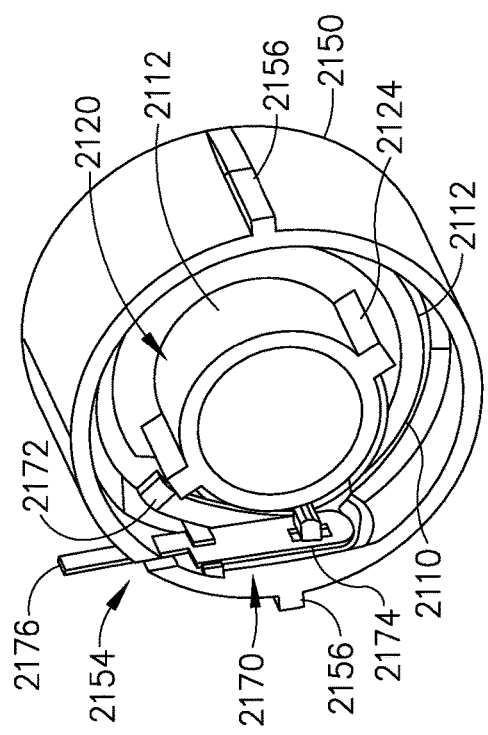

SURGICAL INSTRUMENT WITH SLIP RING ASSEMBLY TO POWER ULTRASONIC TRANSDUCER

PRIORITY

This application is a continuation of U.S. Non-Provisional Application Ser. No. 14/992,104, filed Jan. 11, 2016, entitled "Surgical Instrument with Slip Ring Assembly to Power Ultrasonic Transducer," issued as U.S. Pat. No. 10,959,769 on May 5, 2016, which is a divisional of U.S. Non-Provisional Application Ser. No. 13/274,480, filed Oct. 17, 2011, entitled "Surgical Instrument With Slip Ring Assembly To Power Ultrasonic Transducer," published as U.S. Pub. No. 2012/0116261 on May 10, 2012, now abandoned, which claims priority to U.S. Provisional Application Ser. No. 61/410,603, filed Nov. 5, 2010, entitled "Energy-Based Surgical Instruments," now expired, the disclosure of which is incorporated by reference herein.

U.S. Non-Provisional Application Ser. No. 13/274,480, published as U.S. Pat. Pub. No. 2021/0116261 on May 10, 2012, now abandoned, also claims priority to U.S. Provisional Application Ser. No. 61/487,846, filed May 19, 2011, entitled "Energy-Based Surgical Instruments," now expired, the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad Use with an Ultrasonic Surgical Instrument," published Apr. 13, 2006, now abandoned, the disclosure of which is incorporated by reference herein; U.S. Pat. Pub. No. 2007/0191713, entitled "Ultrasonic Device for Cutting and Coagulating," published Aug. 16, 2007, now abandoned, the disclosure of which is incorporated by reference herein; U.S. Pat. Pub. No. 2007/0282333, entitled "Ultrasonic Waveguide and Blade," published Dec. 6, 2007, now abandoned, the disclosure of which is incorporated by reference herein; U.S. Pat. Pub. No. 2008/0200940, entitled "Ultrasonic Device for Cutting and Coagulating," published Aug. 21, 2008, now abandoned, the disclosure of which is incorporated by reference herein; U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein. Additionally, such surgical tools may include a cordless transducer such as that disclosed in U.S. Pat. Pub. No. 2009/0143797, entitled "Cordless Hand-held Ultrasonic Cautery Cutting Device," published Jun. 4, 2009, issued as U.S. Pat. No. 8,419,757 on Apr. 16, 2013, the disclosure of which is incorporated by reference herein.

In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 14 depicts a side cross-sectional view of an exemplary rotatable electrical coupling assembly having a threaded cable and twistable wires;

FIG. 15 depicts a perspective view of the rotatable electrical coupling assembly of FIG. 14 showing the rotatable electrical coupling assembly coupled to a proximal end of a transducer;

FIG. 26 depicts an exploded perspective view of the drum and casing of FIG. 25;

FIG. 27 depicts a perspective view of the drum and casing of FIG. 26 shown assembled together;

FIG. 33 depicts a perspective view of a rotation drum configured to carry a PC board;

FIG. 34 depicts front elevation view of a PC board having conductive traces;

FIG. 35 depicts a perspective view of an assembled exemplary rotatable electrical coupling assembly using the PC board of FIG. 34 and the rotation drum of FIG. 33;

FIG. 36 depicts a side elevation view of the assembled exemplary rotatable electrical coupling assembly of FIG. 35 shown with a portion of the transfer casing removed and with a transducer;

Figure 1:
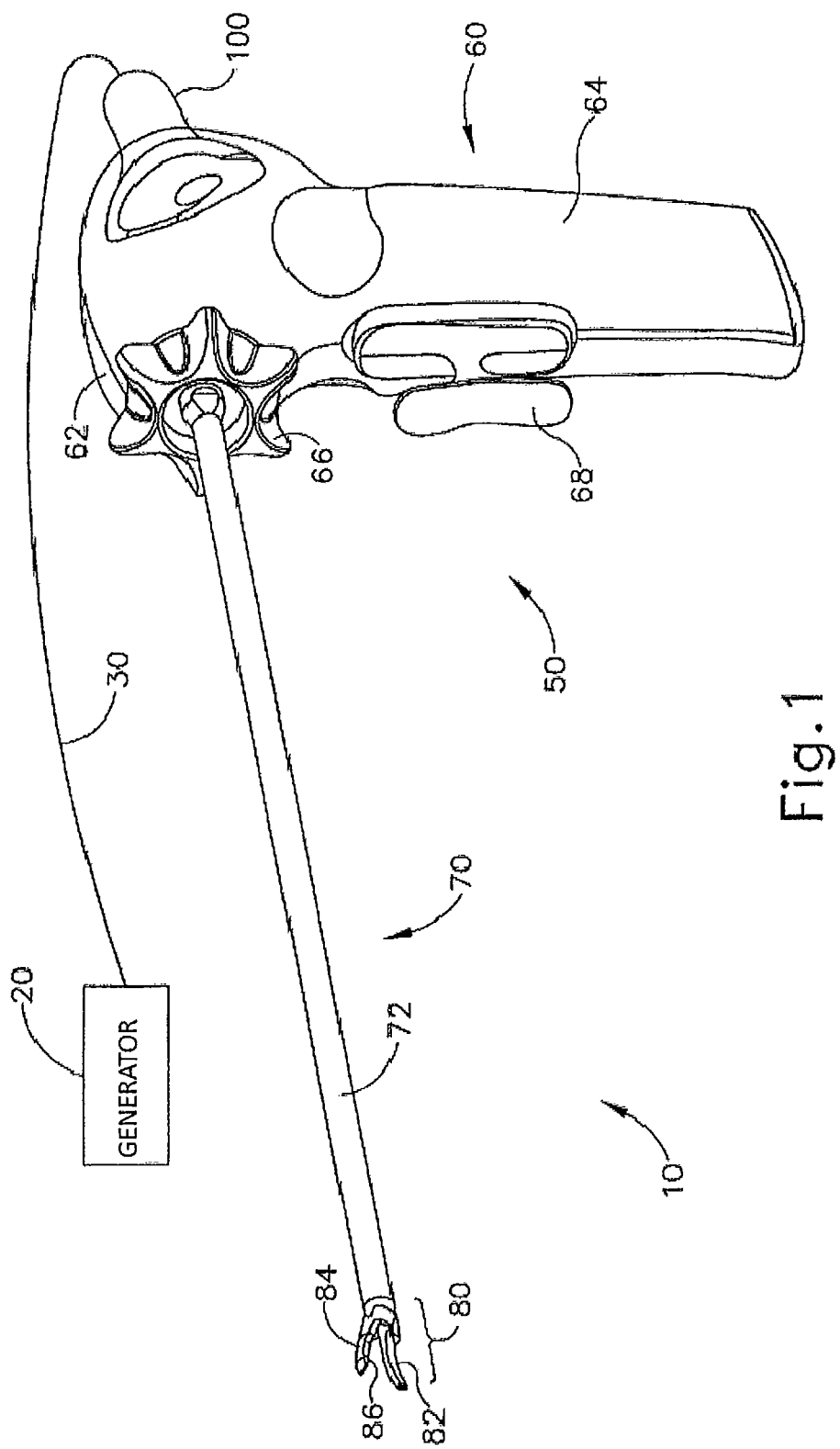
FIG. 1 depicts a perspective view of an exemplary surgical system comprising a surgical instrument and a generator.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Ultrasonic Surgical System

FIG. 1 shows an exemplary ultrasonic surgical system (10) comprising an ultrasonic surgical instrument (50), a generator (20), and a cable (30) operable to couple generator (20) to surgical instrument (50). A suitable generator (20) is the GEN 300 sold by Ethicon Endo-Surgery, Inc. of Cincinnati, Ohio. By way of example only, generator (20) may be constructed in accordance with the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should be noted that surgical instrument (50) will be described in reference to an ultrasonic surgical instrument; however, the technology described below may be used with a variety of surgical instruments, including, but not limited to, endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation, such as that disclosed in U.S. Pat. Pub. No. 2009/0143797, entitled "Cordless Hand-held Ultrasonic Cautery Cutting Device," published Jun. 4, 2009, issued as U.S. Pat. No. 8,419,757 on Apr. 16, 2013, the disclosure of which is incorporated by reference herein. Furthermore, surgical device (50) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example transmission assembly (70) is configured to be an elongated, thin tubular assembly for endoscopic use, but it should be understood that transmission assembly (70) may alternatively be a short assembly, such as those disclosed in U.S. Pat. Pub. No. 2007/0282333, entitled "Ultrasonic Waveguide and Blade," published Dec. 6, 2007, now abandoned, and U.S. Pat. Pub. No. 2008/0200940, entitled "Ultrasonic Device for Cutting and Coagulating," published Aug. 21, 2008, now abandoned, the disclosures of which are incorporated by reference herein. Transmission assembly (70) of the present example comprises an outer sheath (72), an inner tubular actuating member (not shown), a waveguide (not shown), and an end effector (80) located on the distal end of transmission assembly (70). In the present example, end effector (80) comprises a blade (82) coupled to the waveguide, a clamp arm (84) operable to pivot at the proximal end of transmission assembly (70), and, optionally, one or more clamp pads (86) coupleable to clamp arm (84). The waveguide, which is adapted to transmit ultrasonic energy from a transducer (100) to blade (82), may be flexible, semi-flexible, or rigid. One merely exemplary ultrasonic transducer (100) is Model No. HP054, sold by Ethicon Endo-Surgery, Inc. of Cincinnati, Ohio. It should also be understood that clamp arm (84) and associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein. The waveguide may also be configured to amplify the mechanical vibrations transmitted through the waveguide to blade (82) as is well known in the art. The waveguide may further have features to control the gain of the longitudinal vibration along the waveguide and features to tune the waveguide to the resonant frequency of the system.

In the present example, the distal end of the blade (82) is disposed near an anti-node in order to tune the acoustic assembly to a preferred resonant frequency $f_o$ when the acoustic assembly is not loaded by tissue. When transducer (100) is energized, the distal end of blade (82) is configured to move longitudinally in the range of, for example, approximately 10 to 500 microns peak-to-peak, and preferably in the range of about 20 to about 200 microns at a predetermined vibratory frequency $f_o$ of, for example, 55.5 kHz. When transducer (100) of the present example is activated, these mechanical oscillations are transmitted through the waveguide to end effector (80). In the present example, blade (82), being coupled to the waveguide, oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to also cauterize the tissue. While some configurations for transmission assembly (70) and transducer (100) have been described, still other suitable configurations for transmission assembly (70) and transducer (100) will be apparent to one or ordinary skill in the art in view of the teachings herein.

Multi-piece handle assembly (60) of the present example comprises a mating housing portion (62) and a lower portion (64). Mating housing portion (62) is configured to receive transducer (100) at a proximal end of mating housing portion (62) and to receive the proximal end of transmission assembly (70) at a distal end of mating housing portion (62). An aperture, described in more detail below, is provided on the distal end of mating housing portion (62) for insertion of various transmission assemblies (70). A rotation knob (66) is shown in the present example to rotate transmission assembly (70) and/or transducer (100), but it should be understood that rotation knob (66) is merely optional. Lower portion (64) of multi-piece handle assembly (60) includes a trigger (68) and is configured to be grasped by a user using a single hand. One merely exemplary alternative configuration for lower portion (64) is depicted in FIG. 1 of U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein.

Toggle buttons (not shown) may be located on a distal surface of lower portion (64) and may be operable to activate transducer (100) at different operational levels using generator (20). For instance, a first toggle button may activate transducer (100) at a maximum energy level while a second toggle button may activate transducer (100) at a minimum, non-zero energy level. Of course, the toggle buttons may be configured for energy levels other than a maximum and/or minimum energy level as will be apparent to one of ordinary skill in the art in view of the teachings herein. Moreover, the toggle buttons may be located anywhere else on multi-piece handle assembly (60), on transducer (100), and/or remote from surgical instrument (50), and any number of toggle buttons may be provided.

While multi-piece handle assembly (60) has been described in reference to two distinct portions (62, 64), it should be understood that multi-piece handle assembly (60)

may be a unitary assembly with both portions (62, 64) combined. Multi-piece handle assembly (60) may alternatively be divided into multiple discrete components, such as a separate activation portion (operable either by a user's hand or foot) and a separate mating housing portion (62). The activation portion may be operable to activate transducer (100) and may be remote from mating housing portion (62). Multi-piece handle assembly (60) may be constructed from a durable plastic (such as polycarbonate or a liquid crystal polymer), ceramics and/or metals or any other suitable material as will be apparent to one of ordinary skill in the art in view of the teachings herein. Still other configurations for multi-piece handle assembly (60) will be apparent to those of ordinary skill in the art in view of the teachings herein. For instance, instrument (50) may be operated as part of a robotic system. Other configurations for multi-piece handle assembly (60) will also be apparent to those of ordinary skill in the art in view of the teachings herein. By way of example only, surgical instrument (50) may be constructed in accordance with at least some of the teachings of U.S. Pat. Pub. No. 2006/0079874, now abandoned; U.S. Pat. Pub. No. 2007/0191713, now abandoned; U.S. Pat. Pub. No. 2007/0282333, now abandoned; U.S. Pat. Pub. No. 2008/0200940, now abandoned; U.S. Pat. Pub. No. 2011/0015660, issued as U.S. Pat. No. 8,461,744 on Jun. 11, 2013; U.S. Pat. No. 6,500,176; U.S. Pat. Pub. No. 2011/0087218, issued as U.S. Pat. No. 8,939,974 on Jan. 27, 2015; and/or U.S. Pat. Pub. No. 2009/0143797, issued as U.S. Pat. No. 8,419,757 on Apr. 16, 2013. Additional configurations that may be incorporated into surgical instrument (50) are described in U.S. patent application Ser. No. 13/269,899, entitled "Ultrasonic Surgical Instrument with Modular End Effector," filed Oct. 10, 2011, issued as U.S. Pat. No. 9,050,125 on Jun. 9, 2015, the disclosure of which is incorporated by reference herein.

II. Exemplary Rotatable Electrical Coupling Assemblies

In some instances it may be useful to a user to rotate transducer (100) while using surgical instrument (50). For example, rotation of transducer (100) may permit end effector (80) to be rotated such that clamp arm (84) may be reoriented relative to handle assembly (60). This may allow the user to clamp and sever tissue at a variety of angles. In some instruments, if cable (30) is directly electrically coupled to transducer (100), then rotation of transducer (100) and/or end effector (80) may twist cable (30) and/or the wires of cable (30). Accordingly, providing a rotatable electrical coupling may reduce or eliminate this potential twisting and/or binding of cable (30) and/or the wires.

A. Exemplary Nodal Flanged Transducer

Figure 2:
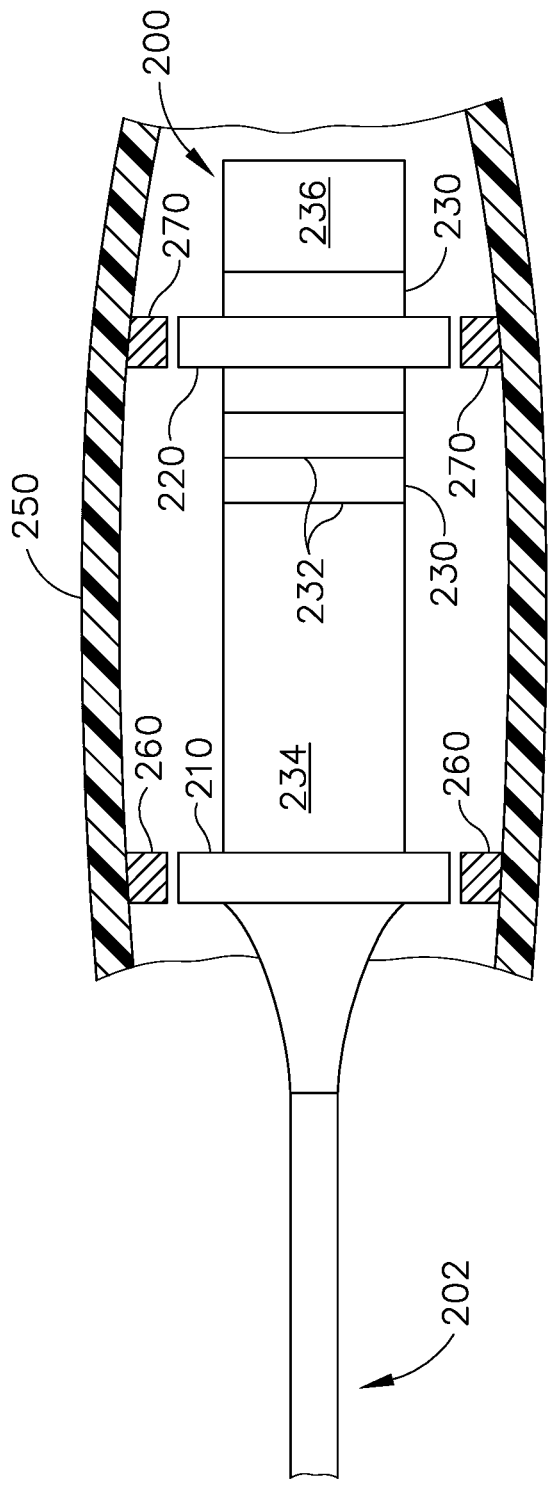
FIG. 2 depicts a side elevation view of an exemplary rotatable electrical coupling assembly for an exemplary transducer having nodal flanges.

FIG. 2 depicts an exemplary transducer (200) having a pair of nodal flanges (210, 220) operable to electrically couple transducer (200) to casing contacts (260, 270) of a casing (250). It should be understood that transducer (200) may constitute a modified version of transducer (100) described above. Transducer (200) of the present example comprises a plurality of piezoelectric elements (230) that are compressed between a first resonator (234) and a second resonator (236) to form a stack of piezoelectric elements. Piezoelectric elements (230) may be fabricated from any suitable material, for example, lead zirconate-titanate, lead meta-niobate, lead titanate, and/or any suitable piezoelectric crystal material. In the present example, distal nodal flange (210) includes a conductive material located on the circumference of distal nodal flange (210). Distal nodal flange (210) is coupled to first resonator (234) and is located at a node of transducer (200). A node is a point where the displacement due to the ultrasonic vibrations transmitted through transducer (200) is at zero. Proximal nodal flange (220) includes a conductive material located on the circumference of proximal nodal flange (220). In addition, proximal nodal flange (220) is located just distal of the proximal-most piezoelectric element (230) and is also located at a node of transducer (200), though this arrangement is merely optional. For instance, proximal nodal flange (220) may be coupled to second resonator (236), between other piezoelectric elements (230), on first resonator (234), and/or otherwise.

In the present example, proximal nodal flange (220) is configured to be electrically coupled to a positive, or "hot," wire from a cable, such as cable (30), while distal nodal flange (210) is configured to be electrically coupled to a negative or ground wire from the cable. Thus, nodal flanges (210, 220) are configured to create a voltage potential across the plurality of piezoelectric elements (230) therebetween via one or more electrodes (232) such that the plurality of piezoelectric elements (230) convert the electrical power into ultrasonic vibrations. Accordingly, when a power supply is coupled to the cable and the power supply is activated, such ultrasonic vibrations are transmitted distally to a waveguide (202). Waveguide (202) may be coupled to a blade of an end effector (such as blade (82) and end effector (80) described above) such that the ultrasonic oscillation of the blade may simultaneously sever the tissue and denature the proteins in adjacent tissue cells, thereby providing a coagulative effect with relatively little thermal spread.

In the present example, second resonator (236) is electrically coupled to distal nodal flange (210) via a center bolt (not shown). Second resonator (236) is also electrically coupled to the proximal-most piezoelectric element (230) such that a voltage potential is created across proximal-most piezoelectric element (230) from proximal nodal flange (220) to second resonator (236). It should be understood that proximal nodal flange (220) of the present example comprises an annulus that does not electrically couple to the center bolt. In some instances, an insulator may be provided between proximal nodal flange (220) and center bolt. Accordingly, no shim or wire is needed to cross proximal nodal flange (220) to electrically couple the proximal-most piezoelectric element (230) to distal nodal flange (210). In some versions, distal nodal flange (210) may be further configured to substantially secure transducer (200) in the axial direction while still permitting rotation. For instance, casing (250) may include a tab or collar to restrict the axial movement of distal nodal flange (210). In other versions, nodal flanges (210, 220) may include an annular groove such that casing contacts (260, 270) are insertable therein to ensure an adequate electrical connection. Of course transducer (200) and nodal flanges (210, 220) may have other configurations as will be apparent to one of ordinary skill in the art in view of the teachings herein.

Casing (250) of the present example may be constructed in accordance with at least some of the teachings of handle assembly (60) described above; U.S. Pat. Pub. No. 2006/0079874, now abandoned; U.S. Pat. Pub. No. 2007/0191713, now abandoned; U.S. Pat. Pub. No. 2007/0282333, now abandoned; U.S. Pat. Pub. No. 2008/0200940, now abandoned; U.S. Pat. Pub. No. 2011/0015660, issued as U.S. Pat. No. 8,461,744 on Jun. 11, 2013; U.S. Pat. No. 6,500,176; U.S. Pat. Pub. No. 2011/0087218, issued as U.S. Pat. No. 8,393,974 on Jan. 27, 2015; U.S. Pat. Pub. No. 2009/0143797, issued as U.S. Pat. No. 8,419,757 on Apr. 16, 2013; and/or otherwise. In the present example, casing (250) includes casing contacts (260, 270). Distal casing contact (260) is configured to electrically couple to distal nodal flange (210), and proximal casing contact (270) is configured to electrically couple to proximal nodal flange (220). Casing contacts (260, 270) of the present example are further configured to maintain the electrical coupling with nodal flanges (210, 220) even when transducer (200) is rotated. For instance, casing contacts (260, 270) may comprise resiliently biased pins, slip rings, resiliently biased leaf springs, resiliently biased lever arms with end contacts, and/or any other contact as will be apparent to one of ordinary skill in the art in view of the teachings herein. Casing contacts (260, 270) are electrically coupled to one or more wires (not shown) such that electrical power is transmittable from a power supply, such as generator (20) or a battery, to transducer (200). In some versions, one of the casing contacts (260, 270) may be electrically coupled to a wire that is electrically coupled to a switch that is operable by a trigger or button. Accordingly, the trigger or button may be used to selectively activate transducer (200). Of course further arrangements for casing (250) and casing contacts (260, 270) will be apparent to one of ordinary skill in the art in view of the teachings herein.

When the user is using a surgical instrument, the user may desire to rotate the end effector to sever tissue. Accordingly, casing contacts (260, 270) and nodal flanges (210, 220) permit the user to rotate the end effector and transducer (200) together through 360 degrees of rotation without disengaging transducer (200) from the power supply.

B. Exemplary Bridge Electrical Coupling

Figure 3:
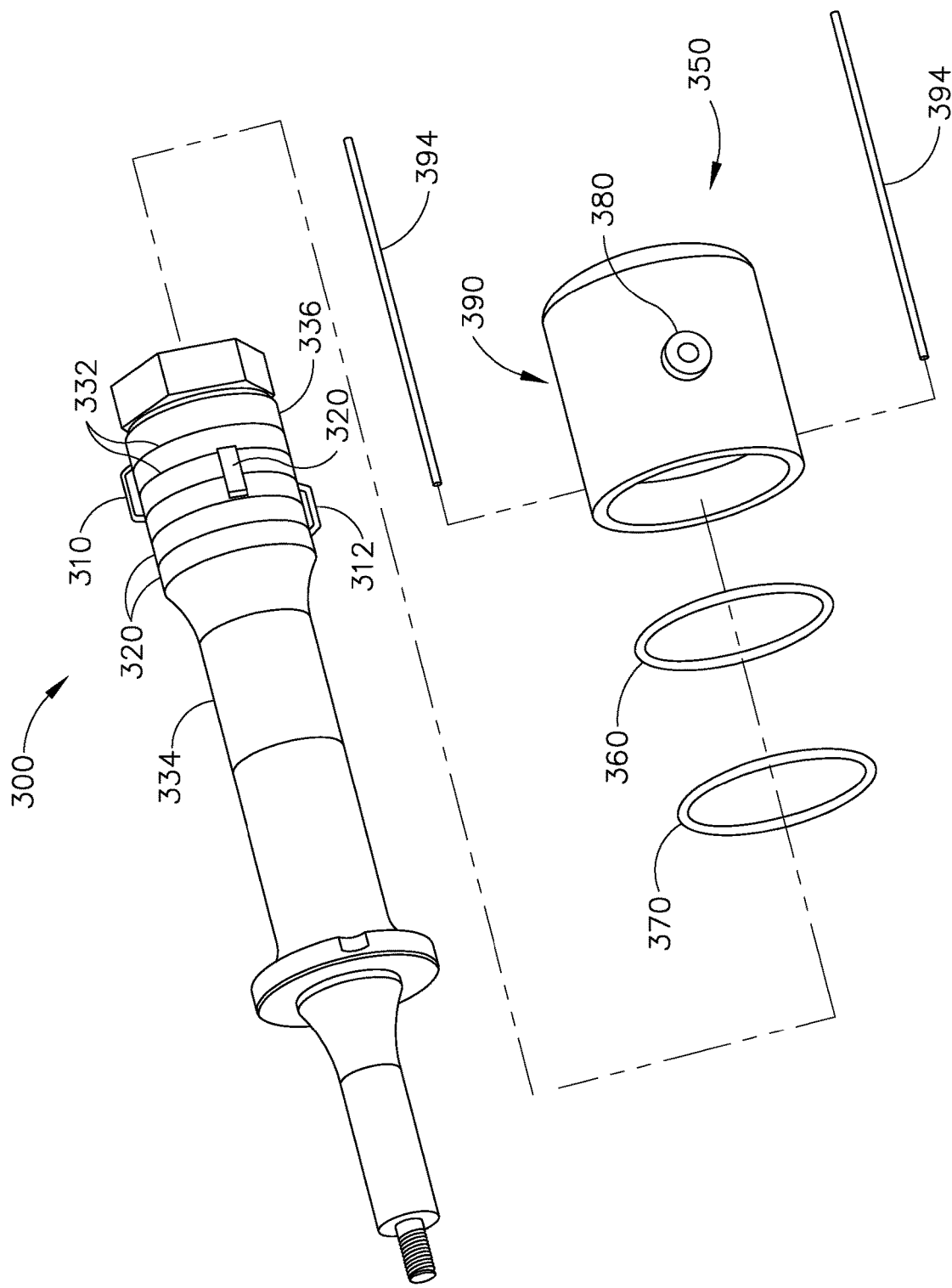
FIG. 3 depicts an exploded perspective view of an exemplary rotatable electrical coupling assembly having electrode bridges and ring contacts.
Figure 4:
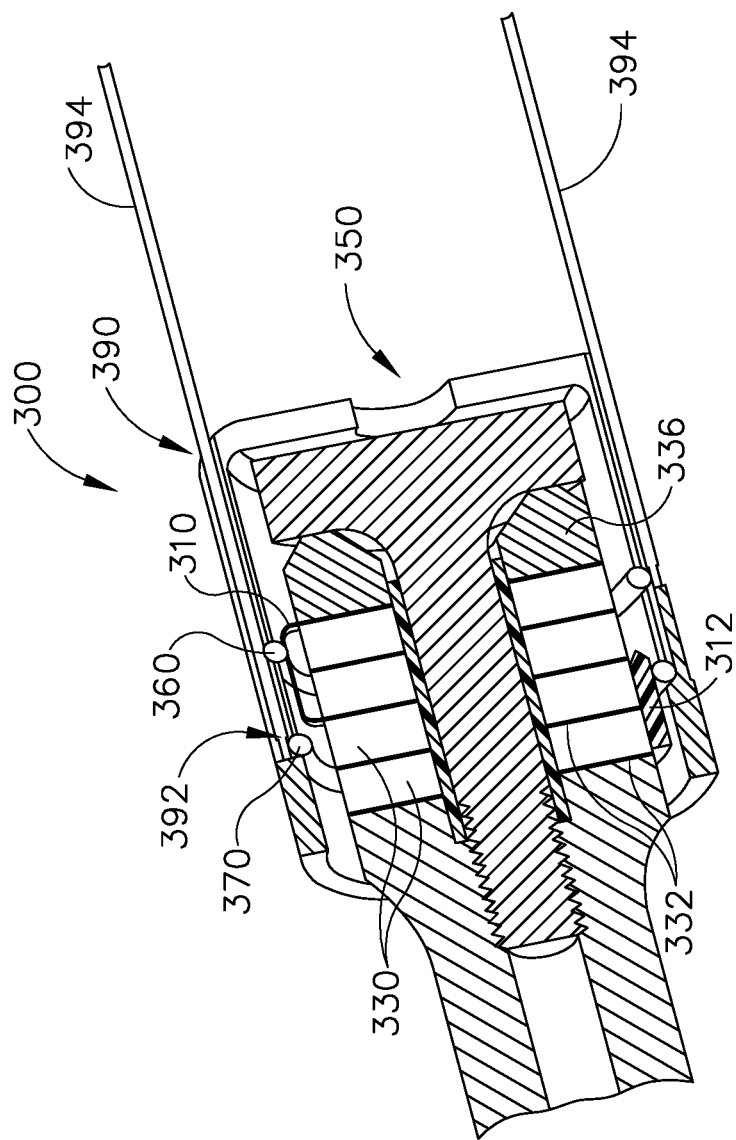
FIG. 4 depicts a partial perspective cross-sectional view the rotatable electrical coupling assembly of FIG. 3 showing a first bridge electrically coupled to a first ring contact and a subsequent bridge insulated from a second ring contact.
Figure 5:
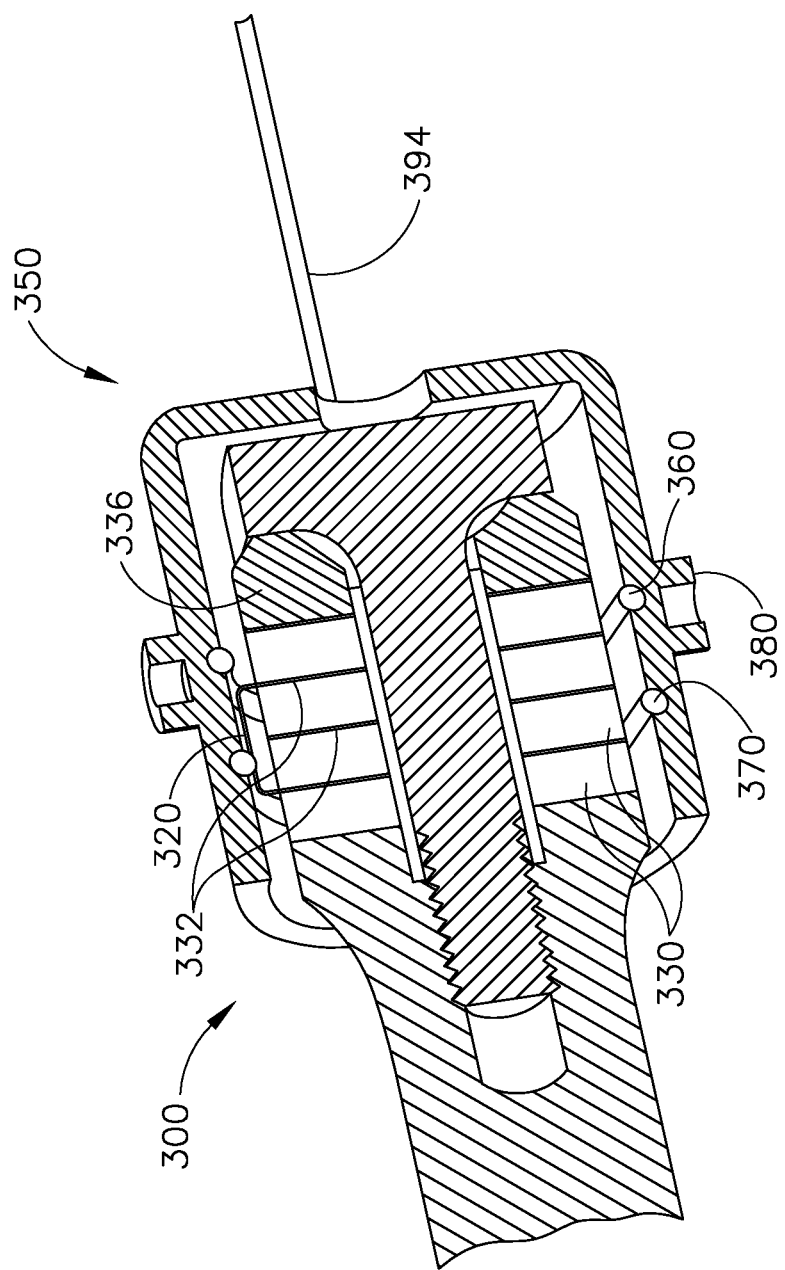
FIG. 5 depicts a partial perspective cross-sectional view the rotatable electrical coupling assembly of FIG. 3 showing a second bridge electrically coupled to a second ring contact.

FIGS. 3-5 depict another exemplary transducer (300) having bridges (310, 320) electrically coupling two or more alternating electrodes (332) of piezoelectric elements (330). Piezoelectric elements (330) are compressed between a first resonator (334) and a second resonator (336) to form a stack of piezoelectric elements. Piezoelectric elements (330) may be fabricated from any suitable material, for example, lead zirconate-titanate, lead meta-niobate, lead titanate, and/or any suitable piezoelectric crystal material between electrodes (332). In the present example, alternating electrodes (332) are electrically coupled via bridges (310, 320) such that a voltage potential is formed across the plurality of piezoelectric elements (330) when a power supply is coupled to bridges (310, 320). Accordingly, when the power supply is activated, the plurality of piezoelectric elements (330) convert the electrical power into ultrasonic vibrations. Such ultrasonic vibrations are transmitted distally to a waveguide (not shown). As described previously, the waveguide may be coupled to a blade of an end effector such that the ultrasonic oscillation of the blade may simultaneously sever the tissue and denature the proteins in adjacent tissue cells, thereby providing a coagulative effect with relatively little thermal spread.

As shown in FIG. 3, a first bridge (310) electrically couples a pair of alternating electrodes (332) and is configured to electrically couple to a power supply via a first ring contact (360), as will be described below. In the present example, first bridge (310) is configured to receive the positive, or "hot," electrical connection from the power supply. As shown in FIG. 3, a subsequent bridge (312) is electrically coupled to first bridge (310) via common electrode (332). Subsequent bridge (312) comprises an insulating material to electrically isolate subsequent bridge (312) from inadvertently electrically coupling to other components except the desired electrodes (332) to which subsequent bridge (312) is electrically coupled. Second bridge (320) electrically couples a pair of alternating electrodes (332) (that are different from the electrodes (332) that first bridge (310) electrically couples) and second bridge (320) is configured to electrically couple to a power supply via a second ring contact (370), as will be described below. In the present example, second bridge (320) is configured to receive the negative or ground electrical connection from the power supply. While the present exemplary transducer (300) depicts four piezoelectric elements (330), it should be understood that any number of piezoelectric elements (330) may be used, as will be apparent to one of ordinary skill in the art in view of the teachings herein. For instance, one or more additional bridges (not shown) having insulating similar to subsequent bridge (312) may be electrically coupled to second bridge (320) and/or first bridge (310) via a common electrode (332) or subsequent electrically coupled electrodes (332). Accordingly, a plurality of piezoelectric elements (330) and electrodes (332) may be coupled by bridges (310, 312, 320) to form any number of piezoelectric element stacks. Of course still further arrangements for transducer (300) and/or bridges (310, 312, 320) will be apparent to one of ordinary skill in the art in view of the teachings herein.

A transducer casing (350) comprises a first ring contact (360) and a second ring contact (370) disposed therein. In the present example, transducer casing (350) comprises a cup-like member having an open distal end that is configured to fit over the proximal end of transducer (300). Transducer casing (350) comprises a plastic member, though other non-conductive or conductive members with insulating may be used as well. In other versions, transducer casing (350) may be insulated electrically using a diode circuit or any other electrical components, as will be apparent to one of ordinary skill in the art in view of the teachings herein. As best seen in FIGS. 4-5, transducer casing (350) includes a pair of notches into which first ring contact (360) and second ring contact (370) are inserted and secured. Ring contacts (360, 370) may comprise split ring contacts, resilient leaf springs, coil springs, and/or any other contact as will be apparent to one of ordinary skill in the art in view of the teachings herein. First ring contact (360) is positioned such that first bridge (310) is substantially in contact with, and electrically coupled to, first ring contact (360) even when transducer (300) is rotated 360 degrees about a longitudinal axis. Second ring contact (370) is positioned such that second bridge (320) is substantially in contact with, and electrically coupled to, second ring contact (370) even when transducer (300) is rotated 360 degrees about a longitudinal axis. FIGS. 4-5 demonstrate one merely exemplary arrangement for ring contacts (360, 370) such that bridges (310, 320) electrically couple to the corresponding ring contacts (360, 370). As shown in FIG. 4, subsequent bridge (312) (which includes insulating material) contacts, but does not electrically couple to, second ring contact (370). Accordingly, a user may rotate transducer (300) within transducer casing (350) while bridges (310, 320) remain electrically coupled to ring contacts (360, 370).

Transducer casing (350) further comprises housing mounts (380) and a pair of longitudinal slots (390). Housing mounts (380) are operable to secure transducer casing (350) to a handle assembly, such as handle assembly (60) described above, such that transducer casing (350) does not rotate when transducer (300) is rotated. Longitudinal slots (390) each include a hole (392) through which a wire (394) may be coupled to a corresponding ring contact (360, 370). For instance, wires (394) may be soldered to ring contacts (360, 370). Alternatively, wires (394) may be coupled to ring contacts (360, 370) via selectively coupleable electrical connectors (spades, ring contacts, crimped connectors, etc.). Wires (394) are coupled to a power supply, such as generator (20) and/or a battery, such that electrical power is transmittable to ring contacts (360, 370) and subsequently to bridges (310, 320). In some versions, one of the wires (394) may be electrically coupled to a switch that is operable by a trigger or button such that the trigger or button may be used to selectively activate transducer (300).

Other suitable arrangements for transducer casing (350) and ring contacts (360, 370) will be apparent to one of ordinary skill in the art in view of the teachings herein. For instance, in some versions transducer casing (350) may include a distal member or tab operable to longitudinally secure transducer (300) to transducer casing (350). Such a distal member or tab may selectively engage a flange or other feature of transducer (300). In further versions, transducer casing (350) and/or transducer (300) may be carried by a translatable member such that the longitudinal location of transducer casing (350) and/or transducer (300) may be controlled by the user. For instance, transducer casing (350) may be actuatable via a trigger to selectively disengage and reengage ring contacts (360, 370) with bridges (310, 320) when trigger is pivoted. Such actuation may electrically isolate transducer (300) until the trigger is pulled.

C. Exemplary Plug-in Electrical Coupling Assembly

Figure 6:
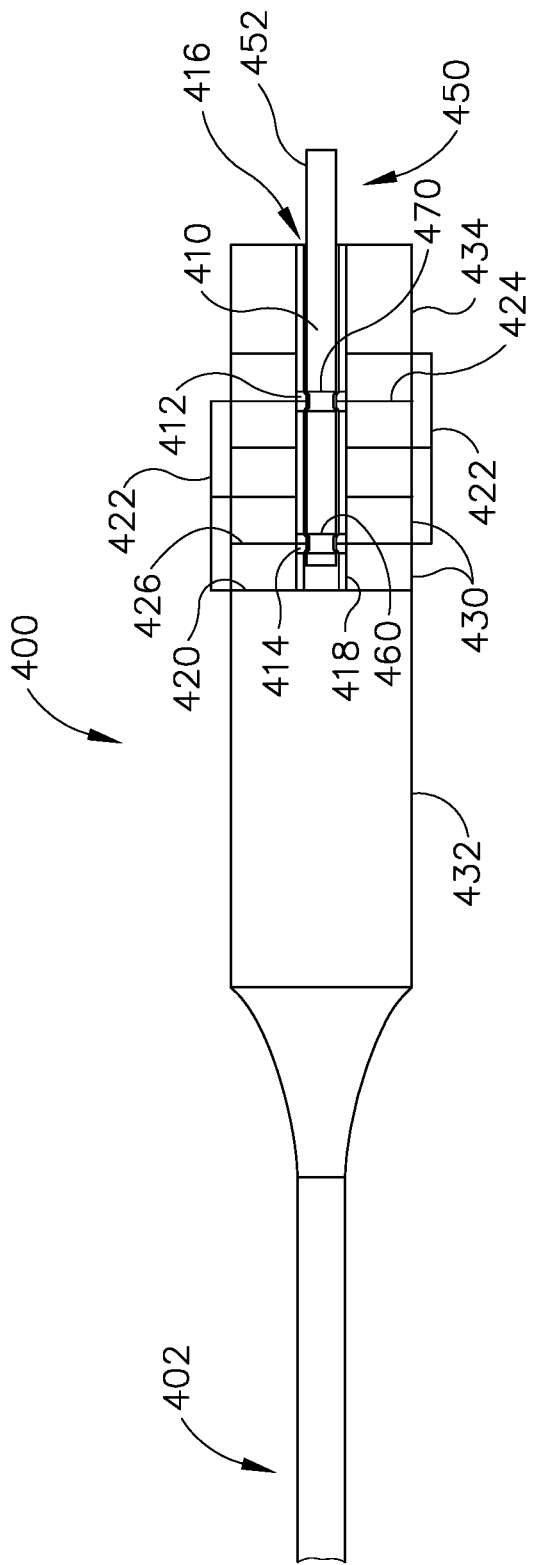
FIG. 6 depicts a side cross-sectional view of an exemplary rotatable electrical coupling assembly having an exemplary cable plug insertable into an exemplary transducer.

FIG. 6 depicts an exemplary transducer (400) with a central bolt (410) having a proximal aperture (416) configured to receive a cable plug (450) therein. Transducer (400) of the present example comprises a plurality of piezoelectric elements (430) that are compressed between a first resonator (432) and a second resonator (434) to form a stack of piezoelectric elements. Piezoelectric elements (430) may be fabricated from any suitable material, for example, lead zirconate-titanate, lead meta-niobate, lead titanate, and/or any suitable piezoelectric crystal material. A plurality of electrodes (420) are disposed between adjacent piezoelectric elements (430). In the present example, bridges (422) electrically couple alternating electrodes (420). Thus, when electrodes (420) are coupled to a power supply, a voltage potential is applied across the plurality of piezoelectric elements (430) via bridges (422). Bridges (422) may include an insulating material to prevent inadvertent electrical coupling of bridges (422) with the alternating electrodes (420) and/or other components, though this is merely optional. It should be understood that bridges (422) of the present example are merely exemplary and electrodes (420) may be electrically coupled through any other electrical connector as will be apparent to one of ordinary skill in the art in view of the teachings herein.

In the present example, a central bolt (410) extends longitudinally through central holes formed in each of the piezoelectric elements (430) and electrodes (420). Bolt (410) may comprise a non-conductive material or, in some versions, bolt (410) may comprise a conductive material with insulating material electrically isolating one or more electrodes (420) from bolt (410). In addition or in the alternative, a gap may be provided between the exterior of bolt (410) and the inner diameter of the central openings of piezoelectric elements (430). Central bolt (410) includes a longitudinally extending recess (418) formed therein and extending distally from a proximal aperture (416). As shown in FIG. 6, central bolt (410) forms a female socket configured to receive cable plug (450), as will be described in greater detail below. In the present example, a proximal electrode (424) is electrically coupled to a proximal detent (412) formed on central bolt (410) such that proximal electrode (424) is selectively electrically coupled to a proximal conductive portion (470) of cable plug (450). A distal electrode (426) is electrically coupled to a distal detent (414) formed on central bolt (410) such that distal electrode (426) is selectively electrically coupled to a distal conductive portion (460) of cable plug (450). Of course detents (412, 414) are merely exemplary and other features for central bolt (410) may be provided as will be apparent to one of ordinary skill in the art in view of the teachings herein. For instance, resiliently biased pins or balls, flexible tabs, conductive duck bill seals, etc. may be provided.

Cable plug (450) of the present example includes a body (452) having a distal conductive portion (460) and a proximal conductive portion (470). Conductive portions (460, 470) of the present example comprise annular recessed portions of cable plug (450) configured to receive and electrically couple to detents (412, 414). Distal conductive portion (460) is electrically coupled to a first wire (not shown) of a cable, such as cable (30), and proximal conductive portion (470) is electrically coupled to a second wire of the cable. The cable is coupled to a power supply such that the first and second wires transmit electrical power to conductors (460, 470). In some instances, cable plug (450) may be constructed in a similar manner to a stereo plug. As will be appreciated by one of ordinary skill in the art in view of the teachings herein, when cable plug (450) is inserted into recess (418) and the power supply is electrically coupled to detents (412, 414) via conductive portions (460, 470), electrodes (420) create a voltage potential across the plurality of piezoelectric elements (430) therebetween such that the plurality of piezoelectric elements (430) convert the electrical power into ultrasonic vibrations. Such ultrasonic vibrations are transmitted distally through a waveguide (402). Waveguide (402) may be coupled to a blade of an end effector (such as blade (82) of end effector (80)) such that the ultrasonic oscillation of the blade may simultaneously sever the tissue and denature the proteins in adjacent tissue cells, thereby providing a coagulative effect with relatively little thermal spread.

In the present example, the user may rotate transducer (400) and/or the end effector to sever tissue at a variety of orientations. When transducer (400) is rotated, conductive portions (460, 470) of cable plug (450) remain electrically coupled to detents (412, 414) such that transducer (400) remains electrically coupled to the power supply throughout the rotation. Other suitable arrangements and/or configurations for cable plug (450) and/or transducer (400) will be apparent to one of ordinary skill in the art in view of the teachings herein. For instance, a plurality of conductive portions (460, 470) may be formed on cable plug (450) to electrically couple each electrode (420). In such an arrangement, bridges (422) may be eliminated. Further still, cable plug (450) may be rotationally fixed relative to transducer (400). By way of example only, cable plug (450) may be mechanically secured to a handle assembly, such as handle assembly (60) described above, while transducer (400) is mounted therein by ball-bearing members that permit rotation of transducer (400) relative to the handle assembly.

D. Exemplary Electrode-based Electrical Coupling Assemblies

In some instances it may be preferable to utilize the electrodes of transducer (100) as part of the electrical coupling assembly. Utilizing the electrodes may reduce the number of components for transducer (100) while still permitting transducer (100) to be rotatable. In addition, the reduction in the number of parts may reduce the cost of producing transducer (100) and/or permit automated assembly of transducer (100) due to the integrated electrical coupling assembly. Accordingly, various examples of transducers utilizing electrodes as part of the electrical coupling assembly will now be described in greater detail.

i. Exemplary Electrodes with Outer Housing Stator

Figure 7:
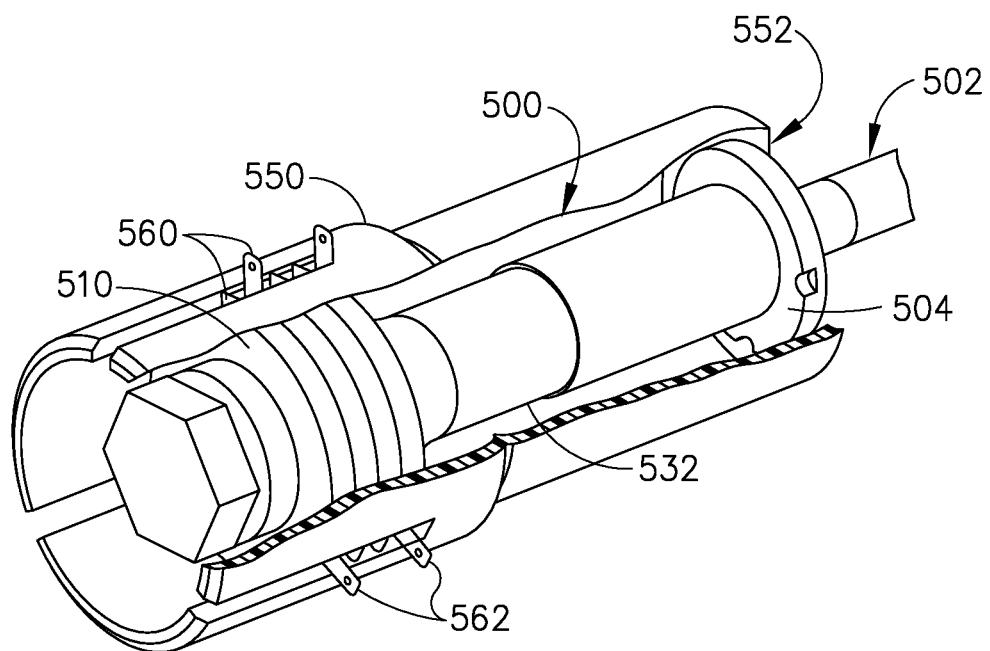
FIG. 7 depicts a perspective view of an exemplary rotatable electrical coupling assembly having enlarged electrodes electrically coupling to stator conductors of a stator casing.
Figure 8:
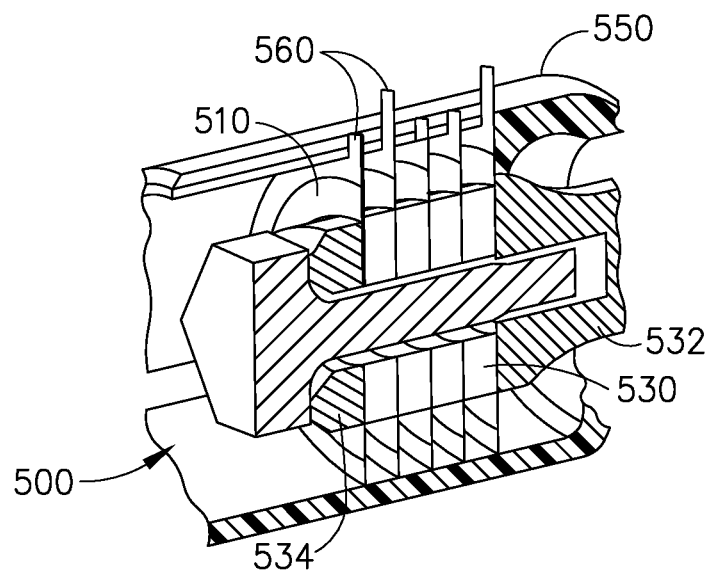
FIG. 8 depicts an enlarged partial perspective cross-sectional view of the rotatable electrical coupling assembly of FIG. 7 showing the electrically coupling of the electrodes to the stator conductors.

FIGS. 7-8 show an exemplary transducer (500) having a plurality of enlarged electrodes (510) extending circumferentially outwardly from transducer (500) and engaging with a plurality stator conductors (560) of a stator casing (550). Transducer (500) of the present example comprises a plurality of piezoelectric elements (530) that are compressed between a first resonator (532) and a second resonator (534) to form a stack of piezoelectric elements. Piezoelectric elements (530) may be fabricated from any suitable material, for example, lead zirconate-titanate, lead meta-niobate, lead titanate, and/or any suitable piezoelectric crystal material. As shown best in FIG. 8, electrodes (510) comprise conductive discs disposed between adjacent piezoelectric elements (530), each having a central opening to permit a central bolt to extend therethrough. When electrodes (510) are alternatingly coupled to the positive, or "hot," lead of a power supply and to the negative or ground, then a voltage potential is applied across the plurality of piezoelectric elements (530). Accordingly, the voltage potential across the plurality of piezoelectric elements (530) causes the plurality of piezoelectric elements (530) to convert the electrical power into ultrasonic vibrations. Such ultrasonic vibrations are transmitted distally through a waveguide (502). Waveguide (502) may be coupled to a blade of an end effector (such as blade (82) of end effector (80)) such that the ultrasonic oscillation of the blade may simultaneously sever the tissue and denature the proteins in adjacent tissue cells, thereby providing a coagulative effect with relatively little thermal spread. Transducer (500) of the present example further includes a horn flange (504) configured to abut a distal ledge (552) of stator casing (550), as will be described in more detail below. Horn flange (504) may further include a seal (not shown) to fluidly seal horn flange (504) to distal ledge (552).

Stator casing (550) comprises a plurality of stator conductors (560) configured to electrically couple to the plurality of electrodes (510). Stator casing (550) of the present example comprises a non-conductive material, such as plastic, though stator casing (550) may be insulated electrically using a diode circuit or any other electrical components, as will be apparent to one of ordinary skill in the art in view of the teachings herein. Stator casing (550) is configured to couple to a handle assembly, such as handle assembly (60), such that transducer (500) may be rotated relative to stator casing (550) while stator casing (550) does not rotate. Of course stator casing (550) may alternatively be secured to other components of the surgical instrument or stator casing (550) may be unsecured. Stator casing (550) further includes a distal ledge (552) configured to abut horn flange (504). In the present example, stator conductors (560) comprise flat conductive rings configured to abut and electrically couple to electrodes (510). As will be apparent to one of ordinary skill in the art in view of the teachings herein, distal ledge (552) abutting horn flange (504) and stator conductors (560) abutting electrodes (510) are positioned such that stator conductors (560) compress against electrodes (510). In some versions, one or more springs and/or other resilient members may be provided to compress stator conductors (560) against electrodes (510). Connector tabs (562) extend from stator conductors (560) and are configured to couple to a positive, or "hot," wire from a power supply or to a negative or ground wire. In the example shown in FIGS. 7-8, connector tabs (562) extend outwardly from stator casing (550) at predetermined orientations such that stator conductors (560) that are coupled to the positive wire of the power supply have connector tabs (562) oriented in a first direction while stator conductors (560) that are coupled to the negative wire of the power supply have connector tabs (562) oriented in a second direction. Of course connector tabs (562) are merely optional and the wires from the power supply may instead be directly coupled to stator conductors (560). Alternatively, jumper wires may be provided to electrically couple corresponding stator conductors (560).

In the present example, the user may rotate transducer (500) and/or the end effector to sever tissue at a variety of orientations. When transducer (500) is rotated, electrodes (510) remain electrically coupled to stator conductors (560) throughout the rotation of transducer (500). Thus, electrodes (510) of transducer (500) may be used as part of the rotational electrical coupling assembly that maintains the electrical connection between transducer (500) and the power supply. Other suitable configurations for stator casing (550), stator conductors (560), and/or transducer (500) will be apparent to one of ordinary skill in the art in view of the teaching herein.

ii. Exemplary Waved Electrodes

Figure 9:
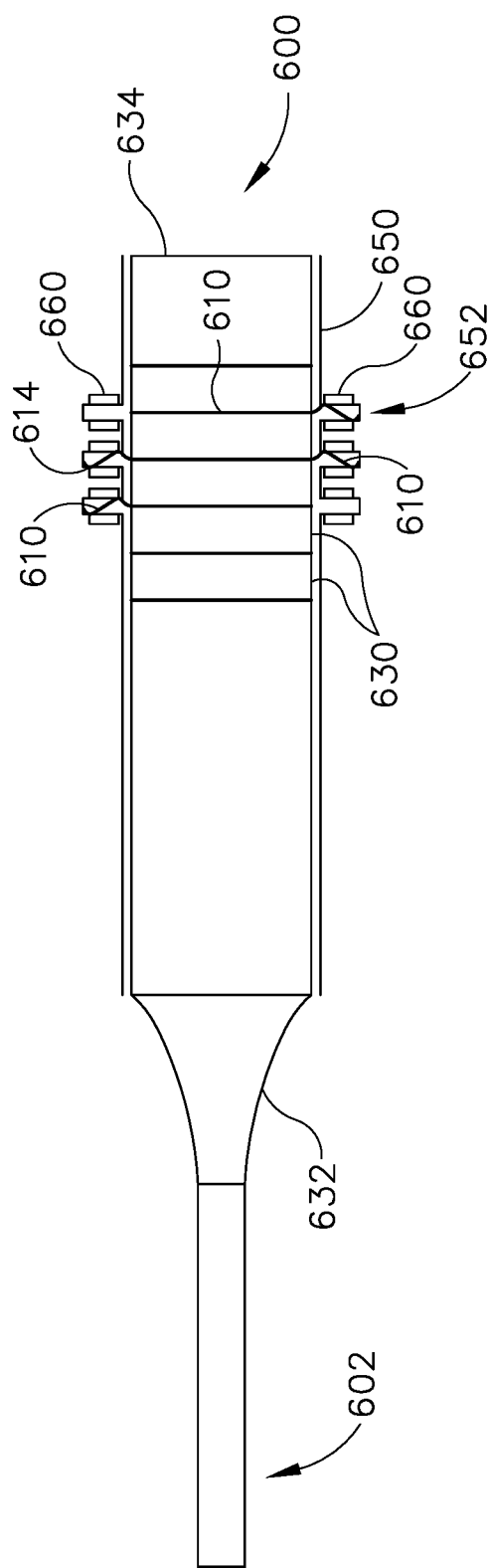
FIG. 9 depicts a side cross-sectional view of an exemplary rotatable electrical coupling assembly having waved electrodes.
Figure 10:
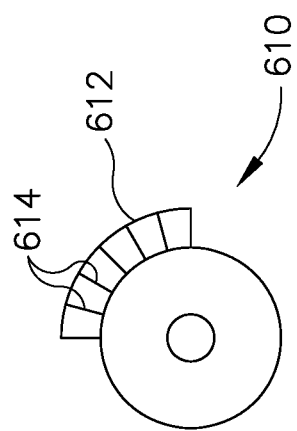
FIG. 10 depicts a front elevation view of an exemplary waved electrode for the rotatable electrical coupling assembly of FIG. 9.

FIGS. 9-10 depict an alternative transducer (600) having a plurality of waved electrodes (610) extending outwardly from transducer (600) and engaging with one or more conductors (660) within channels (652) of a stator casing (650). Transducer (600) of the present example comprises a plurality of piezoelectric elements (630) that are compressed between a first resonator (632) and a second resonator (634) to form a stack of piezoelectric elements. Piezoelectric elements (630) may be fabricated from any suitable material, for example, lead zirconate-titanate, lead meta-niobate, lead titanate, and/or any suitable piezoelectric crystal material. Waved electrodes (610) are disposed between piezoelectric elements (630), and each waved electrode (610) includes a central opening configured to permit a central bolt to extend therethrough. While only some of the electrodes of transducer (600) are shown as waved electrodes (610), it should be understood that all of the electrodes of transducer (600) may comprise waved electrodes (610), though this is merely optional. Waved electrodes (610) are alternatingly coupled to a positive, or "hot," lead of a power supply and to a negative or ground. A voltage potential is thereby applied across the plurality of piezoelectric elements (630). The voltage potential across the plurality of piezoelectric elements (630) causes the plurality of piezoelectric elements (630) to convert the electrical power into ultrasonic vibrations. Such ultrasonic vibrations are transmitted distally through a waveguide (602). Waveguide (602) may be coupled to a blade of an end effector (such as blade (82) of end effector (80)) such that the ultrasonic oscillation of the blade may simultaneously sever the tissue and denature the proteins in adjacent tissue cells, thereby providing a coagulative effect with relatively little thermal spread.

As shown best in FIG. 10, waved electrodes (610) comprise conductive discs having an arcuate portion (612) extending outwardly from a central axis of electrodes (610). Arcuate portion (612) comprises a plurality of ridges (614) forming a non-flat or wavy surface. By way of example only, ridges (614) may be radial ridges extending outwardly and configured in similar manner to the ridges of a bottle cap. In other versions, ridges (614) may be circumferentially oriented ridges. Ridges (614) are configured to contact conductors (660) such that electrodes (610) are electrically coupled to conductors (660) when arcuate portion (612) is inserted into channels (652). As shown in FIG. 10, arcuate portion (612) comprises a 90 degree arc of ridged material, though this is merely optional. In some versions, arcuate portion (612) may comprise an arc of ridges (614) less than 90 degrees or more than 90 degrees. For instance, arcuate portion (612) may extend 360 degrees about each electrode (610) to form a continuous ridged disc.

Referring back to FIG. 9, stator casing (650) comprises a plurality of channels (652) having a conductor (660) contained within each channel (652). In some versions, conductors (660), channels (652), and stator casing (650) may comprise molded interconnect devices ("MIDs"), though this is merely optional. In the present example, channels (652) are sized to receive arcuate portion (612) of a corresponding electrode (610) therein. In some versions channels (652) may be sized smaller than ridges (614) of arcuate portions (612) such that ridges (614) are compressed within channels (652). Such compression of ridges (614) may maintain the electrical coupling of arcuate portions (612) with conductors (660) of each channel (652). Conductors (660) are coupled to a corresponding wire of a power supply such that electrical power is supplied to electrodes (610) to create a voltage potential across the piezoelectric elements (630) of transducer (600). Similar to stator casing (550) described above, stator casing (650) of the present example is secured to a handle assembly, such as handle assembly (60), such that transducer (600) may rotate relative to stator casing (650). Of course stator casing (650) may alternatively be secured to other components of the surgical device or stator casing (650) may be unsecured. Still other configurations for stator casing (650) will be apparent to one of ordinary skill in view of the teachings herein.

In the present example, the user may rotate transducer (600) and/or the end effector to sever tissue at a variety of orientations. When transducer (600) is rotated, electrodes (610) rotate and remain electrically coupled to conductors (660) within channels (652) via arcuate portions (612). Thus, electrodes (610) of transducer (600) may be used as part of the rotational electrical coupling assembly that maintains the electrical power connection between transducer (600) and the power supply. Other suitable configurations for stator casing (650), electrodes (610), and/or transducer (600) will be apparent to one of ordinary skill in the art in view of the teaching herein.

E. Exemplary Proximal Mounted Electrical Coupling Assemblies

In some instances it may be preferable to provide the rotatable electrical coupling assembly at a proximal end of transducer (100) or integrated into a distal end of cable (30). Such a configuration may be preferable if there is limited room in surgical instrument (50) at a distal end of transducer (100).

i. Exemplary Proximally Mounted Pancake Slip Ring Connector Assembly

Figure 11:
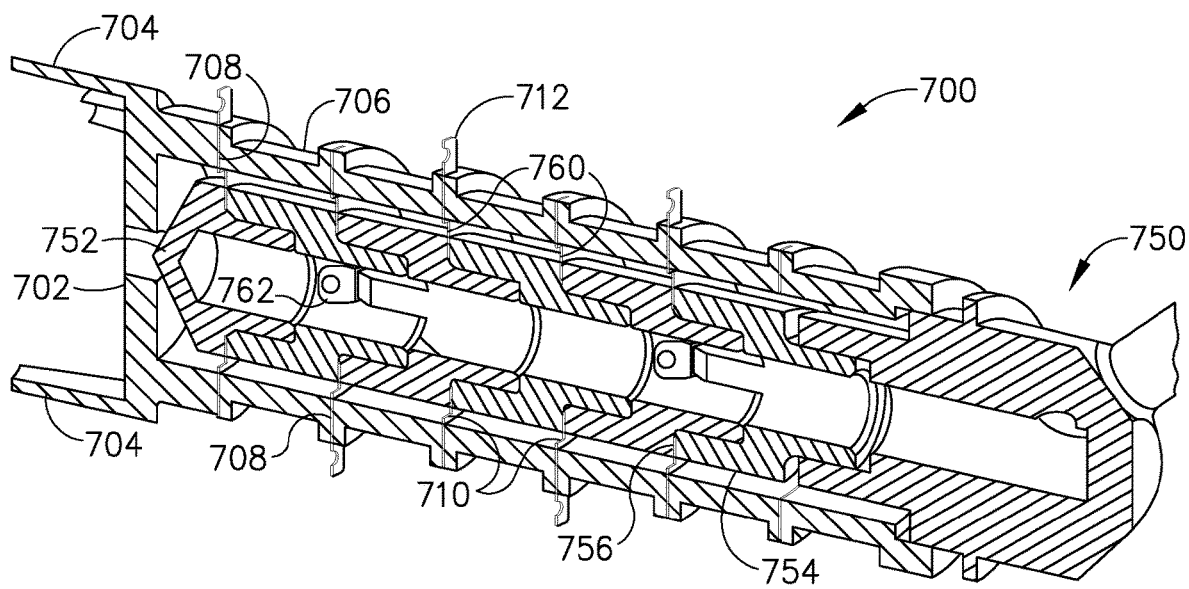
FIG. 11 depicts a perspective cross-sectional view of an exemplary rotatable electrical coupling assembly having an outer housing assembly and an inner stator assembly configured to form a plurality of pancake slip ring assemblies.
Figure 12:
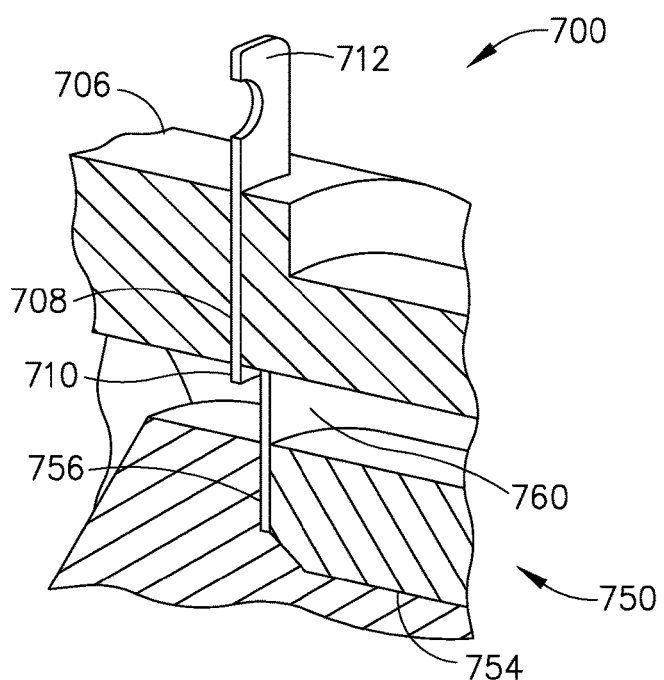
FIG. 12 depicts an enlarged perspective cross-sectional view of the rotatable electrical coupling assembly of FIG. 11 showing an outer rotor disc electrically coupling to an inner stator disc.

FIGS. 11-12 depict a rotatable outer housing assembly (700) having a plurality of outer rotor discs (710) configured to electrically couple to a plurality of inner stator discs (760) mounted to an inner stator assembly (750). Outer housing assembly (700) of the present example comprises a distal wall (702) having a plurality of members (704) configured to couple outer housing assembly (700) to a proximal end of a transducer. Members (704) are configured to secure outer housing assembly (700) to the transducer such that when the transducer is rotated, outer housing assembly (700) also rotates. Members (704) of the present example comprise resilient plastic fingers configured to selectively couple to a head of a bolt of the transducer such that rotation of the transducer (and therefore the bolt) also rotates outer housing assembly (700) via members (704). Outer housing assembly (700) further includes a main body portion (706) having a plurality of recesses (708) configured to receive outer rotor discs (710) therein. In some versions, main body portion (706) may comprise one or more clamshell portions that couple together to secure inner stator assembly (750) therein, though this is merely optional. As best seen in FIG. 12, outer rotor discs (710) comprise conductive discs configured to electrically couple to inner stator discs (760) when inner stator discs (760) are compressed against outer rotor discs (710), thereby forming a pancake slip ring assembly. Outer rotor discs (710) further include connectors (712) that are electrically coupled to one or more electrodes of the transducer, such as electrodes (232) disposed between piezoelectric elements (230) described above. As shown in FIG. 11, connectors (712) are located on alternating sides of main body portion (706) and are configured to correspond to a positive, or "hot," lead and to a negative or ground lead.

Inner stator assembly (750) comprises a distal mandrel (752) and a main body portion (754). Main body portion (754) includes a plurality of inner stator discs (760) mounted to main body portion (754) via channels (756). In the present example, inner stator discs (760) comprise conductive discs configured to compress against and electrically couple to outer rotor discs (710). Distal mandrel (752) is configured to abut distal wall (702) to provide a force to compress inner stator discs (760) against outer rotor discs (710). Inner stator discs (760) further include inner connectors (762) that are electrically coupled to a positive and/or a negative wire from a cable, such as cable (30), to provide electrical power to inner stator discs (760). Thus, inner stator discs (760) are configured to provide electrical power to the electrodes of a transducer via the rotatable pancake slip ring formed with outer rotor discs (710).

Using the present outer rotor assembly (700) and inner stator assembly (750), the user may rotate transducer (700) and/or the end effector relative to inner stator assembly (750) to a variety of angles to sever tissue at a variety of orientations. When the transducer is rotated (and therefore outer rotor assembly (700) is rotated via members (704)), the electrodes of the transducer remain electrically coupled to the power supply via the pancake slip ring assembly formed by the electrical coupling assembly of outer rotor discs (710) and inner stator discs (760). Other suitable configurations for outer rotor assembly (700) and/or inner stator assembly (750) will be apparent to one of ordinary skill in the art in view of the teaching herein. For instance, in some versions, outer rotor assembly (700) may be coupled to the cable while inner stator assembly (750) is coupled to the transducer and electrodes.

ii. Exemplary Spring-biased Pancake Slip Ring Connector Assembly

Figure 13:
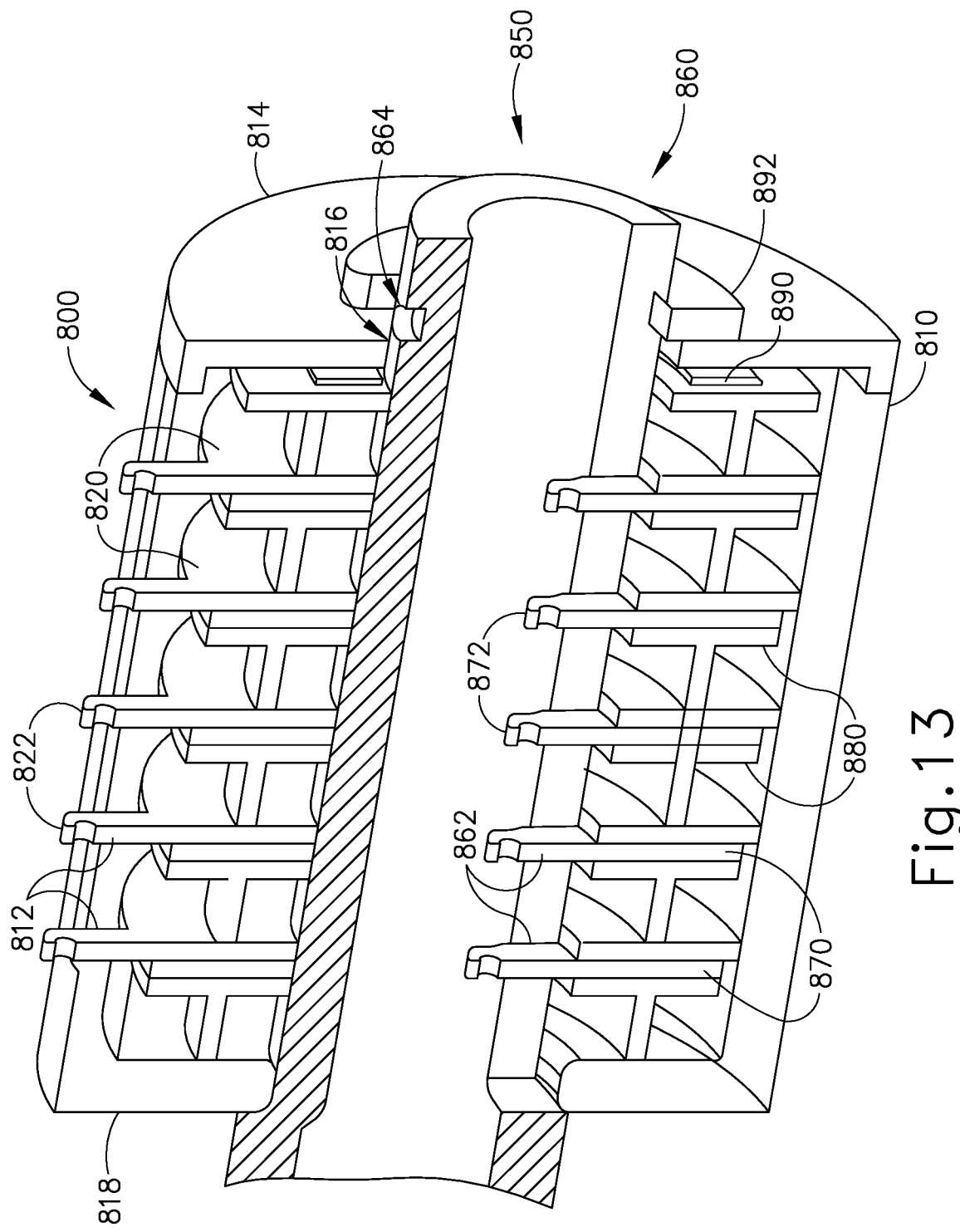
FIG. 13 depicts a perspective cross-sectional view of an exemplary alternative rotatable electrical coupling assembly having an outer housing assembly and an inner stator assembly configured to form a plurality of pancake slip ring assemblies.

An exemplary alternative outer rotor assembly (800) and inner stator assembly (850) are shown in FIG. 13. In this example, outer rotor assembly (800) comprises an outer housing (810) having a plurality of slots (812) configured to receive tabs (822) of a plurality of outer rotor discs (820). Outer housing (810) of the present example is coupled to and rotates with a transducer (not shown) at a distal end (818) of outer housing (810). In some versions, outer housing (810) is secured via distal wall (818) to a proximal end of the transducer, though this is merely optional. In other versions, outer housing (810) is integrally formed with the transducer, such as to the transducer casing (not shown), to form a homogeneous continuum of material. Outer housing (810) also includes a proximal end wall (814) having a proximal aperture (816) configured to permit a portion of inner mandrel (860) to extend therethrough. Outer rotor discs (820) comprise conductive discs having outwardly extending tabs (822) that insert into slots (812) of outer housing (810). Accordingly, when outer housing (810) is rotated, outer rotor discs (820) also rotate via tabs (822). Tabs (822) are further configured to electrically couple to the electrodes of the transducer such that electrical power supplied to outer rotor discs (820) is transmitted to corresponding electrodes of the transducer. Outer rotor discs (820) of the present example are configured to electrically couple to inner stator discs (870) of inner stator assembly (850) thereby forming a pancake slip ring connection.

Inner stator assembly (850) comprises an inner mandrel (860) having a plurality of slots (862) configured to receive inwardly extending tabs (872) from a plurality of inner stator discs (870). Inner mandrel (860) is further configured to receive a cable, such as cable (30), such that the wires of the cable electrically couple to tabs (872) extending into inner mandrel (860). In the present example, inner stator discs (870) are mechanically coupled to inner mandrel (860) via the insertion of tabs (872) into slots (862). Thus, if inner mandrel (860) is rotationally secured, such as being secured to handle assembly (60) and/or cable (30), then inner stator discs (870) are likewise rotationally secured. Accordingly, outer rotor assembly (800) (and therefore the transducer) may be rotated relative to inner stator assembly (850) while inner stator assembly (850) does not rotate.

Inner stator discs (870) of the present example comprise conductive discs disposed about inner mandrel and configured to electrically couple to outer rotor discs (820) to form pancake slip ring assemblies. In the present example, a plurality of insulating annular spacers (880) are located between each pancake slip ring assembly. As shown in FIG. 13, a distal-most annular spacer (880) abuts distal wall (818) of outer housing (810) and a proximal-most annular spacer (880) abuts a wave spring (890). Wave spring (890) is secured against proximal-most annular spacer (880) via proximal end wall (814) of outer casing (810). In the present example, a retaining clip (892) is coupled to inner mandrel (860) via an annular channel (864) formed in a portion of inner mandrel (860) that extends proximally of proximal end wall (814). Thus, retaining clip (892) prevents proximal translation of proximal end wall (814) of outer casing (810) by "sandwiching" outer casing (810) between the proximal end of the transducer and retaining clip (892). Accordingly, with the proximal end of wave spring (890) secured via proximal end wall (814), the distal end of wave spring (890) compresses inner stator discs (870), outer rotor discs (820), and annular spacers (880) together and against distal wall (818) of outer casing (810). Such compression may further ensure inner stator discs (870) and outer rotor discs (820) are electrically coupled. In some versions, inner stator discs (870) and/or outer rotor discs (820) may further comprise ridging or bumps to further ensure electrical coupling of inner stator discs (870) with outer rotor discs (820).

In the present example, when electrical power is supplied via the cable and tabs (872), inner stator discs (870) transmit the electrical power to outer rotor discs (820). The electrical power is further transmitted from outer rotor discs (820) to the electrodes of the transducer. Thus, even when the transducer (and therefore the outer rotor assembly (800)) is rotated by the user, electrical power is continuously supplied from the cable to the electrodes of the transducer throughout the rotation. Other suitable configurations for outer rotor assembly (800) and inner stator assembly (850) will be apparent to one of ordinary skill in the art in view of the teachings herein.

iii. Exemplary Threaded Cable Connector Assembly

FIGS. 14-15 depict an exemplary threaded connector assembly (900) comprising a cable end (910) configured to thread into a complementary threaded recess (960) formed in a member (952) coupled to a proximal end of a transducer (950). Cable end (910) of the present example comprises a threaded end (920) and a plurality of wires (930) extending distally from cable end (910). Wires (930) are electrically coupled to electrodes (not shown) of transducer (950). Accordingly, electrical power supplied through cable end (910) is transmitted to the electrodes of transducer (950) via wires (930). In the present example, wires (930) are further configured to have a length such that threaded end (920) of cable end (910) may be substantially unthreaded from threaded recess (960) while wires (930) remain coupled to the electrodes of transducer (950). In the example shown in FIG. 15, cable end (910) also includes ledges (912) configured to insert into slots (not shown) of a handle assembly (not shown). Accordingly, when transducer (950) is rotated within the handle assembly, cable end (910) is rotationally secured within the slots via ledges (912) while cable end (910) is permitted to translate proximally or distally in response to the threading of cable end (910) into or out of threaded recess (960).

In the example shown in FIG. 14, wires (930) are further configured such that wires (930) are substantially untwisted when cable end (910) is threaded to a middle point of threaded recess (960). Accordingly, when transducer (950) is rotated in a first direction, cable end (910) threads into threaded recess (960) towards a distal-most position of threaded recess (960) and wires (930) twist for a predetermined amount of windings. When transducer (950) is rotated a second direction, opposite to the first direction, cable end (910) unthreads from threaded recess (960) towards a proximal-most position of threaded recess (960) and wires (930) twist in the opposite direction for a predetermined amount of windings. A broken thread (not shown) at a proximal end of threaded recess (960) prevents cable end (910) from decoupling from threaded recess (960), though this is merely optional.

When a user initially desires to use the surgical instrument having threaded connector assembly (900), initially the user rotates transducer (950) until cable end (910) is threaded to a middle point, or zero point, of threaded recess (960). Accordingly, during a surgical procedure, the user may rotate transducer (950) a predetermined rotations until threaded end (920) of cable end (910) is fully threaded into threaded recess (960) or until threaded end (920) encounters the broken thread at the proximal end of threaded recess (960). It should be understood that the number of predetermined rotations are determined by the number of threads on threaded end (910) and in threaded recess (960). By way of example only, threaded recess (960) shown in FIG. 14 includes ten threads such that transducer (950) may be rotated five rotations from the zero point in a first direction and five rotations in the opposite direction. Of course any number of threads may be provided. Furthermore, threaded connector assembly (900) may have other configurations as will be apparent to one of ordinary skill in the art in view of the teachings herein.

F. Exemplary Ball Bearing Electrical Coupling Assemblies

Figure 16:
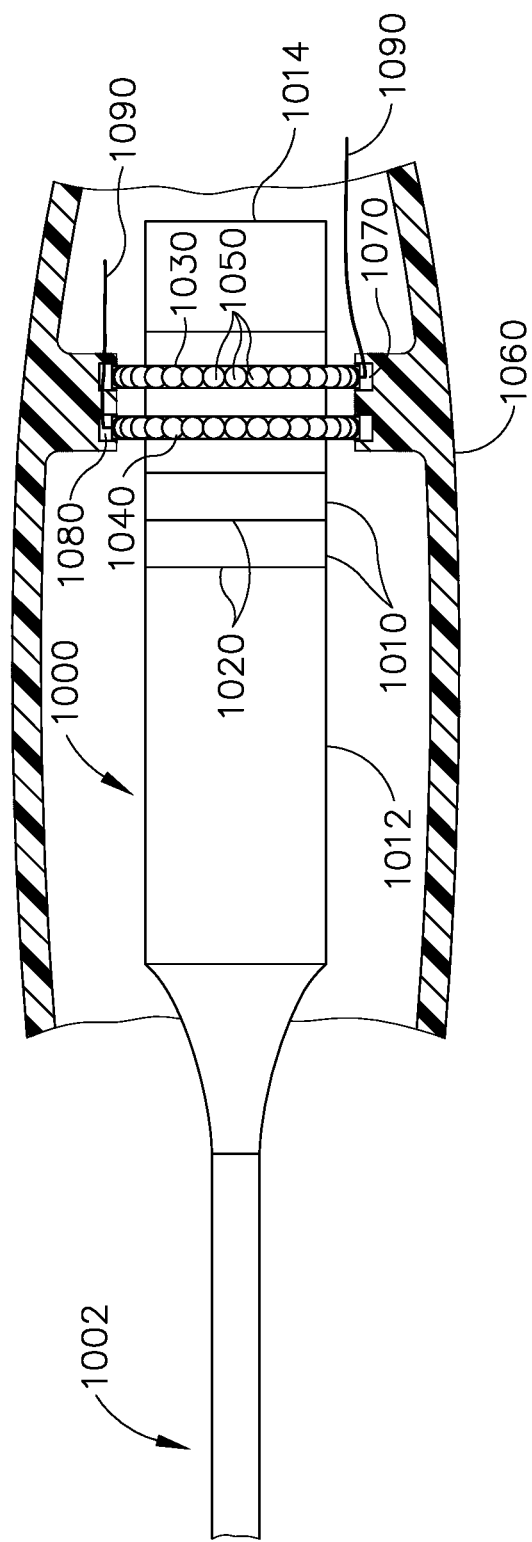
FIG. 16 depicts a side elevation view of an exemplary rotatable electrical coupling assembly having a plurality of ball bearings electrically coupled to the electrodes of a transducer.

FIG. 16 depicts an exemplary alternative transducer (1000) having a ball bearings (1050) to electrically couple transducer (1000) to wires (1090) in a casing (1060) (a portion of which has been omitted to show ball bearings (1050)). Transducer (1000) of the present example comprises a plurality of piezoelectric elements (1010) that are compressed between a first resonator (1012) and a second resonator (1014) to form a stack of piezoelectric elements.

Piezoelectric elements (1010) may be fabricated from any suitable material, for example, lead zirconate-titanate, lead meta-niobate, lead titanate, and/or any suitable piezoelectric crystal material. A plurality of electrodes (1020) are disposed between adjacent piezoelectric elements (1010). In the present example, bridges (not shown) electrically couple alternating electrodes (1020). The bridges may further include an insulating material to prevent inadvertent electrical coupling of the bridges with the alternating electrodes (1020) and/or other components. It should be understood that the bridges of the present example are merely exemplary and electrodes (1020) may be electrically coupled through any other electrical connector as will be apparent to one of ordinary skill in the art in view of the teachings herein. Merely exemplary alternative electrical connectors may include conductive traces (such as those of a printed computer board or PCB) formed in a casing of transducer. Referring back to the present example, when electrodes (1020) are coupled to a power supply, a voltage potential is applied across the plurality of piezoelectric elements (1010) via the bridges. The voltage potential across the plurality of piezoelectric elements (1010) causes the plurality of piezoelectric elements (1010) to convert the electrical power into ultrasonic vibrations. Such ultrasonic vibrations are transmitted distally through a waveguide (1002). Waveguide (1002) may be coupled to a blade of an end effector (such as blade (82) of end effector (80)) such that the ultrasonic oscillation of the blade may simultaneously sever the tissue and denature the proteins in adjacent tissue cells, thereby providing a coagulative effect with relatively little thermal spread.

In the present example, transducer (1000) further includes a first lower annular trough (1030) and a second lower annular trough (1040). Lower annular troughs (1030, 1040) are configured to receive ball bearings (1050) therein. A portion of an electrode (1020) is exposed within each lower trough (1030, 1040) such that ball bearings (1050) contact and electrically couple to the respective electrode (1020). In some versions, a conductor (not shown) may be electrically coupled to each electrode (1020) and positioned within a corresponding lower trough (1030, 1040) to further aid the electrical coupling of ball bearings (1050) to electrodes (1020). Ball bearings (1050) are secured within lower troughs (1030, 1040) via an annular casing (1060) having complementary upper annular troughs (1070, 1080). Wires (1090) are inserted through casing (1060) such that an end of each wire (1090) is exposed within a corresponding upper trough (1070, 1080) to electrically couple to the ball bearings (1050). In some versions, a conductor (not shown) may be electrically coupled to each wire (1090) and positioned within a corresponding upper trough (1070, 1080). Accordingly, when a power supply is coupled to wires (1090), ball bearings (1050) transmit the electrical power to electrodes (1020), thereby providing electrical power to transducer (1000). As will be apparent to one of ordinary skill in the art in view of the teachings herein, transducer (1000) may be rotated relative to casing (1060) while the electrical power is still supplied to transducer (1000) via ball bearings (1050). In some versions, an electrically conductive lubricant may be added to troughs (1030, 1040, 1070, 1080) to enhance the electrical coupling of ball bearings (1050) to electrodes (1020) and wires (1090). Other suitable configurations for transducer (1000) having ball bearings (1050) will be apparent to one of ordinary skill in the art in view of the teachings herein.

Figure 17:
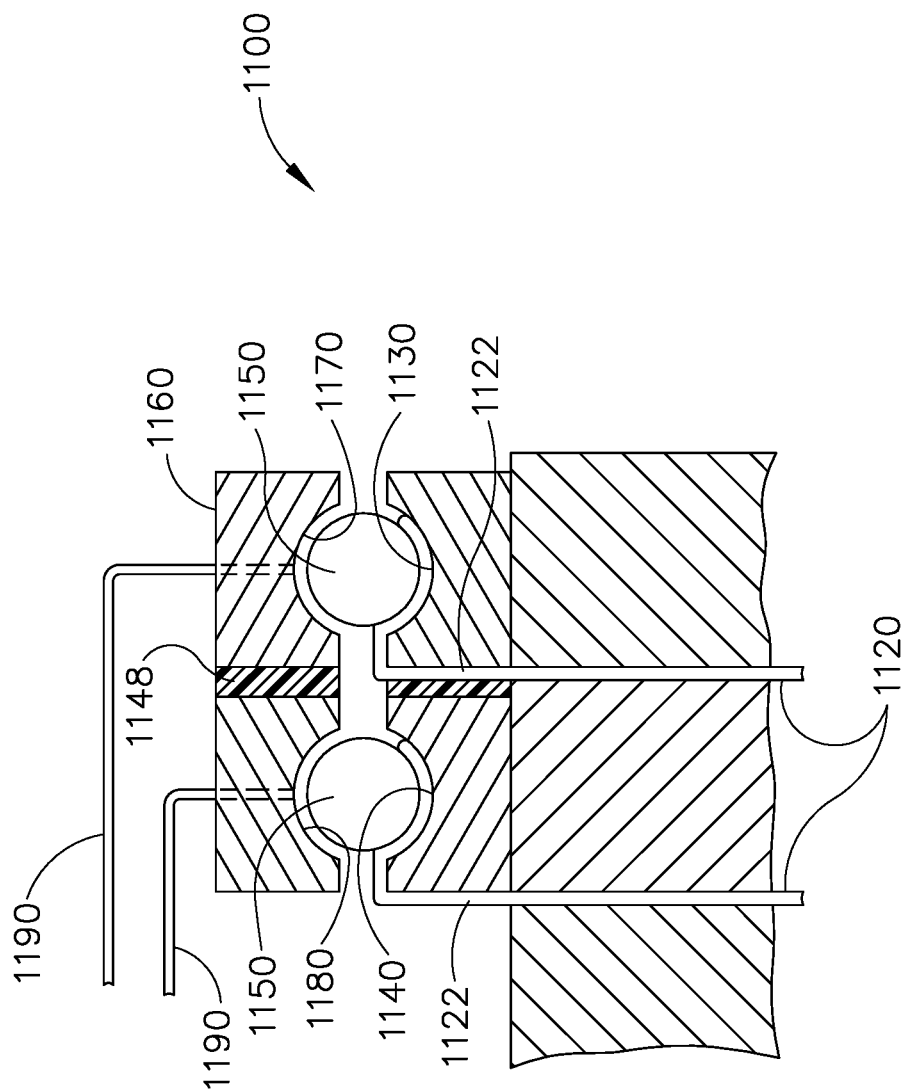
FIG. 17 depicts an enlarged partial side cross-sectional view of an exemplary alternative rotatable electrical coupling assembly showing a pair of ball bearings in troughs and having wires electrically coupling the ball bearings to the electrodes of a transducer.

One merely exemplary alternative configuration for a transducer (1100) having ball bearings (1150) is shown in FIG. 17. In such a configuration, lower troughs (1130, 1140) are formed on an outer surface of transducer (1100) and a pair of wires (1122) extend from electrodes (1120) into lower troughs (1130, 1140). In the present example, an insulator (1148) is provided between each bearing assembly to electrically isolate the bearing assemblies from each other. Casing (1160) of the present example retains ball bearings (1150) within troughs (1130, 1140) and may be constructed in accordance with at least some of the teachings of casing (1060) described above. A pair of wires (1190) are electrically coupled to ball bearings (1150) via upper troughs (1170, 1180) formed in casing (1160). Thus, when a power supply is coupled to wires (1190), the electrical power is transmitted to electrodes (1120) via ball bearings (1150). Accordingly, transducer (1100) may be rotated relative to casing (1160) while still maintaining an electrical connection with the power supply.

Figure 18:
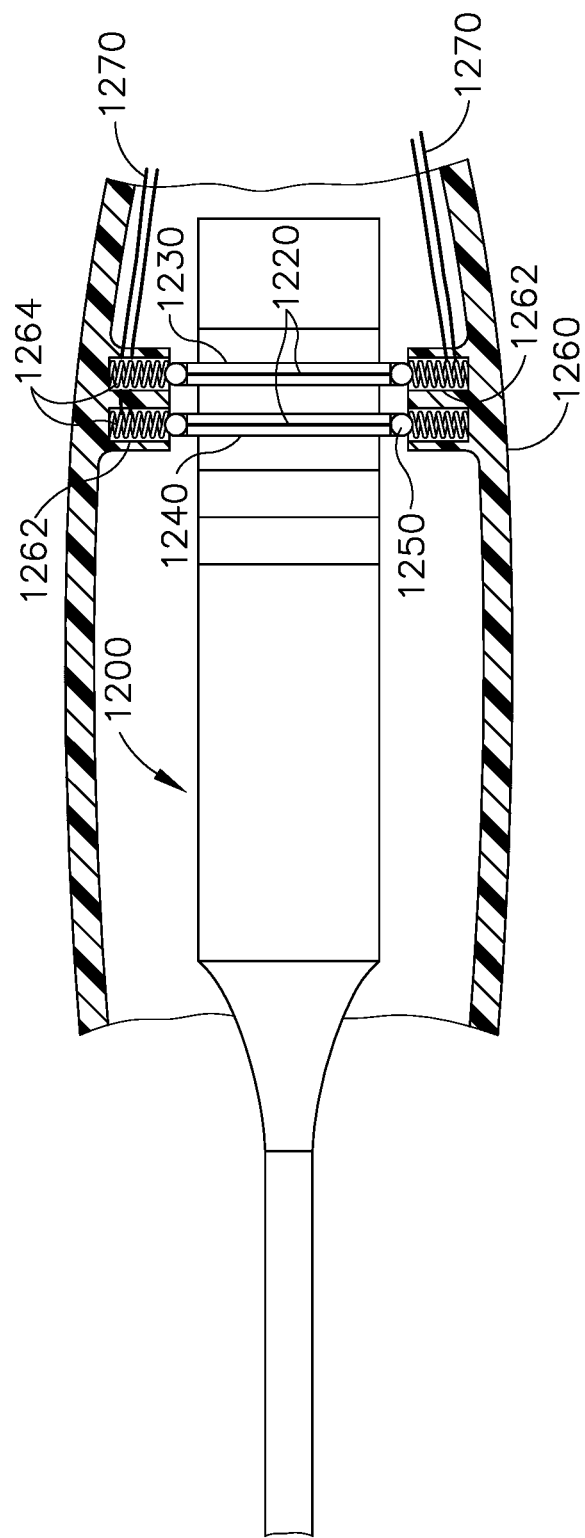
FIG. 18 depicts a side cross-sectional view of an exemplary alternative rotatable electrical coupling assembly having spring-biased ball bearings electrically coupling to electrodes in troughs.

FIG. 18 depicts yet a further exemplary alternative configuration for a transducer (1200) having ball bearings (1250) electrically coupled to electrodes (1220). Transducer (1200) of the present example is configured in substantially the same manner as transducer (1000) described above. Transducer (1200) includes a pair of annular lower troughs (1230, 1240) having exposed electrodes (1220) therein. In the present example, casing (1260) comprises an annular member having a pair of recesses (1262) formed on opposite sides of casing (1260). In the example shown in FIG. 18, recesses (1262) include a pair of resilient springs (1264) configured to urge ball bearings (1250) into troughs (1230, 1240). Wires (1270) are coupled to springs (1264) such that when a power supply is coupled wires (1270), springs (1264) and ball bearings (1250) transmit the electrical power to electrodes (1220), thereby providing electrical power to transducer (1200). As will be apparent to one of ordinary skill in the art in view of the teachings herein, transducer (1200) may be rotated relative to casing (1260) while power is still supplied to transducer (1200) via ball bearings (1250). In some versions, an electrically conductive lubricant may be added to troughs (1230, 1240) to enhance the electrical coupling of ball bearings (1250) to electrodes (1220) and wires (1270).

Of course other configurations for transducer (1200) will be apparent to one of ordinary skill in the art in view of the teachings herein. For instance, in some versions resiliently biased pogo pins may be used instead of ball bearings (1250). Further still, troughs (1230, 1240) may be omitted and a conductor or flexible circuit may be coupled to the exterior of transducer (1200) such that the pogo pins engage and electrically couple to the conductor or flexible circuit.

G. Exemplary Drum Slip Ring Electrical Coupling Assemblies

In some versions, it may be preferable to provide an electrical coupling assembly about a distal end of transducer (100), such as at a horn portion of transducer (100). For instance, an electrical coupling assembly on a distal end of transducer (100) may permit the length of the handle assembly to be shortened, thereby reducing the overall size and bulk of the surgical instrument. Further still, including the electrical coupling assembly at or near the distal end of transducer (100) may provide a counter weight to cable (30) attached at the proximal end of transducer (100), thereby providing additional longitudinal balance to the surgical instrument. Accordingly, various annular assemblies disposed about a distal portion of transducer (100) will now be described in greater detail.

i. Exemplary Drum Slip Ring Assembly with a Tube Collar Cap

Figure 19:
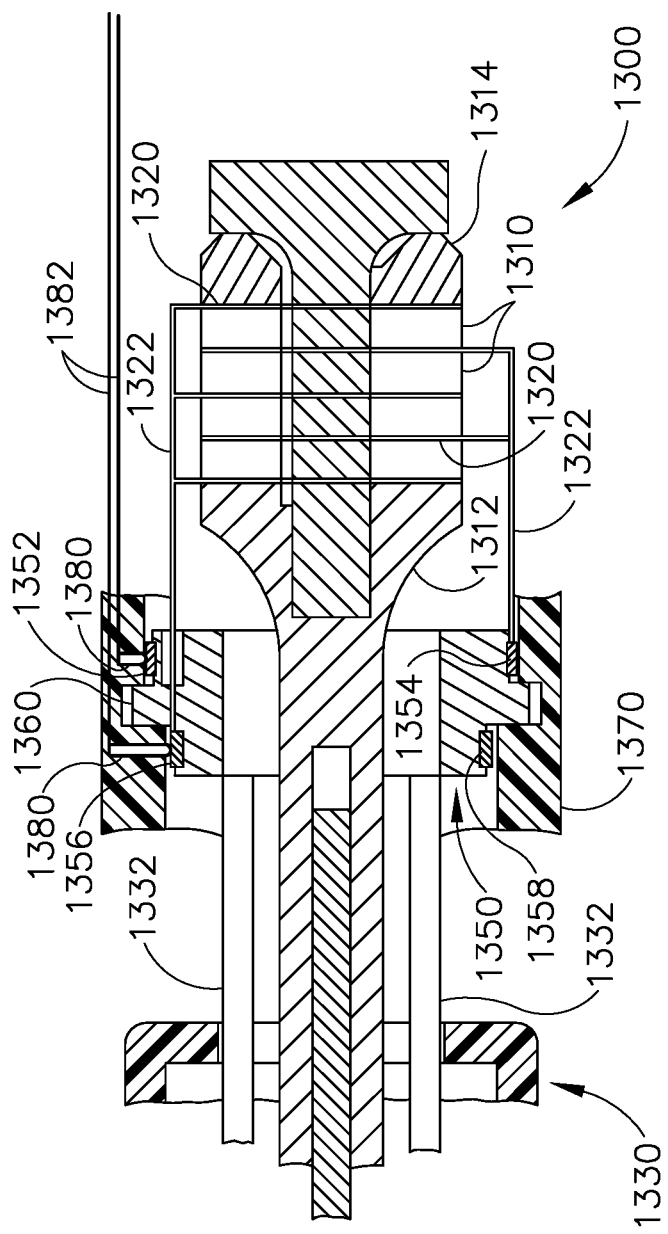
FIG. 19 depicts a side cross-sectional view of yet another exemplary rotatable electrical coupling assembly having a rotatable drum electrically coupled to pogo pins.

FIG. 19 depicts an exemplary transducer (1300) electrically coupled to a drum (1350) disposed about a distal portion of transducer (1300). Transducer (1300) of the present example comprises a plurality of piezoelectric elements (1310) that are compressed between a first resonator (1312) and a second resonator (1314) to form a stack of piezoelectric elements. Piezoelectric elements (1310) may be fabricated from any suitable material, for example, lead zirconate-titanate, lead meta-niobate, lead titanate, and/or any suitable piezoelectric crystal material. A plurality of electrodes (1320) are disposed between adjacent piezoelectric elements (1310) such that a voltage gradient may be applied across piezoelectric element (1310) contained therebetween. Accordingly, when the voltage gradient is applied across piezoelectric element (1310), piezoelectric element (1310) converts the electrical energy into oscillating mechanical energy. In the present example, the plurality of electrodes (1320) are coupled to drum (1350) via wires (1322).

A tube collar cap (1330) is coupled to a distal portion of transducer (1300) and is configured such that when transducer (1300) is rotated, tube collar cap (1330) also rotates. By way of example only, tube collar cap (1330) may be coupled to transducer (1300) via threading, adhesives, set screws, integral formation, and/or otherwise. A pair of cylindrical rails (1332) extend proximally from tube collar cap (1330) and rails (1332) are configured to couple to and carry drum (1350) thereon. Accordingly, as will be apparent to one of ordinary skill in the art in view of the teachings herein, when transducer (1300) and tube collar cap (1330) are rotated, drum (1350) also rotates via rails (1332). In the assembly shown, rails (1332) insert into holes (not shown) formed in drum (1350). In the present example, rails (1332) and drum (1350) are sized and configured such that drum (1350) does not contact transducer (1300), yet drum (1350) still rotates with transducer (1300). It should be understood that this is merely optional, and in other configurations, drum (1350) may be in contact with or coupled to transducer (1300). It should also be understood that tube collar cap (1330) and/or other rotatable components may be supported in handle assembly (60) by bearings, etc.

Drum (1350) comprises a rotatable tubular member having a first annular conductive portion (1352) on a first circumferential surface (1354) and a second annular conductive portion (1356) on a second circumferential surface (1358). Drum (1350) of the present example comprises a plastic body, though other materials, including metals, composites, insulated metals, ceramics, etc. may be used as well. In the present example, conductive portions (1352, 1356) are manufactured with drum (1350) using Molded Interconnect Device ("MID") technology. In some versions, conductive portions (1352, 1356) may be formed by drawing a piece of conductive material to form a continuous surface or, in other versions, a strip of conductive material may be wrapped around to form a ring of conductive material. It should be understood that annular conductive portions (1352, 1356) are merely exemplary and any other cylindrical or substantially cylindrical conductive member may be disposed about circumferential surfaces (1354, 1358). For instance, in some versions resilient leaf springs, such as beryllium-copper leaf springs, may be disposed about drum (1350). Moreover, while conductive portions (1352, 1356) are shown on the exterior of drum (1350), it should be understood that conductive portions (1352, 1356) may be formed on any surface or combination of surfaces of drum (1350). By way of example only, conductive portions (1352, 1356) may be formed on a distal face of drum (1350), a proximal face of drum (1350), an interior surface of drum (1350), on an exterior surface of drum (1350), on a distal face of a raised annulus (1360), on a proximal face of raised annulus (1360), on an external surface of raised annulus (1360) and/or any other surface or combination of surfaces of drum (1350). Accordingly, the positioning of conductive portions (1352, 1356) may be readily determined by one of ordinary skill in the art in view of the teachings herein based upon the radial and/or axial constraints. Moreover, it should be understood that the inclusion of a conductive portion (1352, 1356) on raised annulus results in a slip ring assembly having offset and/or different diameters. In some versions drum (1350) may include a tapered central bore such that the inner surface of the central bore conforms to the contours of the tapered transducer (1300). Still other suitable configurations for drum (1350) having a conductive material thereon will be apparent to one of ordinary skill in the art in view of the teachings herein.

A raised annulus (1360) divides first circumferential surface (1354) from second circumferential surface (1358). Raised annulus (1360) is configured to insert into a recess (1362) in a casing (1360). In some versions, a seal (not shown) may be provided in recess (1362) or on raised annulus (1360). Accordingly, first circumferential surface (1354) and first annular conductive portion (1352) may be electrically and physically isolated from second circumferential surface (1358) and a second annular conductive portion (1356). First annular conductive portion (1352) of the present example is electrically coupled to a first set of electrodes (1320) via a first wire (1322), and second annular conductive portion (1356) is coupled to a second set of electrodes (1320) via a second wire (1322).

An annular casing (1370), as mentioned above, is disposed about drum (1350) and is coupled to a handle assembly (not shown) such that casing (1370) is prevented from rotating relative to drum (1350). Casing (1370) comprises a pair of pogo pins (1380) configured to engage and electrically couple to annular conductive portions (1352, 1356). A pair of wires (1382) extend into casing (1370) and electrically couple pogo pins (1380) to a power supply (e.g., generator (20), etc.). Accordingly, when pogo pins (1380) engage annular conductive portions (1352, 1356) and the power supply is coupled to wires (1382), electrical power is transmitted to transducer (1300) via annular conductive portions (1352, 1356) and wires (1322). When transducer (1300) is rotated by a user, drum (1350) is also rotated via rails (1332) of tube collar cap (1330). As drum (1350) is rotated, pogo pins (1380) continually engage and electrically couple to annular conductive portions (1352, 1356), thereby continuing to provide electrical power to transducer (1300) even when transducer (1300) is rotated through 360 degrees about the longitudinal axis.

Other suitable configurations for drum (1350) and/or transducer (1300) will be apparent to one of ordinary skill in the art in view of the teachings herein. For instance, pogo pins (1380) may be omitted and casing (1370) may include a molded interconnect device ("MID") having a conductive portion that is configured to engage and electrically couple to annular conductive portions (1352, 1356), thereby electrically coupling the power supply to transducer (1300). In yet another alternative, casing (1370) may be omitted entirely and the MID component may be integrated into a surface of a handle assembly, such as handle assembly (60) described above. Alternatively, the handle assembly may include one or more resiliently biased arms having conductive tips. The resiliently biased arms in this example are configured to electrically couple the conductive tips with annular conductive portions (1352, 1356).

ii. Exemplary Alternative Drums and Conductive Portions

Figure 20:
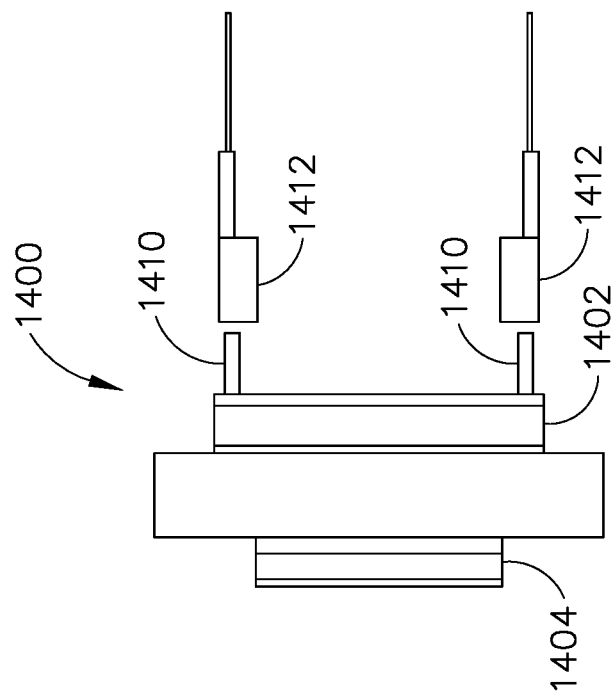
FIG. 20 depicts a side elevation view of an exemplary alternative rotatable drum coupleable to crimp contacts.
Figure 21:
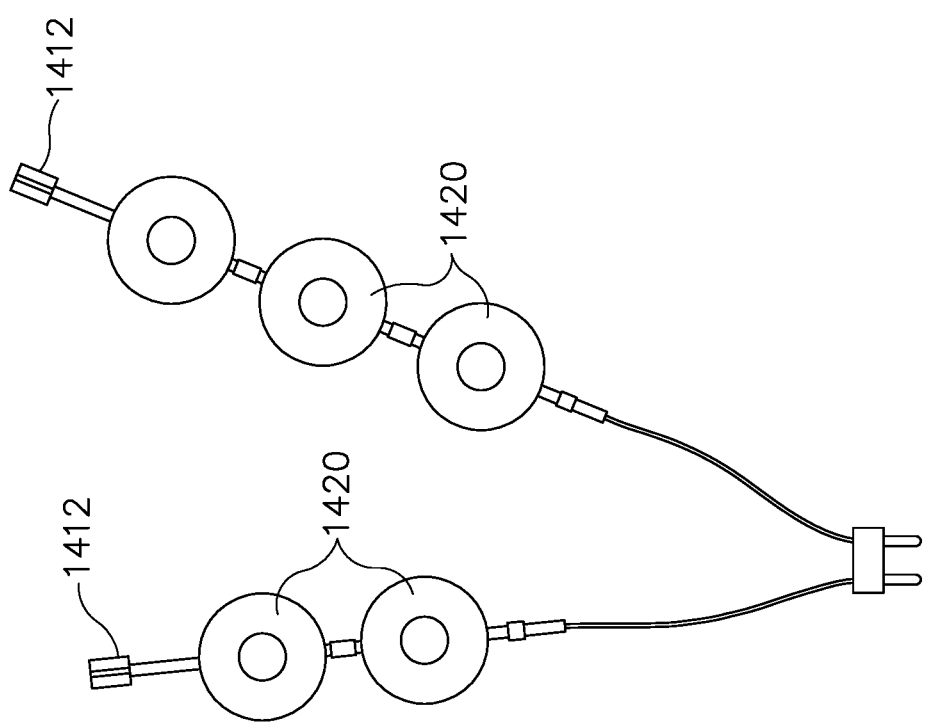
FIG. 21 depicts a top plan view of two strings of electrodes having integrated crimp contacts to couple to the drum of FIG. 20.

Merely exemplary alternative drums and conductive surfaces for such drums are shown in FIGS. 20-24. For instance, FIG. 20 depicts an alternative drum (1400) having spade connectors (1410) that are configured to electrically couple to crimp contacts (1412). In the example shown, spade connectors (1410) are each electrically coupled to a respective conductive ring (1402, 1404) of drum (1400). Accordingly, when drum (1400) is used in a rotatable electrical coupling assembly, such as that shown in FIG. 19, spade connectors (1410) permit drum (1400) to be quickly electrically coupled or decoupled from the electrodes of a transducer via crimp contacts (1412). In some versions, this may permit the user to replace the transducer or the piezoelectric stack without decoupling drum (1400) from the rotatable electrical coupling assembly. FIG. 21 shows one merely exemplary set of electrodes (1420) incorporating crimp contacts (1412) at the end of each set of electrodes (1420). Electrodes (1420) of the present example are alternatingly stacked with the piezoelectric elements of a transducer, such as transducers (100, 300) described above. Once the piezoelectric stack is assembled, crimp contacts (1412) extend distally and are operable to electrically couple to drum (1400) via spade connectors (1410).

Figure 22:
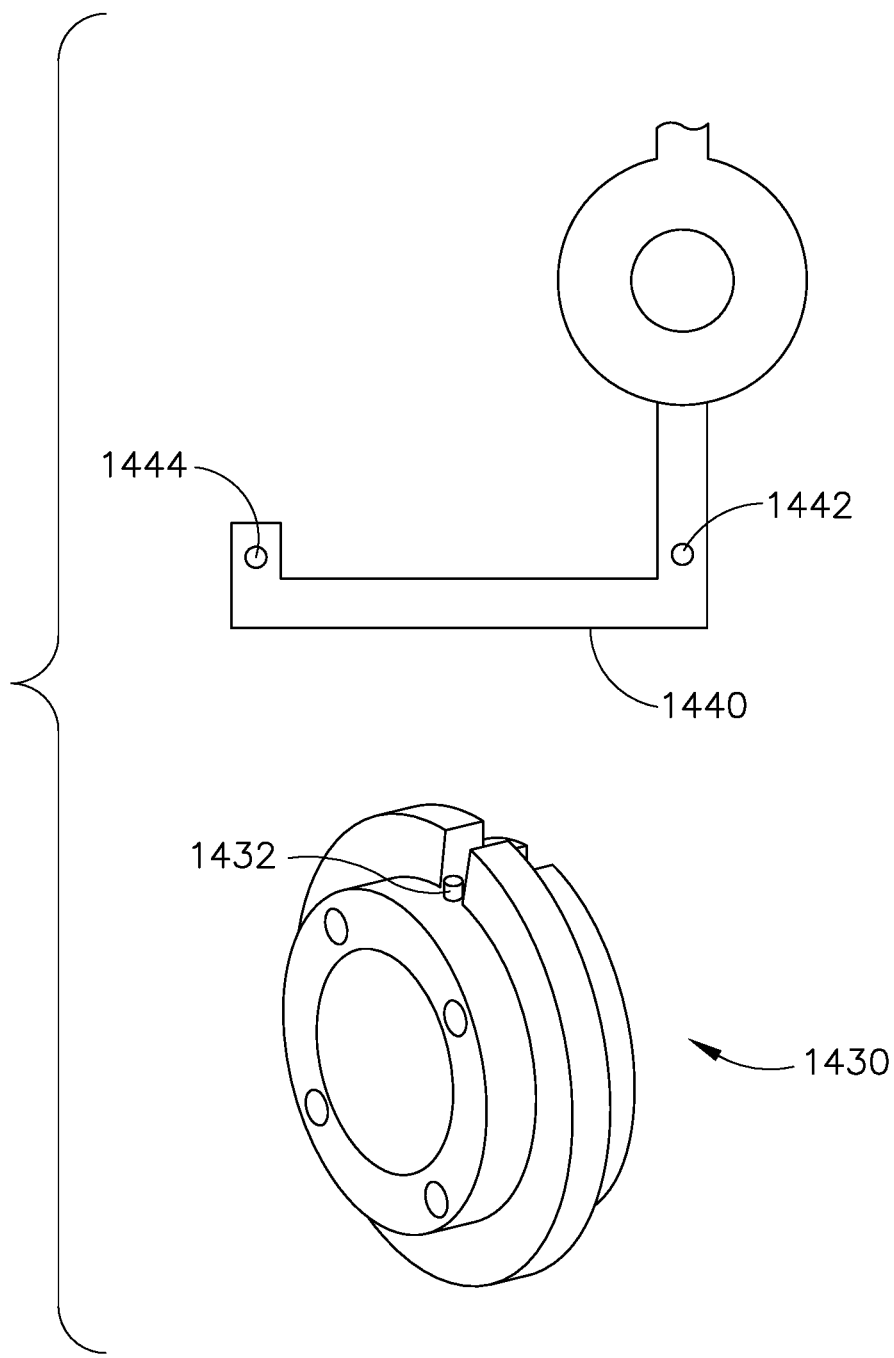
FIG. 22 depicts a perspective view of another alternative rotatable drum having a peg and a top plan view of a conductive portion coupleable to the rotatable drum.

FIG. 22 depicts an alternative drum (1430) where the conductive portion (1440) for drum (1430) is integrated into the end of a set of electrodes such as those shown in FIG. 21. Drum (1430) of the present example may be constructed in accordance with at least some of the teachings of drum (1350) described above. In this example, drum (1430) also includes a peg (1432). Conductive portion (1440) comprises an elongated conductive strip having a pair tabs with holes (1442, 1444) configured to receive peg (1432). In the present example, conductive portion (1440) is shown as a flat member that may be bent when attached to drum (1430). Accordingly, this may enable conductive portion (1440) to be cut or stamped out of a flat conductive material and then coupled to the end of the set of electrodes. When conductive portion (1440) is to be attached to drum (1430), initially first hole (1442) is attached to peg (1432). Conductive portion (1440) is then wrapped around drum (1430) until second hole (1444) is attached to peg (1432). Of course it should be understood that second hole (1444) may be attached first and first hole (1442) is attached second. In some versions an adhesive may be applied to further secure conductive portion (1440) to drum (1430). In others, peg (1432) may include a flared portion (not shown) to further secure conductive portion (1440) to drum (1430). Other suitable configurations for drum (1430) and/or conductive portion (1440) will be apparent to one of ordinary skill in the art in view of the teachings herein.

Figure 23:
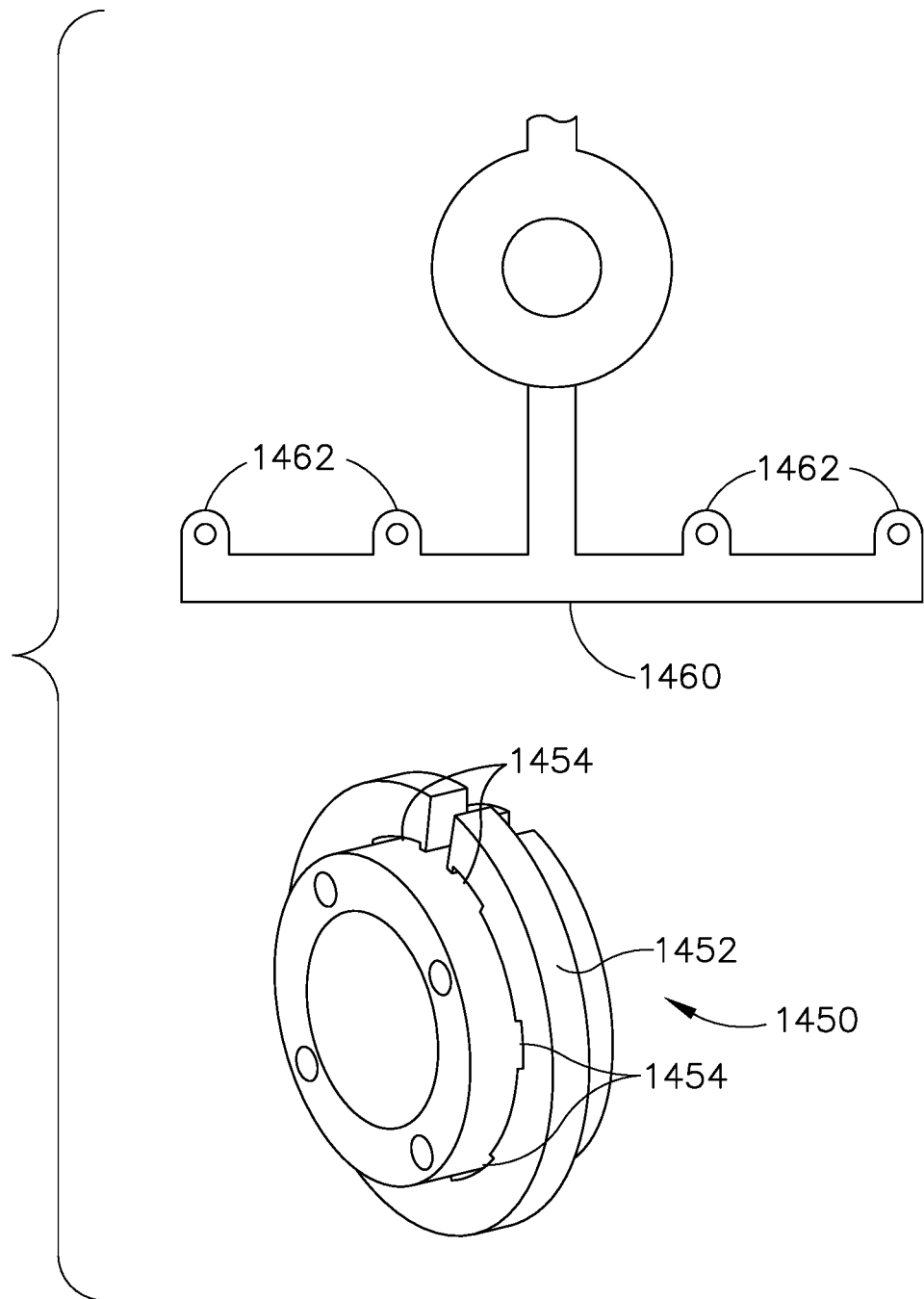
FIG. 23 depicts a perspective view of yet another alternative rotatable drum having slots and a top plan view of a conductive portion coupleable to the rotatable drum.

FIG. 23 depicts an alternative drum (1450) where the conductive portion (1460) for drum (1450) is integrated into the end of a set of electrodes such as those shown in FIG. 21. Drum (1450) of the present example may be constructed in accordance with at least some of the teachings of drum (1350) described above. In this example, drum (1450) also includes a plurality of slots (1454) formed in a raised annulus (1452). Conductive portion (1460) comprises an elongated conductive strip having a plurality of insertable tabs (1462) configured to insert into slots (1454). In the present example, conductive portion (1460) is shown as a flat member that may be bent when attached to drum (1450). Accordingly, this may enable conductive portion (1460) to be cut or stamped out of a flat conductive material and then coupled to the end of the set of electrodes. When conductive portion (1460) is to be attached to drum (1450), conductive portion (1460) is wrapped around drum (1450) and tabs (1462) are inserted into slots (1454). In some versions an adhesive may be applied to further secure conductive portion (1460) to drum (1450). Other suitable configurations for drum (1450) and/or conductive portion (1460) will be apparent to one of ordinary skill in the art in view of the teachings herein.

Figure 24:
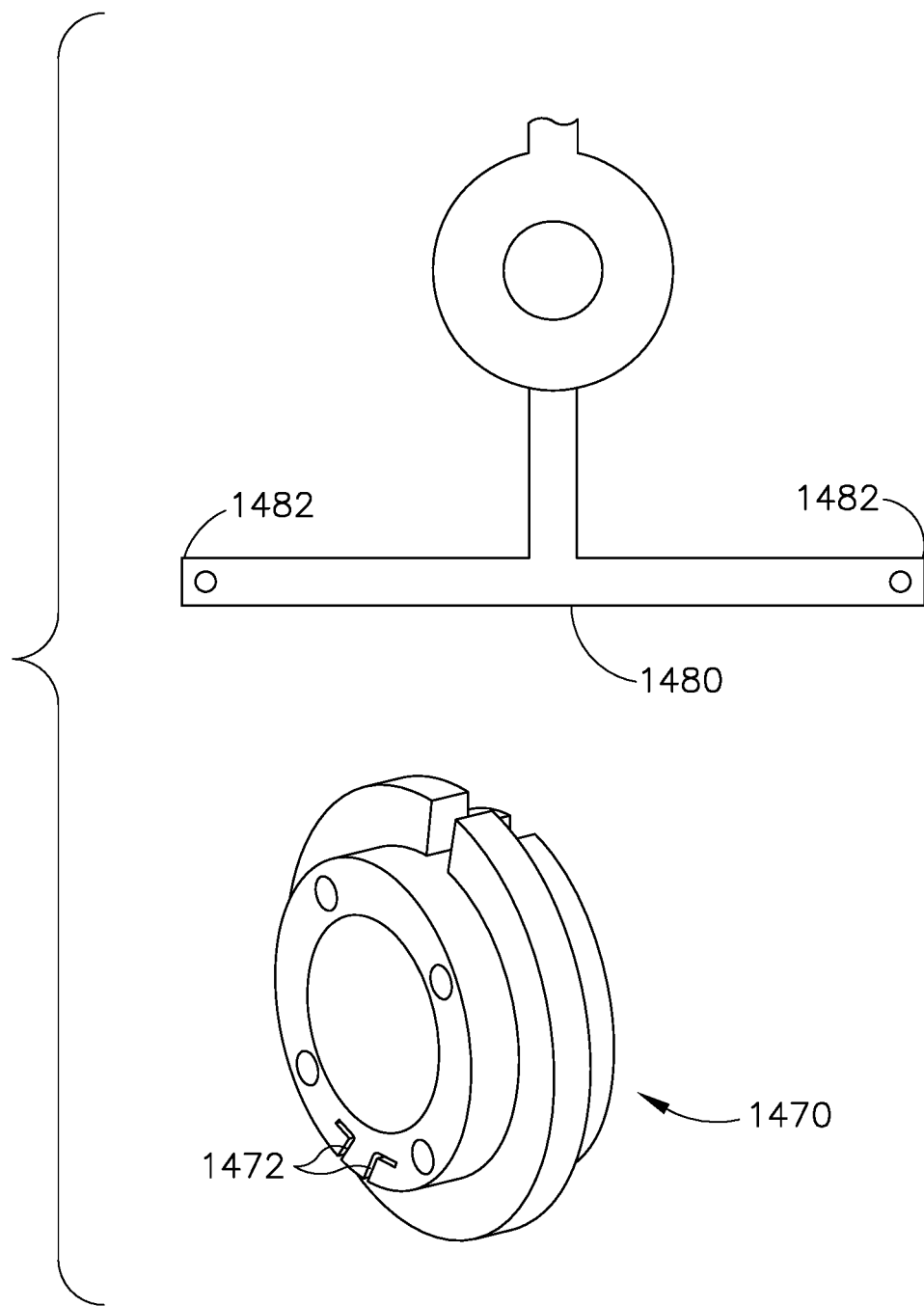
FIG. 24 depicts a perspective view of still another alternative rotatable drum having arcuate slots and a top plan view of a conductive portion coupleable to the rotatable drum.

FIG. 24 depicts yet another alternative drum (1470) where the conductive portion (1480) for drum (1470) is integrated into the end of a set of electrodes such as those shown in FIG. 21. Drum (1470) of the present example may be constructed in accordance with at least some of the teachings of drum (1350) described above. In this example, drum (1470) also includes a pair of arced slots (1472) formed in a distal face of drum (1470). Conductive portion (1480) comprises an elongated conductive strip having ends (1482). In the present example, conductive portion (1480) is shown as a flat member that may be bent when attached to drum (1470). Accordingly, this may enable conductive portion (1480) to be cut or stamped out of a flat conductive material and then coupled to the end of the set of electrodes. When conductive portion (1480) is to be attached to drum (1470), conductive portion (1480) is wrapped around drum (1470) and ends (1482) are inserted into arcuate slots (1472). In some versions an adhesive may be applied to further secure conductive portion (1480) to drum (1470). Other suitable configurations for drum (1470) and/or conductive portion (1480) will be apparent to one of ordinary skill in the art in view of the teachings herein.

While the foregoing examples described a single conductive portion for each drum, it should be understood that the foregoing alternative drums may have conductive portions attached to both the distal and proximal ends of the drums. Moreover, the foregoing exemplary drums may be configured to have a first conductive portion on the distal end of the drum and a second, different conductive portion on the proximal end of the drum. Moreover, it should be understood that the foregoing alternative drums and conductive portions may be integrated into any of the enumerated exemplary rotatable electrical coupling assemblies described herein.

iii. Exemplary Alternative Drum Slip Ring Assembly

Figure 25:
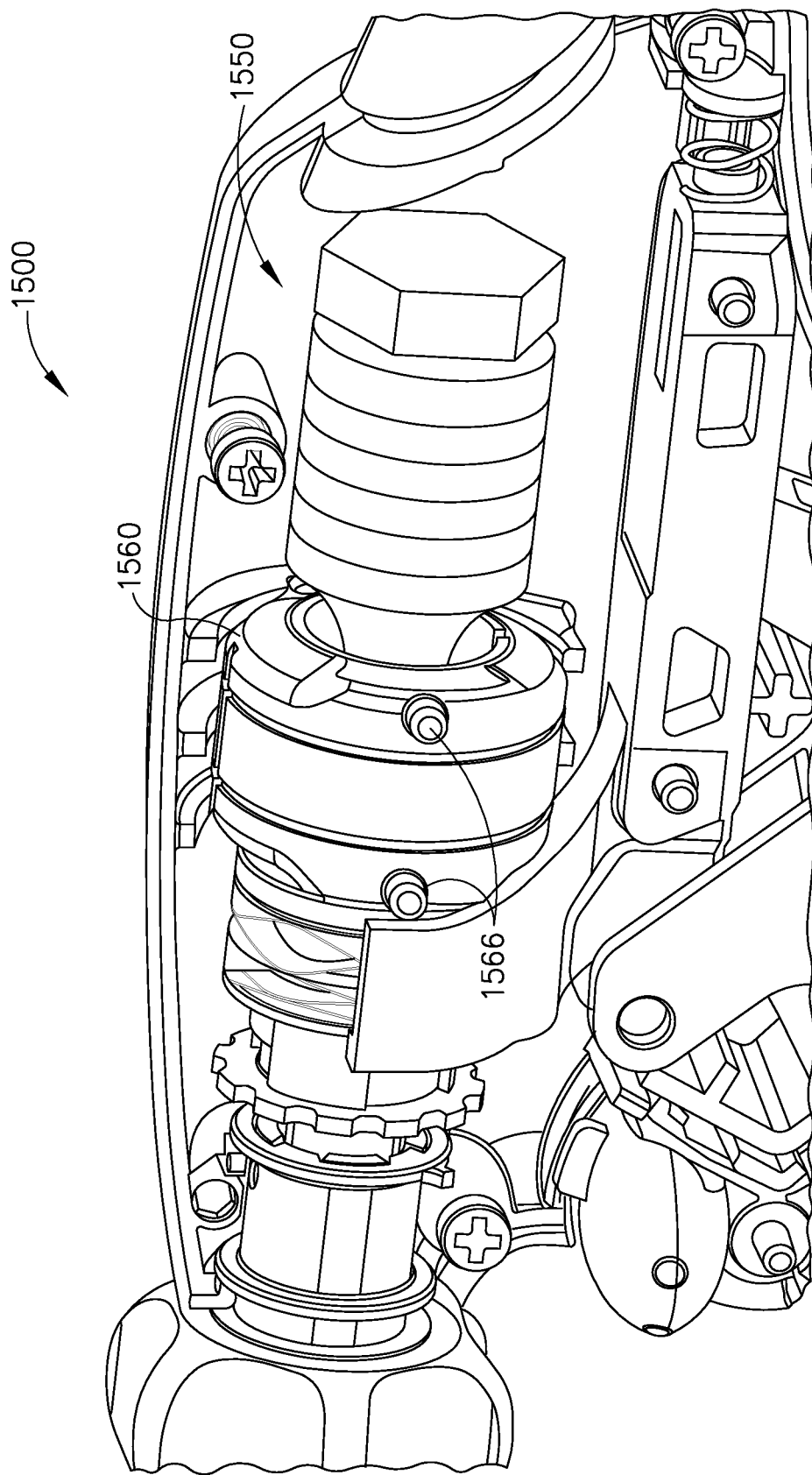
FIG. 25 depicts a partial side perspective view of an exemplary alternative rotatable electrical coupling assembly having a drum contained within a casing rotatably secured by pegs.

One merely exemplary alternative drum slip ring assembly is shown in FIGS. 25-27. Referring initially to FIG. 25, a handle assembly (1500) includes a transducer (1550) disposed therein. Handle assembly (1500) of the present example may be constructed in accordance with at least some of the teachings of handle assembly (60). Transducer (1550) may be constructed in accordance with at least some of the teachings of transducers (100, 300) described herein and/or otherwise. In the present example a drum (1520), shown in FIGS. 26-27, comprises a cylindrical member configured to receive a first annular slip ring (1522) on a first circumferential surface (1524) and a second annular slip ring (1526) on a second circumferential surface (1528). Drum (1520) of the present example is also secured relative to transducer (1500) such that rotation of transducer (1500) also rotates drum (1520) and vice versa. Drum (1520) may be further configured in accordance with at least some of the teachings of drum (1350) described above.

A casing (1560) is disposed about drum (1520) and, in the present example, comprises an upper half (1562) and a lower half (1564) configured to couple together about drum (1520). In the example shown in FIGS. 26-27, upper and lower halves (1562, 1464) couple together via frictionally fitting pins and recesses. Upper half (1562) further includes a pair of apertures through which brushes (not shown) may be inserted to electrically couple to slip rings (1522, 1526). Of course it should be understood that in some versions casing (1560) may include conductors on the interior of upper half (1562) and/or lower half (1564) to form an electrical slip ring assembly with slip rings (1522, 1526). In the present example, casing (1560) further includes a pair of pegs (1566) extending outwardly from opposing sides of casing (1560). Pegs (1566) are configured to insert into longitudinal slots (not shown) formed in handle assembly (1500) such that casing (1560) is rotationally secured within handle assembly (1500) while casing (1560) is still permitted to translate longitudinally via pegs (1566) inserted into the slots. Accordingly, when drum (1520) is disposed about transducer (1550) and casing (1560) is disposed about drum (1520), then casing (1560) is permitted to translate with drum (1520) and with transducer (1550) in handle assembly (1500) via pegs (1566) in the slots of handle assembly (1500). Furthermore, it should be understood that since pegs (1566) prevent rotation of casing (1560), when transducer (1550) is rotated, casing (1560) does not rotate. Accordingly, when brushes and/or conductors are coupled to a power supply and electrically coupled to slip rings (1522, 1526) of drum (1520), the slip ring assembly formed by casing (1560) and drum (1520) permit transducer (1550) to remain electrically coupled to the power supply even when transducer (1550) is rotated through 360 degrees. Other suitable configurations for drum (1520), transducer (1550), and/or casing (1560) will be apparent to one of ordinary skill in the art in view of the teachings herein.

iv. Exemplary Alternative Rotary Electrical Coupling Assembly

Figure 28:
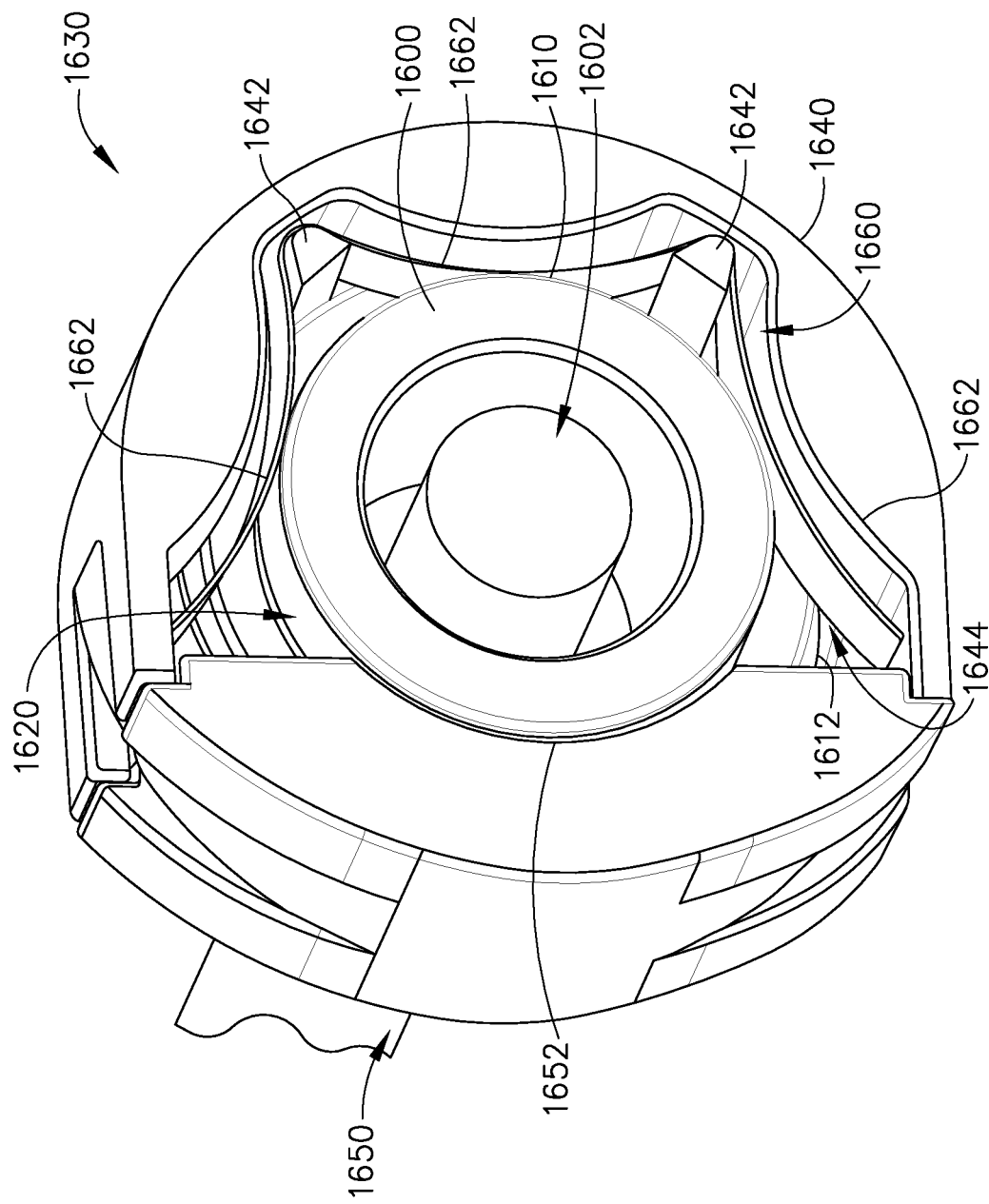
FIG. 28 depicts a perspective view of still yet another exemplary rotatable electrical coupling assembly having a biased contact strip with arcuate contact portions.

FIG. 28 shows yet another exemplary alternative drum slip ring assembly comprising a drum (1600) and housing (1630) with a biased contact strip (1660). Drum (1600) of the present example is disposed about a portion of a transducer (1602) and drum (1600) comprises a body portion (1610), a raised annulus (1612), and a pair of conductive portions (1620) disposed about a proximal and a distal end of body portion (1610). Drum (1600) may be further constructed in accordance with at least some of the teachings of drums (1350, 1410, 1430, 1450, 1470, 1520) and/or otherwise. Housing (1630) of the present example comprises a main portion (1640) and a hinge portion (1650). Main portion (1640) is a U-shaped member configured to partially fit around drum (1600). A channel (1644) is formed in main portion (1640). Channel (1644) is configured to receive and longitudinally retain raised annulus (1612) when drum (1600) is inserted into main portion (1640). Main portion (1640) further includes two retaining members (1642) configured retain portions of biased contact strip (1660). Biased contact strip (1660) comprises a conductive strip having a plurality of arcuate contact portions (1662). In the present example, contact portions (1662) are configured to bias inwardly toward drum (1600) when biased contact strip (1660) is coupled to main portion (1640) via retaining members (1642). In some versions main portion (1640) is integrated into a handle assembly, such as handle assembly (60) described above. In other versions, main portion (1640) may be longitudinally translatable relative to the handle assembly via pegs or ledges extending from an outer surface of main portion (1640). Other suitable configurations for main portion (1640) and/or biased contact strip (1660) will be apparent to one of ordinary skill in the art in view of the teachings herein.

Hinge portion (1650) is configured to pivot from an open position, in which drum (1600) may be loaded into main portion (1640), to a closed position, in which hinge portion (1650) compresses drum (1600) into engagement with contact portions (1662). Hinge portion (1650) and/or main portion (1640) may optionally include a retention feature (e.g., a latch, clip, clamp, etc.) to lock hinge portion (1650) in the closed position. Hinge portion (1650) of the present example includes an arced recess (1652) that conforms to a portion of the curvature of drum (1600), though this is merely optional. In the example shown in FIG. 28, hinge portion (1650) is shown in the closed position, thereby compressing and electrically coupling conductive portions (1620) of drum (1600) with contact portions (1662) of biased contact strip (1660). Accordingly, drum (1600) and biased contact strip (1660) remain electrically coupled even when drum (1600) is rotated through 360 degrees of rotation. In some other versions, drum (1600) may be loaded from the distal end of drum (1600) and/or from the proximal end of drum (1600), such that drum (1600) is inserted into housing (1630) along a longitudinal path. Drum (1600) and/or housing (1630) may include a beveled edge to facilitate such insertion. Other suitable configurations for drum (1600), main portion (1640), and/or hinge portion (1650) will be apparent to one of ordinary skill in the art in view of the teachings herein.

v. Exemplary Alternative Rotary Electrical Coupling Assembly

Figure 29:
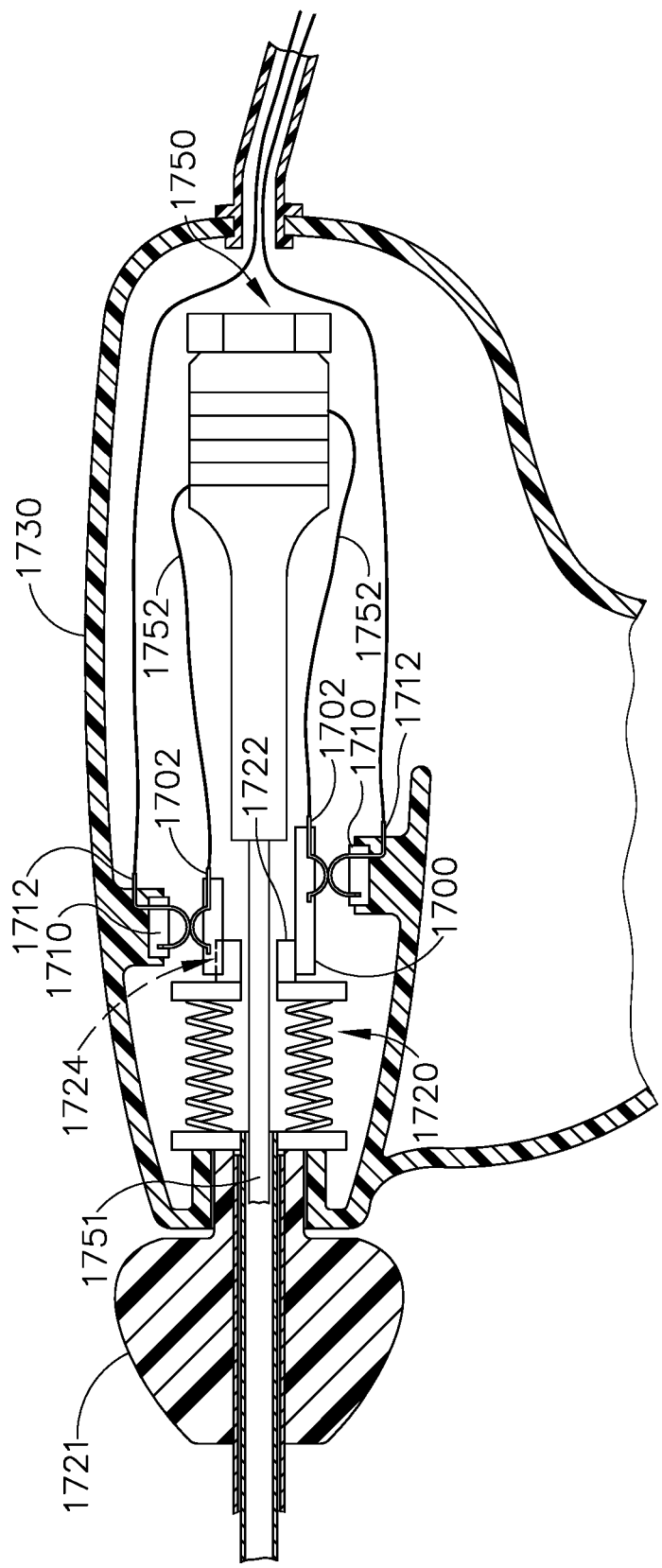
FIG. 29 depicts a side cross-sectional view of still another exemplary alternative rotatable electrical coupling assembly having a rotatable drum carried by a threaded tube collar.

FIG. 29 shows another exemplary alternative drum slip ring assembly comprising an inner drum (1700), an outer ring (1710), a threaded tube collar (1720), and a casing (1730). In the present example, inner drum (1700) is a tubular member having conductive contacts (1702) that are electrically coupled to a transducer (1750) via a pair of transducer wires (1752). Transducer (1750) of the present example may be constructed in accordance with at least some of the teachings of transducers (100, 300) and/or otherwise constructed. Transducer (1750) communicates with a waveguide (1751) and a harmonic blade (not shown), which together form an acoustic assembly. The acoustic assembly is supported by rotation knob (1721), which is rotatably coupled to casing (1730). Inner drum (1700) is also supported by rotation knob (1721). Inner drum (1700) is configured to electrically couple conductive contacts (1702) to complementary contacts (1712) on outer ring (1710), as will be discussed in more detail below. In some versions inner drum (1700) may omit contacts (1702) and instead have a flat surface to which complementary contacts (1712) engage and electrically couple. Further configurations for inner drum (1700) will be apparent to one of ordinary skill in the art in view of the teachings herein.

In the present example, a threaded tube collar (1720) is coupled to casing (1730) at a distal end of threaded tube collar (1720) and to inner drum (1700) at a proximal end of threaded tube collar (1720). In the example shown, a tubular portion (1722) of threaded tube collar (1720) is configured to insert into the inner diameter of inner drum (1700) such that inner drum (1700) is carried by tubular portion (1722). Tubular portion (1722) also includes a keyed portion (1724) (shown in phantom) on the exterior surface of tubular portion (1722). Keyed portion (1724) is configured to insert into a key slot formed in inner drum (1700) such that threaded tube collar (1720) is operable to rotate inner drum (1700). In some versions inner drum (1700) may be configured to translate on tubular portion (1722) while still being rotationally coupled to threaded tube collar (1720) by keyed portion (1724). In other versions, inner drum (1700)

may be integrally formed with or physically coupled to threaded tube collar (1720) (e.g., adhesively attached, pinned, clipped, bolted, etc.). In such versions, tubular portion (1722) and keyed portion (1724) may be omitted. Threaded tube collar (1720) may be further constructed in accordance with at least some of the teachings for tube collar cap (1330) described above; collar (93) of U.S. Pat. Pub. No. 2006/0079874, now abandoned; tube collar (98) of U.S. Pat. Pub. No. 2007/0282333, now abandoned and/or otherwise.

Outer ring (1710) of the present example is mounted to casing (1730) and is configured to form a slip ring assembly with inner drum (1700). As shown in FIG. 29, outer ring (1710) includes a pair of complementary contacts (1712) configured to engage and electrically couple outer ring (1710) with inner drum (1700). Of course, it should be understood that outer ring (1710) may be omitted and a pair of point contacts may be mounted to casing (1730) to electrical couple to inner drum (1700). In the present example, outer ring (1710) is electrically coupled to a power supply (not shown) via wires. Accordingly, with outer ring (1710) and inner drum (1700) electrically coupled, transducer (1750) may be rotated relative to casing (1730) while still maintaining electrical power from a power supply and not twisting any wires within casing (1730). Further configurations for inner drum (1700), outer ring (1710), and/or alternative drum slip ring assembly will be apparent to one of ordinary skill in the art in view of the teachings herein. In some versions, inner drum (1700) and/or outer ring (1710) may be manufactured as MID components.

It should be understood that aspects of one or more of the preceding drum slip ring assemblies may be readily combined with aspects of any of the other drum slip ring assemblies described herein. It should also be understood that the drum slip ring assemblies described above may be readily combined with any other teachings herein.

H. Exemplary Molded Interconnect Device Electrical Coupling Assemblies for a Transducer In some situations, it may be preferable to reduce the number of components that are used to electrically couple transducer (100) to a power supply. For instance, in some arrangements the brushes of a drum assembly may be integrated into a portion of handle assembly (60). In addition or in the alternative, it may be useful to integrate conductive paths into the drum. In yet further instances it may be preferable to integrate conductive paths into the brush unit that electrically couples to the drum. Accordingly, various configurations for electrical coupling assemblies utilizing molded interconnect devices will be described herein.

Figure 30:
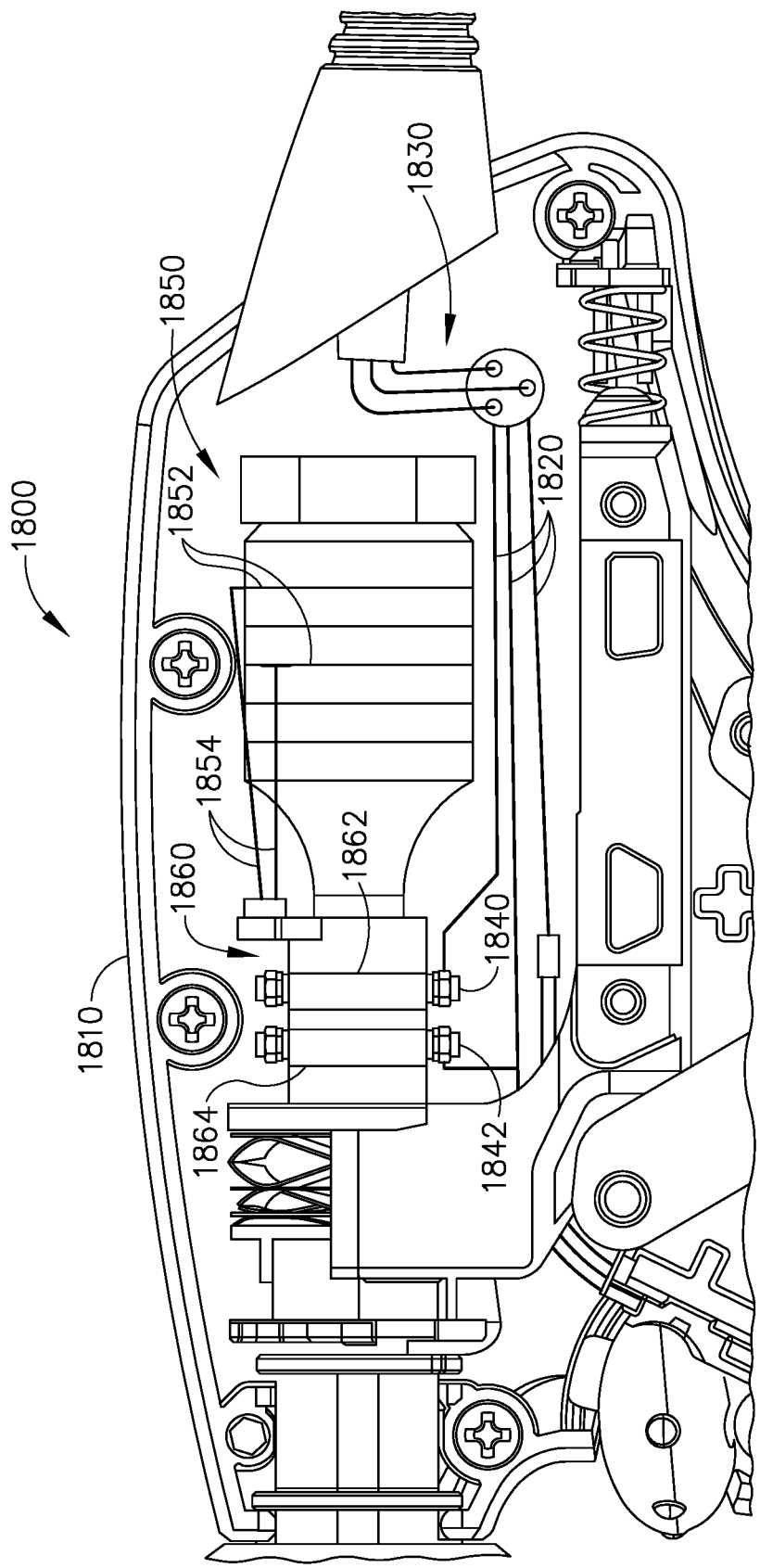
FIG. 30 depicts a partial side elevation view of an exemplary rotatable electrical coupling assembly having conductive traces and integrated MID brushes in the handle assembly.

FIG. 30 depicts an exemplary handle assembly (1800) having a transducer (1850) disposed therein. Handle assembly (1800) and transducer (1850) may be constructed in accordance with at least some of the teachings of handle assemblies (60) and/or transducer (100, 300) described above. In the present example, handle assembly (1800) comprises a casing (1810) having a plurality of conductive traces (1820) formed in casing (1810). Conductive traces (1820) may be formed via chemical etching, printing of conductive ink, as a part of a molded interconnect device, and/or otherwise. Conductive traces (1820) of the present example are electrically coupled to cable wires (1830), to one or more switches (not shown), to a first brush lead (1840), and to a second brush lead (1842). As shown in FIG. 30, brush leads (1840, 1842) are integrally coupled to casing (1810) and have conductive portions that are configured to electrically couple one or more of the cable wires (1830) with a corresponding conductive portion (1862, 1864) of drum (1860).

Drum (1860) of the present example comprises a cylindrical member disposed about a distal portion of transducer (1850) and includes a pair of conductive portions (1862, 1864) disposed about the circumference of drum (1860). In the example shown, first brush lead (1840) electrically couples to a first conductive portion (1862) of drum (1860) while second brush lead (1842) electrically couples to a second conductive portion (1864) of drum (1860). In some versions, drum (1860) is a molded interconnect device having conductive portions (1862, 1864) integrally formed on drum (1860). Conductive portions (1862, 1864) are further electrically coupled to corresponding electrodes (1852) of a transducer (1850) via transducer wires (1854). Transducer (1850) and electrodes (1852) of the present example may be constructed in accordance with at least some of the teachings of transducers (100, 300) described above.

When a power supply (e.g., generator (20), etc.) is coupled the cable wires (1830), electrical power is transmitted to transducer (1850) via the electric coupling assembly formed by brush leads (1840, 1842) and drum (1860). Accordingly, even when transducer (1850) (and therefore drum (1860)) is rotated, brush leads (1840, 1842) remain electrically coupled to conductive portions (1862, 1864), thereby maintaining an electrical connection with transducer (1850) even when transducer (1850) is rotated through 360 degrees.

Other suitable configurations for brush leads (1840, 1842), drum (1860), and/or handle assembly (1800) will be apparent to one of ordinary skill in the art in view of the teachings herein. For instance, in some versions drum (1860) and brush leads (1840, 1842) need not necessarily be contained within handle assembly (1800). Instead, drum (1860) and brush leads (1840, 1842) may be contained within a casing for transducer (1850) and a brush leads (1840, 1842) may be selectively coupled to a power supply when transducer (1850) is inserted into handle assembly (1800). One merely exemplary selective coupling assembly for transducer (1850) may include a nosecone coupled to a distal end of transducer (1850). One merely exemplary construction for such a nosecone is shown and described in reference to FIG. 8B of U.S. Pat. Pub. No. 2006/0079874, now abandoned, the disclosure of which is incorporated by reference herein. In addition or in the alternative, brush leads (1840, 1842) may be omitted, and MID conductive channels may be formed in casing (1810). In such a configuration, conductive rings (1862, 1864) may be omitted and a pair of conductive discs, such as discs (710, 760, 820, 870), may be provided on drum (1860) to electrically couple transducer (1850) to the conductive channels formed in casing (1810).

Figure 31:
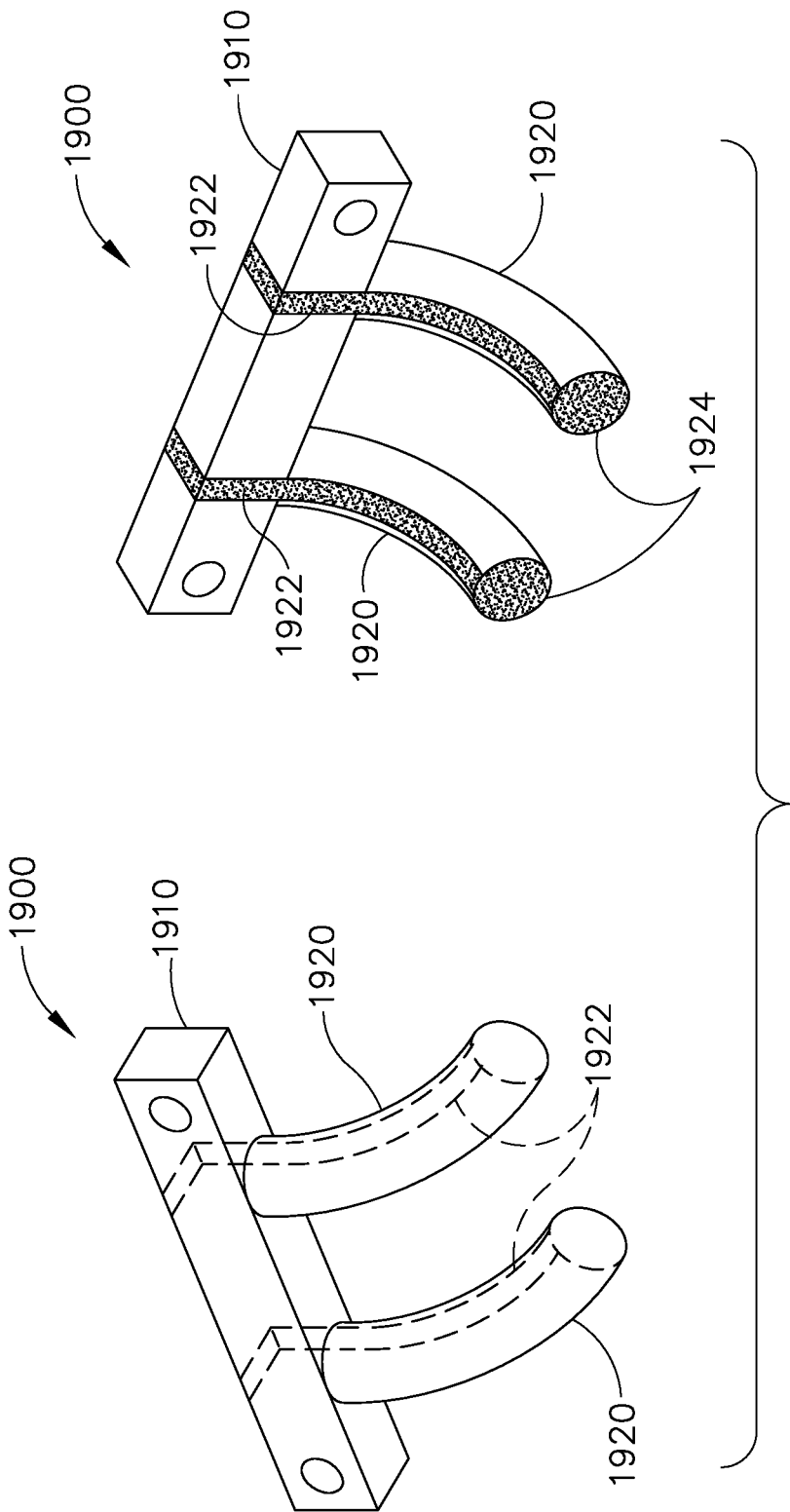
FIG. 31 depicts a top perspective view and a bottom perspective view of a selectively coupleable MID brush assembly.

FIG. 31 depicts an exemplary alternative brush assembly (1900) that is selectively coupleable to handle assembly (1800). Brush assembly (1900) of the present example comprises a body member (1910) and a pair of resiliently biased arms (1920). In the present example, arms (1920) include conductive traces (1922) that terminate in contacts (1924) configured to electrically couple to conductive portions of a drum, such as drum (1860). Brush assembly (1900) of the present example comprises a molded interconnect device. In some versions, a pair of wires (not shown) may be coupled to conductive traces such that brush assembly (1900) may be coupled to a cable, such as cable (30). Alternatively, a portion of conductive traces (1922) may be exposed on a portion of body member (1910) such that when brush assembly (1900) is coupled to handle assembly (1800), brush assembly (1900) electrically couples to exposed electrical contacts on handle assembly (1800).

Further configurations for brush assembly (1900) will be apparent to one of ordinary skill in the art in view of the teachings herein.

Figure 32:
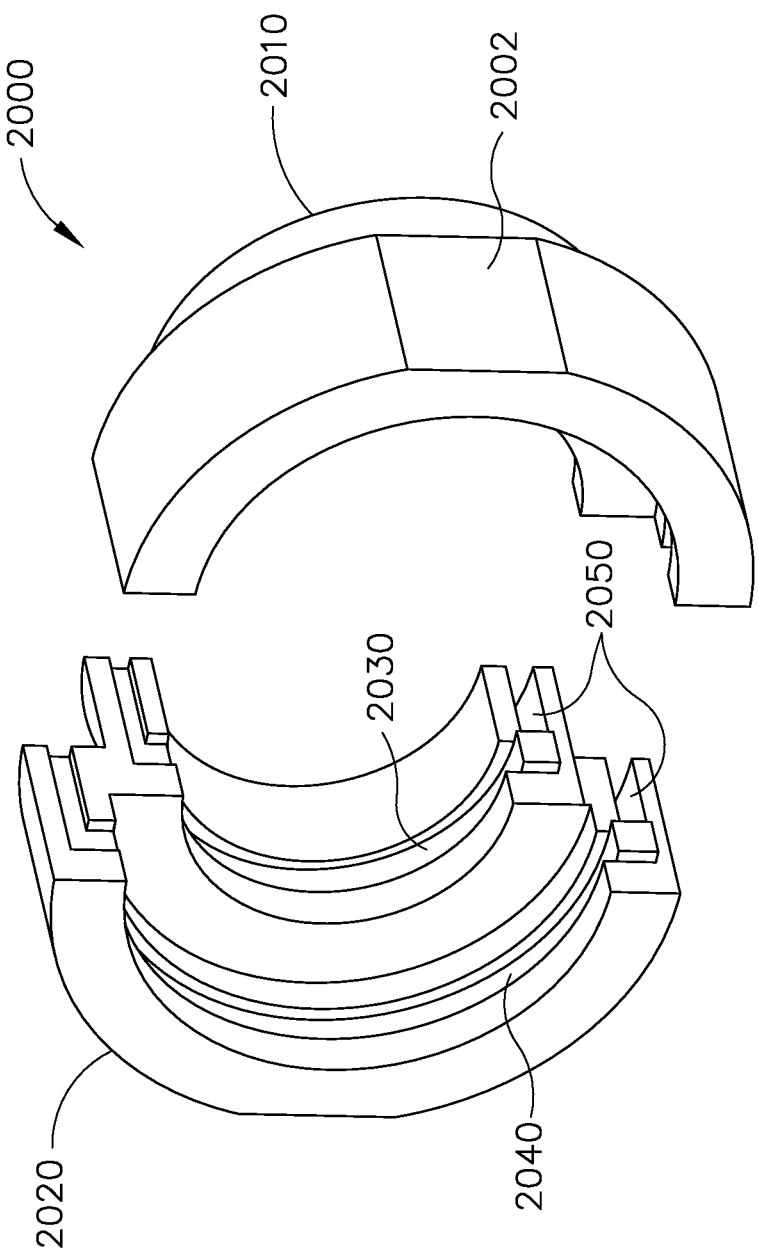
FIG. 32 depicts an exploded perspective view of an exemplary MID drum.

In some versions, a stator drum (2000), shown in FIG. 32, may be configured to electrically couple to drum (1860) to form a slip ring assembly. In addition or in the alternative, stator drum (2000) may electrically couple to resiliently biased arms or brushes. Stator drum (2000) of the present example comprises a molded interconnect device formed by the coupling of two halves (2010, 2020) that are configured to frictionally fit together. Each half (2010, 2020) comprises a plastic body, a half of a first slip ring (2030), and a half of a second slip ring (2040). When halves (2010, 2020) are coupled together, first slip ring (2030) and second slip ring (2040) form a pair of continuous exposed slip rings on the interior surface of drum (2000). Each half (2010, 2020) further comprises a pair of longitudinal slots (2050) intersecting with slip rings (2030, 2040). Longitudinal slots (2050) are configured to each receive a wire (not shown) therein such that the wires electrically couple slip rings (2030, 2040) with a power supply (e.g., generator (20), etc.). Accordingly, when halves (2010, 2020) are pressed together about drum (1860), slip rings (2030, 2040) electrically couple to drum (1860), thereby providing electrical power to transducer (1850) while still permitting transducer (1850) to rotate relative to stator drum (2000). Stator drum (2000) further includes a pair of flat portions (2002) on opposing exterior portions of stator drum (2000) such that stator drum (2000) is prevented from rotating when flat portions (2002) abut a surface. For instance, flat portions (2002) may abut the interior of handle assembly (1800), thereby preventing rotation of stator drum (2000) while drum (1860) is permitted to rotate freely therein. Flat portions (2002) may still permit stator drum (2000) to translate within handle assembly (1800). Still further configurations for stator drum (2000) will be apparent to one of ordinary skill in the art in view of the teachings herein.

Of course, other components of the transducer and/or handle assembly may be molded interconnect devices as well. For instance, as noted above, a nosecone that selectively electrically couples the transducer to handle assembly may be formed as an MID component.

I. Exemplary Printed Circuit Board Electrical Coupling Assemblies

In some instances, it may be useful to construct the electrical coupling assemblies that electrically couple transducer (100) to the power supply from cost-effective materials. Merely exemplary cost-effective materials may include printed circuit boards ("PCB") having conductive traces that may be electrically coupled to stamped brushes. Various examples of ways in which PCBs may be used to construct electrical coupling assemblies will be described in greater detail below, while other examples will be apparent to those of ordinary skill in the art in view of the teachings herein.

i. Exemplary PCB Electrical Coupling Assembly Having Stamped Brush Contacts

One merely exemplary PCB electrical coupling assembly (2100) is shown in FIGS. 33-36. PCB electrical coupling assembly (2100) comprises a rotatable PC board (2110) (see FIG. 34), a rotation drum (2120) (see FIG. 33), a transfer casing (2150) (see FIG. 35), and a pair of stamped brush contacts (2170) (see FIG. 36). In the example shown in FIG. 36, an exemplary transducer (2190) is shown electrically coupled to PCB electrical coupling assembly (2100) via a pair of wires (2192). Transducer (2190) may be constructed in accordance with at least some of the teachings of transducers (100, 300) described above and/or otherwise. Referring initially to FIG. 34, PC board (2110) of the present example comprises a substantially flat disc having conductive traces (2112) on both sides of PC board (2110). It should be understood that a multitude of conductive traces (2112) may be coaxially formed on a single side of PC board (2112) or that only a single conductive trace (2112) may be provided on one side of PC board (2110). Conductive traces (2112) may be formed on PC board (2110) by chemical etching, printing of conductive ink, as a part of a molded interconnect device, and/or otherwise. Conductive traces (2112) of the present example comprise circular paths of conductive material (e.g., gold, copper, etc.) such that a brush contact (2170) (shown in FIGS. 35-36) is operable to electrically couple to conductive traces (2112) even when PC board (2110) is rotated through 360 degrees. In the example shown, conductive traces (2112) further include a coupling point (2114) to which wire (2192) may be soldered, pinned, and/or otherwise electrically coupled to conductive traces (2112). Wire (2192) is then electrically coupled to one or more electrodes (not shown) of transducer (2190). Accordingly, as will be apparent to one of ordinary skill in the art in view of the teachings herein, PC board (2110) is operable to transmit power from brush contact (2170) to transducer (2190) even when transducer (2190) and PC board (2110) are rotated relative to brush contact (2170).

PC Board (2110) further includes a central aperture (2116) having a pair of key slots (2118). Central aperture (2116) and key slots (2118) are sized and configured to receive a central member (2122) of rotation drum (2120), shown in FIG. 33. Central member (2122) of rotation drum (2120) comprises a hollow cylindrical member configured to fit around a distal portion of transducer (2190). For instance, in the example shown in FIG. 36, central member (2122) is disposed about a first resonator of transducer (2190), though this is merely optional. In other versions, central member (2122) may be disposed about the piezoelectric elements of transducer (2190). Of course central member (2122) need not necessarily be disposed about any portion of transducer (2190). In the example shown in FIG. 33, central member (2122) includes keyed portions (2124) extending outwardly from central member (2122). Keyed portions (2124) are configured to engage with key slots (2118) of PC board (2110) such that rotation drum (2120) rotates PC board (2110) when central member (2122) is inserted into central aperture (2116) of PC board (2110). It should be understood that while keyed portions (2124) rotationally couple PC board (2110) to rotation drum (2120), PC board (2110) and/or rotation drum (2120) are permitted to longitudinally translate relative to each other with keyed portions (2124) still engaged with key slots (2118). Accordingly, even if rotation drum (2120) is actuated proximally or distally (e.g., if rotation drum (2120) is coupled to a translatable transducer), PC board (2110) remains rotatable via keyed portions (2124) and key slots (2118).

Rotation drum (2120) of the present example is configured to couple to transducer (2190) such that rotation of transducer (2190) also rotates rotation drum (2120). In the arrangement shown in FIG. 36, rotation drum (2120) includes a flange (2126) configured to couple to a collar assembly (2194) coupled to transducer (2190). Collar assembly (2194) may be constructed in accordance with at least some of the teachings of tube collar cap (1330); threaded tube collar (1730); collar (93) of U.S. Pat. Pub. No. 2006/0079874, now abandoned; tube collar (98) of U.S. Pat. Pub. No. 2007/0282333, now abandoned and/or otherwise. Flange (2126) of the present example may be adhesively or mechanically (e.g., pins, threading, latches, etc.) coupled to collar assembly (2194). Accordingly, when transducer (2190) is rotated, rotation drum (2120) is also rotated. Other suitable configurations for coupling rotation drum (2120) to transducer (2190) will be apparent to one of ordinary skill in the art in view of the teachings herein.

Referring now to FIGS. 35-36, a transfer casing (2150) is configured to encase the assembled rotation drum (2120) and PC board (2110) therein. In the example shown, transfer casing (2150) comprises a two-piece hollow cylinder having an annular channel (2152) configured to receive and retain PC board (2110) therein when transfer casing (2150) is assembled about rotation drum (2120) and PC board (2110). Annular channel (2152) of the present example is configured to restrict the longitudinal movement of PC board (2110) relative to transfer casing (2150). Such longitudinal restriction may be useful to ensure an adequate electrical coupling of brush contacts (2170) with conductive traces (2112), as will be described in more detail below. In other versions, a resiliently biased member, such as a spring, may be disposed between flange (2126) of rotation drum (2120) and a portion of PC board (2110) to bias PC board (2110) in the proximal direction against one or more brush contacts (2170). Still further configurations will be apparent to one of ordinary skill in the art in view of the teachings herein.

Figure 37:
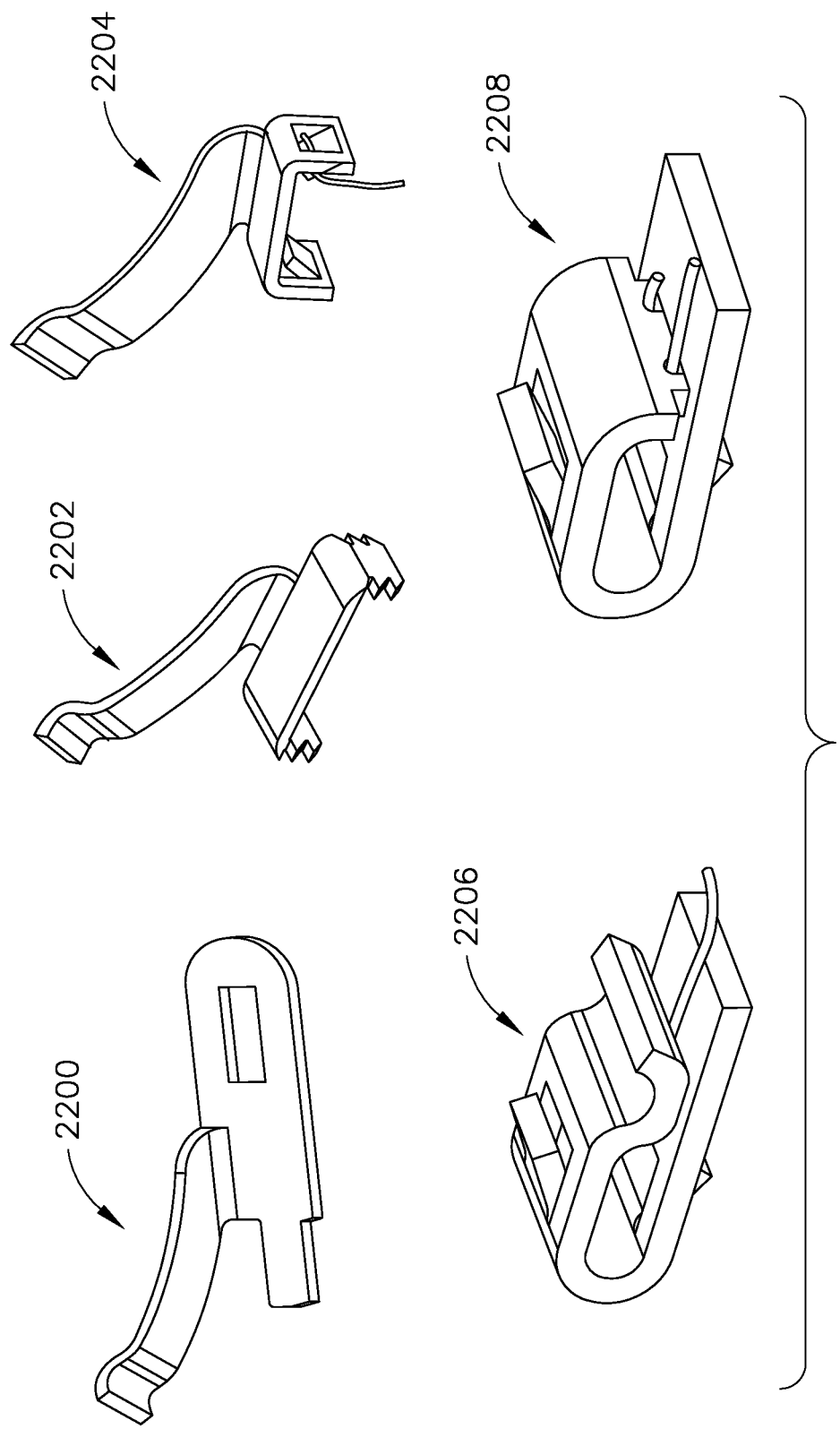
FIG. 37 depicts perspective views of various alternative brush contacts.

Transfer casing (2150) further includes openings (2154) through which brush contacts (2170) may be coupled to one or more wires (not shown) from a cable (not shown) configured to provide power to transducer (2190). Brush contacts (2170) of the present example comprise stamped members that are operable to engage and electrically couple the cable with conductive traces (2112) of PC board (2110). In the present example, brush contacts (2170) each include a resilient arm (2172), a body portion (2174), and a connection tab (2176). Resilient arm (2172) extends from body portion (2174) and biases away from body portion (2174). As shown in FIG. 36, when PCB electrical coupling assembly (2100) is assembled, resilient arms (2172) brush against and electrically couple brush contacts (2170) to conductive traces (2112). Body portion (2174) of the present example is configured to couple to an interior portion of transfer casing (2150) such that brush contacts (2170) are substantially secured to transfer casing (2150). In the example shown, a tab of transfer casing (2150) inserts into a hole formed in body portion (2174) to secure brush contact (2170) to transfer casing (2150). Of course, other securing components and/or methods may be used to secure brush contacts (2170) to transfer casing (2150) (e.g., snaps, clips, clamps, screws, bolts, integral formation, adhesives, etc.). Connection tab (2176) is configured to electrically couple to one or more wires of the cable. Other suitable configurations for brush contacts (2170) will be apparent to one of ordinary skill in the art in view of the teachings herein. Merely exemplary alternative brush contacts (2200, 2202, 2204, 2206, 2208) are shown in FIG. 37.

Transfer casing (2150) of the present example further includes exterior ledges (2156), though this is merely optional. Exterior ledges (2156) are configured to engage slots (not shown) formed in a handle assembly, such as handle assembly (60), to prevent rotation of transfer casing (2150). Accordingly, when the wires from the cable are coupled to brush contacts (2170) described above, preventing transfer casing (2150) from rotating may prevent the wires from the cable from tangling. It should be understood that exterior ledges (2156) do not restrict transfer casing (2150) from translating relative to the handle assembly. Accordingly, in some versions PCB electrical coupling assembly (2100) may be integrated into a transducer assembly that may be longitudinally inserted into a handle assembly via engagement of exterior ledges (2156) with the slots formed in the handle assembly.

When a surgical instrument having PCB electrical coupling assembly (2100) is in use, transducer (2190) remains electrically coupled to the cable and the wires of the cable remain untangled even when the user rotates transducer (2190) through 360 degrees of rotation.

Figure 38:
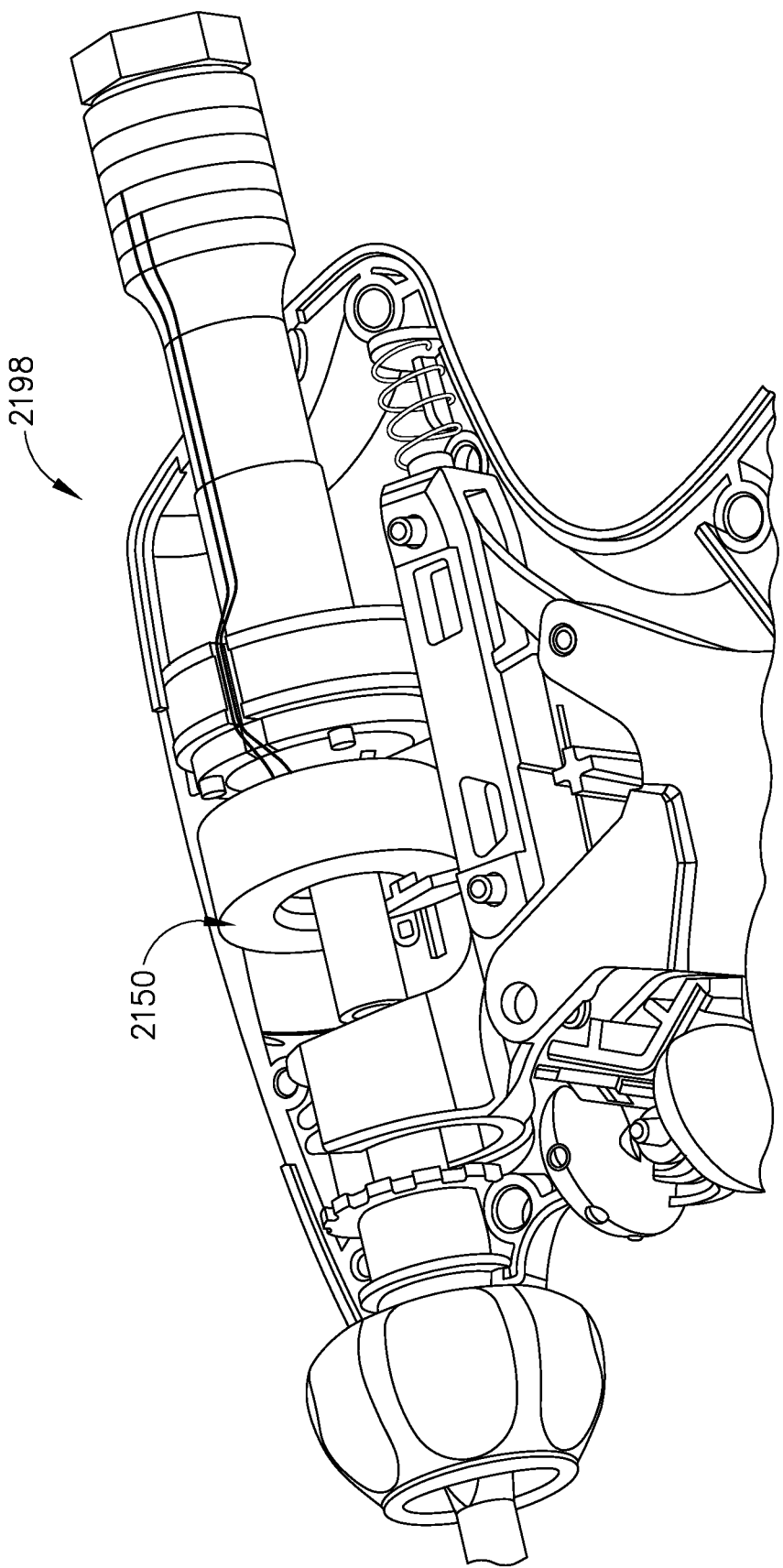
FIG. 38 depicts a partial perspective view of an exemplary alternative rotatable electrical coupling assembly having a PC board with conductive traces and a transfer casing integrated into a handle assembly.

It should be understood that the foregoing description is merely one example of a PCB electrical coupling assembly (2100) and other various configurations and/or arrangements will be apparent to one of ordinary skill in the art in view of the teachings herein. For instance, in some versions only a single brush contact (2170) and conductive trace (2112) are used. Alternatively, in some versions brush contacts (2170) may be configured to electrically couple to PC board (2110), transfer casing (2150), and/or rotation drum (2120) at a variety of locations. By way of example only, brush contacts (2170) may electrically couple to conductive portions located on the interior surface of rotation drum (2120), on the exterior surface of rotation drum (2120), on the proximal surface of PC board (2110), on the distal surface of PC board (2110), and/or on the exterior surface of transfer casing (2150). Moreover, in some versions brush contacts (2170) may be manufactured using MID technology. It should also be understood that the foregoing PCB electrical coupling assembly (2100) may be used in conjunction with one or more of the electrical coupling assemblies described herein. For instance, PCB electrical coupling assembly (2100) may electrically couple one wire from the cable to transducer (2190) while cable plug (450) of FIG. 6 couples a second wire to a proximal end of transducer (2190). In a further alternative, transfer casing (2150) may be integrated into the handle assembly of the surgical instrument. FIG. 38 depicts such a merely exemplary assembly having transfer casing (2150) integrated into a handle assembly (2198).

ii. Exemplary PCB Electrical Coupling Assembly Having Wave Springs

Figure 39:
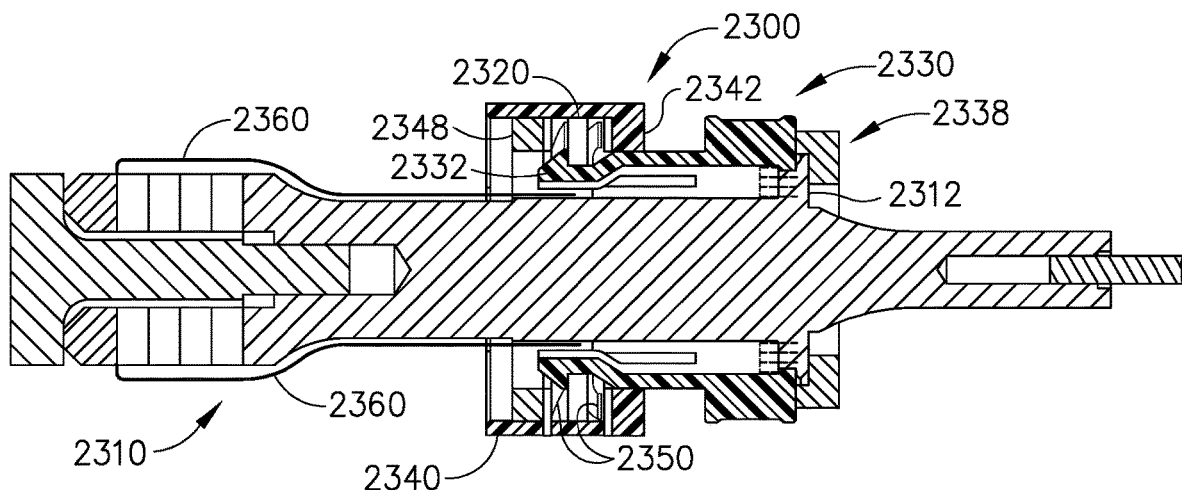
FIG. 39 depicts a side cross-sectional view of an exemplary alternative rotatable electrical coupling assembly having a PC board and conductive wave springs.
Figure 40:
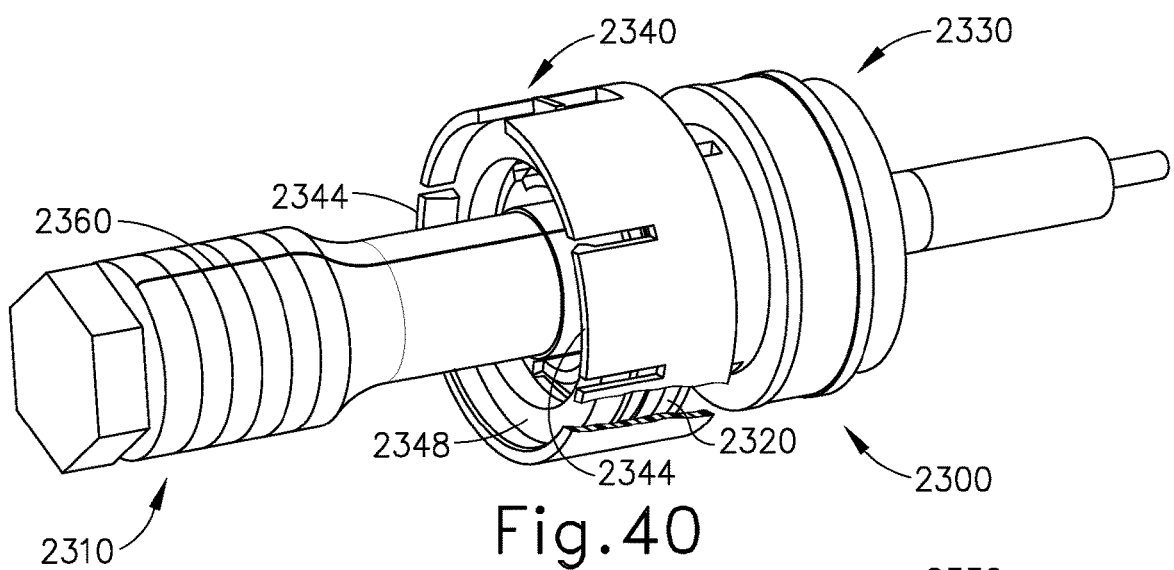
FIG. 40 depicts a perspective view of the exemplary alternative rotatable electrical coupling assembly of FIG. 39 showing a pair of tab arms securing an insertable ring.
Figure 41:
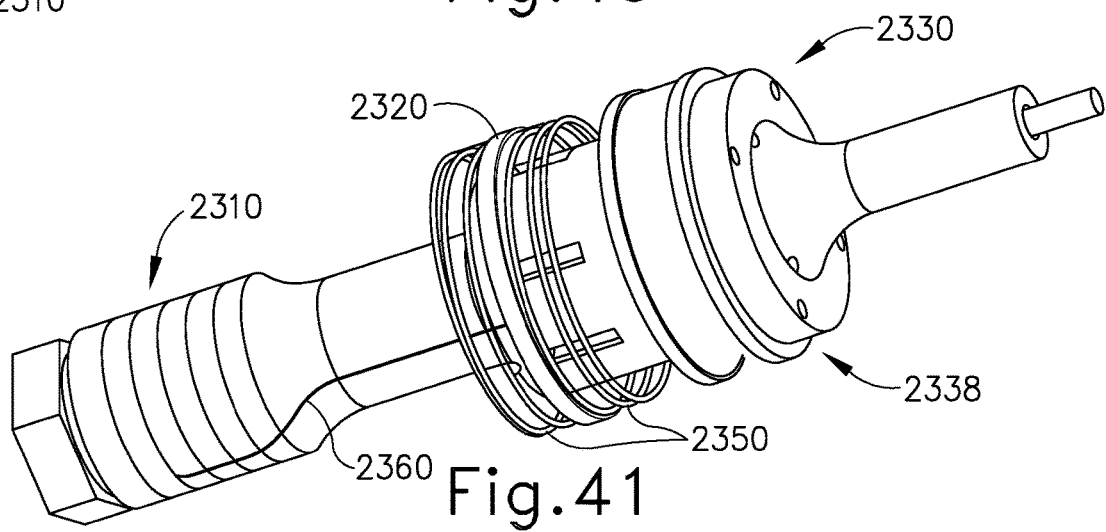
FIG. 41 depicts a perspective view of the exemplary alternative rotatable electrical coupling assembly of FIG. 39 shown with the outer casing omitted.

An exemplary alternative PCB electrical coupling assembly (2300) is shown in FIGS. 39-41. PCB electrical coupling assembly (2300) is configured to electrically couple a cable (not shown) to a transducer (2310). In the present example, PCB electrical coupling assembly (2300) comprises a PC board (2320), a mounting component (2330), an outer casing (2340), a pair of wave springs (2350), and a pair of transducer wires (2360). PC board (2320) of the present example comprises a cylindrical disc with conductive traces (not shown) formed thereon. Such conductive traces may be constructed in accordance with at least some of the teachings of conductive traces (2112) described above. The conductive traces of the present PC board (2320) each have a coupling point, similar to coupling point (2114) described above, to which a transducer wires (2360) electrically couple. In the present example, conductive traces and coupling points are formed on both the proximal and distal sides of PC board (2320), though either side may omit the conductive trace and/or coupling point. PC board (2320) further includes a central aperture configured to couple PC board (2320) to mounting component (2330), as will be described below. PC board (2320) may be further constructed in accordance with PC board (2110) described above or in any other manner as will be apparent to one of ordinary skill in the art in view of the teachings herein.

In the present example, a distal end (2338) of mounting component (2330) is coupled to a distal flange (2312) of transducer (2310). In some versions, mounting component (2330) may include features configured to dampen the vibrations from transducer (2310) (e.g., springs, etc.), though this is merely optional. Mounting component (2330) further includes resilient latching tabs (2332) configured to insert into the central aperture of PC board (2320) such that resilient latching tabs (2332) substantially secure PC board (2320) to mounting component (2330). In some versions, latching tabs (2332) may insert into key slots, such as key slots (2118) described above, of PC board (2320) such that PC board (2320) is rotational coupled to mounting component (2330). Of course it should be understood that this is merely optional and PC board (2320) may be free to rotate relative to mounting component (2330).

A pair of wave springs (2350) (shown best in FIG. 41) are disposed on both the proximal and distal sides of PC board (2320). In the present example, wave springs (2350) are configured to engage and electrically couple to the conductive traces of PC board (2320). Accordingly, when a power supply is coupled to wave springs (2350), the electrical power is transmitted through wave springs (2350), to the conductive traces of PC board (2320), and finally through transducer wires (2360) to the electrodes of transducer (2310). Accordingly, even when transducer (2310) is rotated, wave springs (2350) are continuously electrically coupled to PC board (2320) and supply electrical power to transducer (2310).

In the present example, wave springs (2350) are secured against PC board (2320) by outer casing (2340) and an insertable ring (2348). Outer casing (2340) of the present example comprises a substantially hollow cylindrical member having a distal interior ledge (2342) (shown in FIG. 39) and a pair of resilient latching tab arms (2344) (shown in FIG. 40). Tab arms (2344) are configured to permit insertable ring (2348) to snap into outer casing (2340) from the proximal end of outer casing (2340). Accordingly, as shown in FIG. 39, outer casing (2340) and insertable ring (2348) cooperatively retain wave springs (2350) between interior ledge (2342) and insertable ring (2348). In the present example, outer casing (2340) is longitudinally sized such that wave springs (2350) are compressed against PC board (2320) when insertable ring (2348) is coupled to outer casing (2340). As will be appreciated by one of ordinary skill in the art in view of the teachings herein, if outer casing (2340) is coupled to a handle assembly, such as handle assembly (60), wave springs (2350) may provide an additional damping effect to reduce vibrations transmitted to the handle assembly. Furthermore, by utilizing wave springs (2350), outer casing (2340) need not necessarily be configured to translate within the handle assembly. Other suitable configurations for outer casing (2340) will be apparent to one of ordinary skill in the art in view of the teachings herein.

To assemble PCB electrical coupling assembly (2300), initially mounting component (2330) is decoupled from all the other components and is used as the starting component. Outer casing (2340) is then slid over the proximal end of mounting component (2330) until interior ledge (2342) of outer casing (2340) abuts distal end (2338) of mounting component (2330). A distal wave spring (2350) is then also inserted slid over the proximal end of mounting component (2330) until wave spring (2350) abuts the proximal surface of interior ledge (2348). With outer casing (2340), and distal wave spring (2350) so positioned, PC board (2320) is then coupled to mounting component (2330) via latching tabs (2332). Outer casing (2340) and distal wave spring (2350) are then slid proximally such that interior ledge (2348) compresses distal wave spring (2350) against PC board (2320). A proximal wave spring (2350) is then inserted into outer casing (2340) to abut the proximal side of PC board (2320). Insertable ring (2348) is then snapped in and secured to outer casing (2340) via tab arms (2344). With PCB electrical coupling assembly (2300) substantially assembled, PCB electrical coupling assembly (2300) is then slid over a distal end of transducer (2310) and proximal end (2338) of mounting component (2330) is secured to distal flange (2312). The assembled transducer (2310) and PCB electrical coupling assembly (2300) may then be inserted and used with a surgical instrument. Other suitable configurations for PCB electrical coupling assembly (2300) will be apparent to one of ordinary skill in the art in view of the teachings herein.

Figure 42:
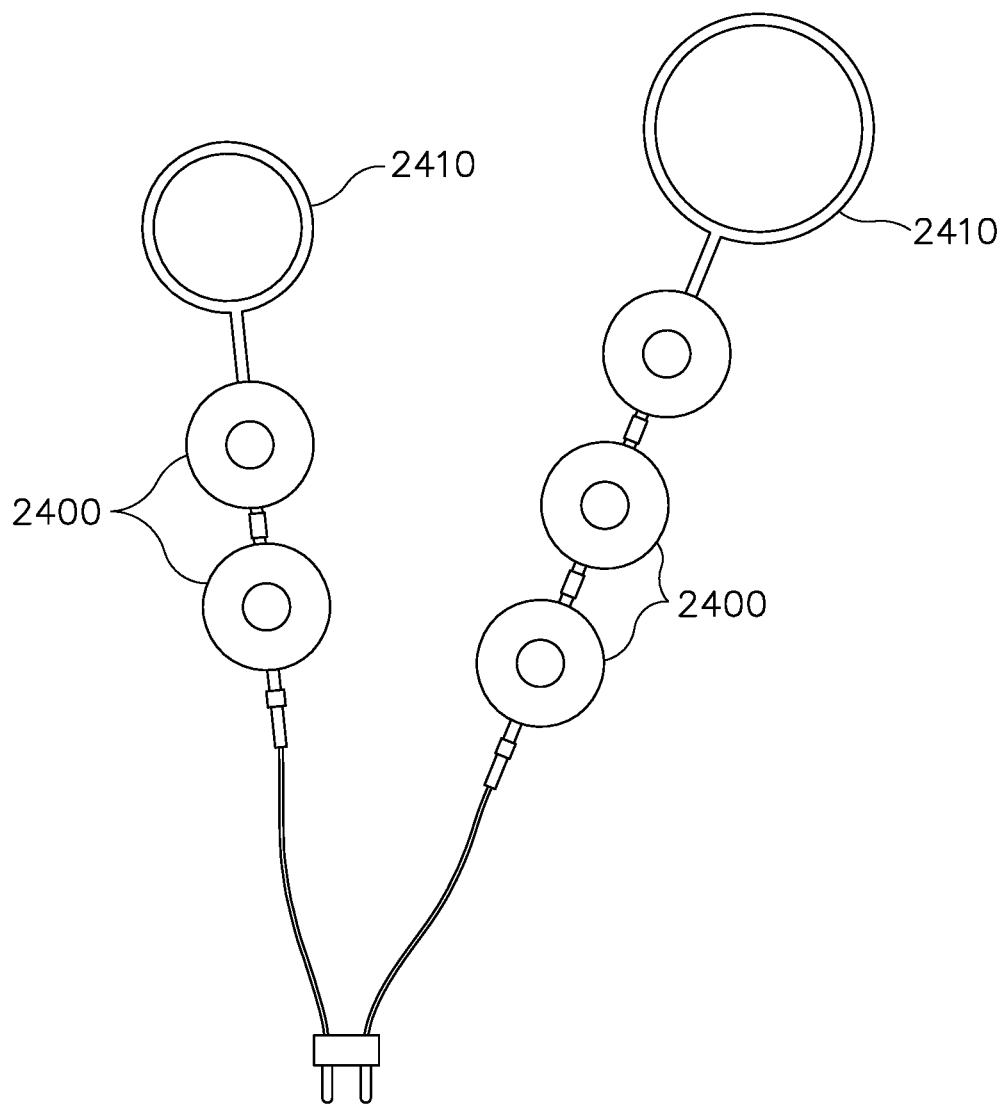
FIG. 42 depicts a top plan view of two strings of electrodes having integrated conductive ring contacts.

In some versions, PC boards (2110, 2320) may omit their respective conductive traces and flat conductive rings may instead be coupled to PC board (2110, 2320). FIG. 42 depicts one merely exemplary set of electrodes (2400) incorporating flat conductive rings (2410) at the end of each set of electrodes (2400). Electrodes (2400) of the present example are alternatingly stacked with the piezoelectric elements of a transducer, such as transducers (100, 300) described above. Once the piezoelectric stack is assembled, flat conductive rings (2410) are positioned distally and are operable to electrically couple to PC boards (2110, 2320). It should be understood that flat conductive rings (2410) may be used with other electrical coupling assemblies. For instance, a plurality of flat conductive rings (2410) may be incorporated into outer housing assembly (700) shown in FIGS. 11-12 or into outer rotor assembly (800) shown in FIG. 13.

III. Exemplary Integrated Controller with Transducer

In some situations it may be preferable to integrate electronic components within a casing for a rotatable transducer (100). Such a configuration may need only a power supply (e.g., generator (20), etc.) to be coupled to the casing in order for transducer (100) to be operable by a user. Moreover, by having the electronic components integrated within the casing of transducer (100), only a single temperature sensor may be needed to monitor both the temperature of transducer (100) and the electronic components. Further still, by including the electronic components within the casing of transducer (100), thicker wires may be used for the electrical couplings due to the short run distances and the reduced need for flexibility. These thicker wires may help mitigate heat generated within the surgical instrument.

Figure 44:
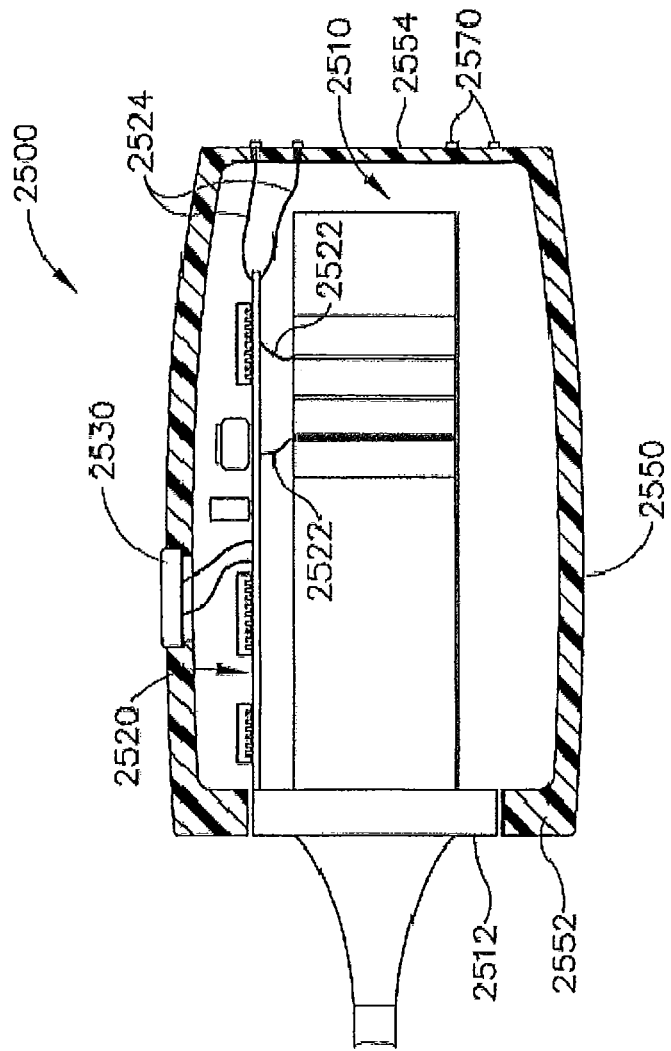
FIG. 44 depicts a partial side cross-sectional view of the exemplary rotatable electrical coupling assembly of FIG. 43 taken along line 44-44 of FIG. 43, showing a circuit board, transducer, and sensor integrated with the casing.
Figure 43:
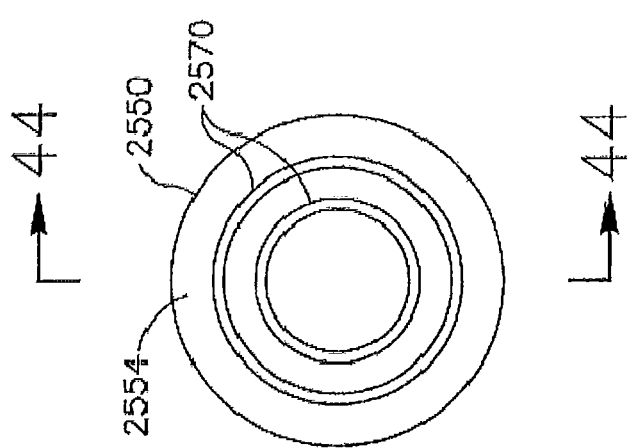
FIG. 43 depicts a rear elevation view of an exemplary rotatable electrical coupling assembly showing a casing having conductive rings.

FIGS. 43-44 depict a transducer assembly (2500) comprising a transducer (2510), a circuit board (2520), a casing (2550), and a pair of conductive rings (2570). Referring initially to FIG. 44, transducer (2510) is secured to casing (2550) by a flange (2512). By way of example only, flange (2512) may be mechanically coupled to a distal wall (2552) of casing (2550). For example, flange (2512) may be secured via threading, clips, snaps, clamps, screws, bolts, adhesives, etc. Other suitable attachments for flange (2512) to distal wall (2552) will be apparent to one of ordinary skill in the art in view of the teachings herein. Transducer (2510) and/or flange (2512) may further be constructed in accordance with at least some of the teachings of transducers (100, 300) and/or otherwise.

In the present example, circuit board (2520) comprises a rigid circuit board coupled to flange (2512), though this is merely optional. In some alternative versions, circuit board (2520) may be coupled directly to casing (2550) or to transducer (2510). In the versions that circuit board (2520) is secured to transducer (2510), circuit board (2520) may comprise a cylindrical or flexible circuit wrapped about transducer (2510). Circuit board (2520) of the present example is electrically coupled to the electrodes of transducer (2510) by wires (2522) and to conductive rings (2570) via wires (2524). In some versions a sensor (2530) may be coupled to circuit board (2520). In the example shown in FIG. 44, sensor (2530) is coupled to casing (2550) and is configured to measure the temperature of transducer (2510) and/or within casing (2550). Sensor (2530) of the present example comprises a positive temperature coefficient ("PTC") sensor, though it should be understood that other sensors, including other types of temperature sensors and/or sensors that do not measure temperature, may be used as well. If sensor (2530) measures a predetermined temperature or a temperature exceeding a predetermined threshold, circuit board (2520) and/or another electronic component may be configured to alert the user (e.g., by auditory, visual, and/or tactile feedback) or to disconnect a power supply coupled to transducer (2510) and/or circuit board (2520). In addition or in the alternative, sensor (2530) and/or some other component may automatically disconnect transducer (2510) and/or circuit board (2520) from a power supply in response to a temperature reaching a certain level or exceeding a predetermined threshold.

Casing (2550) of the present example comprises a thin shell configured to contain transducer (2510) and circuit board (2520) therein. In the instances where circuit board (2520) comprises a flexible circuit, casing (2550) may be decreased in size to substantially conform to the size and shape of transducer (2510). As noted above, casing (2550) is coupled to transducer (2510) at distal wall (2552) of casing (2550). Casing (2550) also includes a proximal wall (2554). Referring back to FIG. 43, proximal wall (2554) of the present example comprises a circular wall having a pair of coaxial conductive rings (2570) coupled to the proximal surface of proximal wall (2554). Conductive rings (2570) are configured to electrically couple to a power supply. By way of example only, pogo pins, conductive ball bearings, brushes, PC boards with conductive traces, and/or other conductive rings may be used to electrically couple the power supply to conductive rings (2570). Accordingly, transducer assembly (2500) may be rotated through 360 degrees without decoupling from the power supply. As noted previously, with circuit board (2520) contained within transducer assembly (2500), power supply may simply comprise a battery that coupled to conductive rings (2570). In some versions, the battery may be coupled to a belt and worn by the user, thereby further enabling the mobility of the user and/or the surgical device. Alternatively, the battery may be integrated into the surgical instrument. Still other suitable configurations for transducer assembly (2500) will be apparent to one of ordinary skill in the art in view of the teachings herein.

For the foregoing examples, it should be understood that the handle assemblies and/or end effectors may be reusable, autoclavable, and/or disposable. For instance, the foregoing end effectors may be disposable while the handle assemblies are reuseable and/or autoclavable. In addition, if internal power supplies are used with the foregoing handle assemblies, the internal power supplies may be rechargeable. For instance, the handle assemblies may be recharged using a plug in recharge, by removing and recharging the batteries, by induction, and/or by any other method as will be apparent to one of ordinary skill in the art in view of the teachings herein. Furthermore, alignment features or guides may be included to aid in the alignment and coupling of the end effectors with handle assemblies. Such guides may help prevent damage to the end effector and/or handle assembly during the assembly of the surgical instrument.

While certain configurations of exemplary surgical instruments have been described, various other ways in which surgical instruments may be configured will be apparent to those of ordinary skill in the art in view of the teachings herein. By way of example only, surgical instruments referred to herein may be constructed in accordance with at least some of the teachings of U.S. Pat. Nos. 6,500,176; 6,783,524; 7,416,101; 7,738,971; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0209990, issued as U.S. Pat. No. 8,657,174 on Feb. 25, 2014; U.S. Pub. No. 2009/0143797, issued as U.S. Pat. No. 8,419,757; U.S. Pub. No. 2010/0069940, issued as U.S. Pat. No. 9,023,071 on May 5, 2015; and/or U.S. Provisional Application Ser. No. 61/410,603, the disclosures of which are herein incorporated by reference.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) an ultrasonic transducer;
   (b) a body portion extending along a longitudinal axis and configured to receive the ultrasonic transducer along the longitudinal axis such that the ultrasonic transducer is rotatable about the longitudinal axis; and
   (c) an electrical coupling assembly configured to electrically connect a power supply of an electrical power to the ultrasonic transducer, the electrical coupling assembly including:
      (i) a first electrical connection including a first wire and configured to electrically connect to the power supply,
      (ii) a second electrical connection electrically connected to the ultrasonic transducer,
      (iii) a first plurality of conductive members secured between the first and second electrical connections, wherein the first plurality of conductive members electrically connect the first and second electrical connections such that the ultrasonic transducer is configured to receive the electrical power from the power supply while rotating the ultrasonic transducer relative to the body portion about the longitudinal axis; and
      (iv) a first annular trough about the longitudinal axis, wherein at least a portion of the first wire is positioned within the first annular trough.

2. The surgical instrument of claim 1, wherein the first plurality of conductive members further includes a first plurality of ball bearings.

3. The surgical instrument of claim 1, wherein the first plurality of conductive members is secured within the first annular trough.

4. The surgical instrument of claim 3, wherein the first annular trough extends through the body portion.

5. The surgical instrument of claim 3, wherein the electrical coupling assembly further includes a second annular trough about the longitudinal axis, wherein the second annular trough is radially inward of the first annular trough, and wherein the first plurality of conductive members is secured within the second annular trough.

6. The surgical instrument of claim 5, wherein the first annular trough extends through the body portion, and wherein the second annular trough extends through the ultrasonic transducer.

7. The surgical instrument of claim 5, wherein at least a portion of the first wire is positioned within the first annular trough, wherein the second electrical connection further includes a second wire, and wherein at least a portion of the second wire is positioned within the second annular trough.

8. The surgical instrument of claim 1, wherein the electrical coupling assembly further includes:
   a third electrical connection configured to electrically connect to the power supply,
   (ii) a fourth electrical connection electrically connected to the ultrasonic transducer,
   (ii) a second plurality of conductive members secured between the third and fourth electrical connections, wherein the second plurality of conductive members electrically connect the third and fourth electrical connections such that the ultrasonic transducer is configured to receive the electrical power from the power supply while rotating the ultrasonic transducer relative to the body portion about the longitudinal axis.

9. The surgical instrument of claim 8, wherein the electrical coupling assembly further includes an insulator positioned between the first plurality of conductive members and the second plurality of conductive members such that the first plurality of conductive members is electrically isolated from the second plurality of conductive members.

10. The surgical instrument of claim 1, wherein the electrical coupling assembly further includes a biasing element configured to urge at least one of the first plurality of conductive members into securement between the first and second electrical connections.

11. The surgical instrument of claim 10, wherein the biasing element is electrically connected to the at least one of the first plurality of conductive members for transmitting the electrical power therethrough.

12. The surgical instrument of claim 11, wherein the biasing element is positioned against the body portion and urges the at least one of the first plurality of conductive members into the first annular trough.

13. The surgical instrument of claim 12, wherein the first plurality of conductive members further includes a first plurality of ball bearings.

14. The surgical instrument of claim 13, wherein the biasing element is a spring, wherein the body portion has a recess therein, and wherein the spring is received within the recess.

15. A surgical instrument, comprising:
   (a) an ultrasonic transducer;
   (b) a body portion extending along a longitudinal axis and configured to receive the ultrasonic transducer along the longitudinal axis such that the ultrasonic transducer is rotatable about the longitudinal axis; and
   (c) an electrical coupling assembly configured to electrically connect a power supply of an electrical power to the ultrasonic transducer, the electrical coupling assembly including:
      (i) a first electrical connection configured to electrically connect to the power supply, (ii) a second electrical connection electrically connected to the ultrasonic transducer, (iii) a first plurality of conductive members secured between the first and second electrical connections, wherein the first plurality of conductive members electrically connect the first and second electrical connections such that the ultrasonic transducer is configured to receive the electrical power from the power supply while rotating the ultrasonic transducer relative to the body portion about the longitudinal axis, (iv) a third electrical connection configured to electrically connect to the power supply, (v) a fourth electrical connection electrically connected to the ultrasonic transducer, and (vi) a second plurality of conductive members secured between the third and fourth electrical connections, wherein the second plurality of conductive members electrically connect the third and fourth electrical connections such that the ultrasonic transducer is configured to receive the electrical power from the power supply while rotating the ultrasonic transducer relative to the body portion about the longitudinal axis.

16. The surgical instrument of claim 15, wherein the electrical coupling assembly further includes an insulator positioned between the first plurality of conductive members and the second plurality of conductive members such that the first plurality of conductive members is electrically isolated from the second plurality of conductive members.

17. A surgical instrument, comprising:
(a) an ultrasonic transducer;
(b) a body portion extending along a longitudinal axis and configured to receive the ultrasonic transducer along the longitudinal axis such that the ultrasonic transducer is rotatable about the longitudinal axis; and
(c) an electrical coupling assembly configured to electrically connect a power supply of an electrical power to the ultrasonic transducer, the electrical coupling assembly including:
  (i) a first electrical connection configured to electrically connect to the power supply,
  (ii) a second electrical connection electrically connected to the ultrasonic transducer,
  (iii) a first plurality of conductive members secured between the first and second electrical connections, wherein the first plurality of conductive members electrically connect the first and second electrical connections such that the ultrasonic transducer is configured to receive the electrical power from the power supply while rotating the ultrasonic transducer relative to the body portion about the longitudinal axis,
  (iv) a biasing element configured to urge at least one of the first plurality of conductive members into securement between the first and second electrical connections, and
  (v) a first annular trough about the longitudinal axis, wherein the biasing element is positioned against the body portion and urges the at least one of the first plurality of conductive members into the first annular trough.

18. The surgical instrument of claim 17, wherein the biasing element is electrically connected to the at least one of the first plurality of conductive members for transmitting the electrical power therethrough.

19. The surgical instrument of claim 18, wherein the first plurality of conductive members further includes a first plurality of ball bearings.

20. The surgical instrument of claim 19, wherein the biasing element is a spring, wherein the body portion has a recess therein, and wherein the spring is received within the recess.

* * * * *